US009501624B2

(12) United States Patent
Vishnubhatla et al.

(10) Patent No.: US 9,501,624 B2
(45) Date of Patent: Nov. 22, 2016

(54) PHARMACY MANAGEMENT AND ADMINISTRATION WITH BEDSIDE REAL-TIME MEDICAL EVENT DATA COLLECTION

(75) Inventors: Suresh-Kumar Venkata Vishnubhatla, Wexford, PA (US); Lena Elizabeth Sturgeon, Washington, PA (US); Christopher Lee Miller, Mercer, PA (US); Ronald Leo McKillip, Seward, PA (US); Andrew Jonathan Lister, South Bend, IL (US); Garick George Newtzie, Mars, PA (US); Joseph B. Poliseo, Southampton, PA (US)

(73) Assignee: Millennium Pharmacy Systems, LLC, Oakbrook, IL (US)

( * ) Notice: Subject to any disclaimer, the term of this patent is extended or adjusted under 35 U.S.C. 154(b) by 301 days.

(21) Appl. No.: 13/568,017

(22) Filed: Aug. 6, 2012

(65) Prior Publication Data

US 2012/0303388 A1 Nov. 29, 2012

Related U.S. Application Data

(62) Division of application No. 12/765,681, filed on Apr. 22, 2010.

(60) Provisional application No. 61/171,767, filed on Apr. 22, 2009, provisional application No. 61/315,775, filed on Mar. 19, 2010.

(51) Int. Cl.
*G06Q 10/00* (2012.01)
*G06Q 50/00* (2012.01)
(Continued)

(52) U.S. Cl.
CPC ......... *G06F 19/3462* (2013.01); *G06F 19/322* (2013.01); *G06F 19/328* (2013.01);
(Continued)

(58) Field of Classification Search
CPC .. G06Q 50/22; G06Q 50/24; G06F 19/3462; G06F 19/322; G06F 19/327
See application file for complete search history.

(56) References Cited

U.S. PATENT DOCUMENTS 5,537,314 A 7/1996 Kanter
5,832,449 A 11/1998 Cunningham
(Continued)

FOREIGN PATENT DOCUMENTS

WO 0221402 A1 3/2002
WO 03017166 A1 2/2003
(Continued)

OTHER PUBLICATIONS

"Operation of Prescription Drugs Plan Varies , Depending upon the Type of System Being Used", Employee Benefit Plan Review, 36(7), Form Dialog eLink: 15, Jan. 1982, pp. 20-24.
(Continued)

*Primary Examiner* — Michelle L Le
(74) *Attorney, Agent, or Firm* — GTC Law Group PC & Affiliates

(57) ABSTRACT

Methods and systems for automatically establishing an enhanced electronic health record (EHR) for a patient include an automatic data collection facility that collects data of a medically related event in proximity to a patient upon occurrence of the event. The collected data may include medication administration data such as medication, time of administration, administration of a dosage of medication, reaction data, and the like. The collected data is communicated to a real-time data integration facility that automatically integrates the data with a patient's electronic health record to establish an enhanced electronic health record.

17 Claims, 15 Drawing Sheets

(51) Int. Cl.
*G06F 19/00* (2011.01)
*G06Q 10/06* (2012.01)
*G06Q 50/22* (2012.01)
*G06Q 50/24* (2012.01)

(52) U.S. Cl.
CPC ......... *G06F19/345* (2013.01); *G06F 19/3443* (2013.01); *G06Q 10/06* (2013.01); *G06Q 50/22* (2013.01); *G06Q 50/24* (2013.01)

(56) References Cited

U.S. PATENT DOCUMENTS

| | | | |
|---|---|---|---|
| 6,493,427 | B1 | 12/2002 | Kobylevsky et al. |
| 7,171,227 | B2 | 1/2007 | Baratz et al. |
| 7,194,301 | B2 | 3/2007 | Jenkins et al. |
| 7,286,997 | B2 | 10/2007 | Spector et al. |
| 7,344,079 | B2 | 3/2008 | Steusloff et al. |
| 7,364,067 | B2 | 4/2008 | Steusloff et al. |
| 7,519,540 | B2 | 4/2009 | Mayaud |
| 7,595,867 | B2 | 9/2009 | Nichols et al. |
| 7,607,571 | B2 | 10/2009 | Steusloff et al. |
| 7,676,299 | B2 | 3/2010 | Clarke et al. |
| 7,685,004 | B2 | 3/2010 | Moncrief et al. |
| 7,685,006 | B2 * | 3/2010 | Rahn et al. ............. 705/3 |
| 7,774,097 | B2 * | 8/2010 | Rosenblum ........... 700/236 |
| 8,219,413 | B2 * | 7/2012 | Martinez et al. .......... 705/2 |
| 2001/0037205 | A1 | 11/2001 | Joao |
| 2002/0002495 | A1 | 1/2002 | Ullman |
| 2002/0035484 | A1 | 3/2002 | Mccormick |
| 2002/0069088 | A1 | 6/2002 | Berg |
| 2003/0041107 | A1 | 2/2003 | Blattner et al. |
| 2003/0144884 | A1 * | 7/2003 | Mayaud ................. 705/3 |
| 2004/0024616 | A1 | 2/2004 | Spector et al. |
| 2005/0004700 | A1 * | 1/2005 | DiMaggio ............ 700/213 |
| 2005/0021175 | A1 | 1/2005 | Bain |
| 2005/0080462 | A1 | 4/2005 | Jenkins et al. |
| 2005/0107914 | A1 * | 5/2005 | Engleson et al. ....... 700/237 |
| 2005/0119914 | A1 | 6/2005 | Batch |
| 2005/0261940 | A1 | 11/2005 | Gay et al. |
| 2006/0161294 | A1 | 7/2006 | DiMaggio |
| 2006/0161298 | A1 | 7/2006 | DiMaggio |
| 2007/0061393 | A1 | 3/2007 | Moore |
| 2007/0250210 | A1 | 10/2007 | Moncrief et al. |
| 2008/0015893 | A1 | 1/2008 | Miller et al. |
| 2008/0015894 | A1 | 1/2008 | Miller et al. |
| 2008/0029601 | A1 | 2/2008 | Clarke et al. |
| 2008/0046292 | A1 | 2/2008 | Myers et al. |
| 2008/0059228 | A1 | 3/2008 | Bossi et al. |
| 2008/0071579 | A1 | 3/2008 | Willson et al. |
| 2008/0091467 | A1 | 4/2008 | Moncrief et al. |
| 2008/0109260 | A1 | 5/2008 | Roof |
| 2008/0126117 | A1 | 5/2008 | Miller et al. |
| 2008/0126131 | A1 | 5/2008 | Lou |
| 2008/0183492 | A1 | 7/2008 | Warren et al. |
| 2008/0294376 | A1 | 11/2008 | Bharara et al. |
| 2009/0043608 | A1 | 2/2009 | Nadas et al. |
| 2009/0048712 | A1 | 2/2009 | Rosenblum |
| 2009/0119129 | A1 | 5/2009 | Nadas et al. |
| 2009/0173779 | A1 | 7/2009 | Szesko et al. |
| 2009/0179072 | A1 | 7/2009 | Szesko et al. |
| 2010/0324936 | A1 | 12/2010 | Vishnubhatla et al. |

FOREIGN PATENT DOCUMENTS

| | | |
|---|---|---|
| WO | 2005043440 A1 | 5/2005 |
| WO | 2006023013 A1 | 3/2006 |
| WO | 2007111910 A2 | 10/2007 |
| WO | 2008019370 A2 | 2/2008 |
| WO | 2010124137 A1 | 10/2010 |

OTHER PUBLICATIONS

PCT/US2010/032122, International Application No. PCT/US2010/032122, International Search Report and Written Opinion mailed Sep. 15, 2010, 21 pages.

* cited by examiner

LONG TERM CARE FACILITY – MEDICATION ADMINISTRATION DASHBOARD

PATIENT NAME: _____ LOCATION: _____ OK: Y / N
PATIENT ID: _____ ADMIN ID: _____

MEDICATION: _____ BARCODE DATA: _____ OK: Y / N

ADMIN DATE: _____ ADMIN OBSERVATIONS: _____
ADMIN TIME: _____

DOSE: _____ PATIENT VITALS:
BP: _____ HR: _____ TEMP: _____

RX WRITTEN: _____ REVIEW OF PRIOR SYMPTOMS:
RX APPROVED: _____ SYMPTOM A: _____
RX FIRST FILLED: _____ SYMPTOM B: _____
RX LAST FILLED: _____
DELIVERY DATE: _____ NEW SYMPTOMS?: _____

Fig. 15

PHARMACY MANAGEMENT AND ADMINISTRATION WITH BEDSIDE REAL-TIME MEDICAL EVENT DATA COLLECTION

CROSS-REFERENCE TO RELATED APPLICATIONS

This application is a Divisional Patent Application claiming the benefit of the parent patent application Ser. No. 12/765,681 filed Apr. 22, 2010 having the same title as this application hereby incorporated by reference in its entirety. Both applications claim the benefit of the following provisional applications, each of which is hereby incorporated by reference in its entirety:

U.S. Ser. No. 61/171,767 filed Apr. 22, 2009 entitled SYSTEMS, METHODS, AND DEVICES FOR AUTOMATED ORDERING, DISPENSING, REPORTING, AND BILLING OF MEDICATION AND THE ASSOCIATED REPORTING AND DOCUMENTATION OF THE ADMINISTRATION OF MEDICATION; and U.S. Ser. No. 61/315,775 filed Mar. 19, 2010 entitled REAL-TIME HEALTHCARE ADMINISTRATION AND OUTCOME DATA COLLECTION AND RECORD UPDATE FOR CARE ADMINISTRATION, PLANNING, OUTCOME PREDICTION, AND PREVENTION.

BACKGROUND OF THE INVENTION

Field

This invention relates to systems, methods, and devices for automated ordering, dispensing, reporting, and billing of medication and the associated reporting and documentation of the administration of medication.

Description of the Related Art

A common scenario with respect to the ordering, dispensing, reporting, billing and documentation of a prescribed medication begins with a physician's handwritten order. This handwritten order must be transmitted to the pharmacy; typically the order is faxed. In other instances, the order can be entered into an electronic computerized physician order entry system "CPOE". A person at the pharmacy reviews the physician order and enters the order into the pharmacy's order management system. This is also the case even where the order is an electronic order such as like one entered into a CPOE system. That is, some sort of manual data entry step takes place to get the order into the pharmacy's order management system. After the data is manually entered, the drug interaction and allergy verification takes place, which may be performed by a software application which is part of the CPOE system or the pharmacy's order management system. Once the drug interaction and allergy verification step is complete, the pharmacist approves the order, which allows it to be filled, and then the drug is dispensed and packaged.

A common way to dispense medications is in a 30 day or a 7 day supply. In long-term care and other institutional-like settings, for example, dispensed medications are delivered to the facility where they will be administered to the patient 150. If there is a change to a patient's prescription during the 30 day cycle, for example, for which the medication was dispensed, then the unused medication must be returned or destroyed. This adds an additional burden to facilities in that they must adhere to proper destruction procedures, and document them accordingly. Dealing with ordered medications which have been dispensed and delivered, but which are no longer current, places a heavy financial burden on payers, (e.g. health care facilities, insurance companies, patients, and the like), and on the pharmacies because many times they are paying for a supply of medications that the patient never uses.

Regarding the administration of the medication, regulations require that the administration of the medication must be documented with a certain degree of specificity and accuracy. Regulations also require a review of such documentation, for example, on a periodic basis. The administration process is further complicated by brand and generic drugs and multiple brands within the generic medications. Accurate maintenance of the records requires the prescriber, dispensing pharmacy, and the administering system and personnel to be in sync with respect to the identification of the medications.

Patient symptom gathering is another area of concern with respect to the accuracy and validity of common practices. At patient touch points, clinicians are often required to listen to a patient describe symptoms and enter those symptoms in a structured language that allows medical personnel to understand how the clinician views the patient report of symptoms. This process naturally introduces misinformation, clinician bias, information gaps, and other factors that contribute to the recorded symptom being different than that reported by the patient. Patients generally report symptoms (e.g. side effects) related to an administration of a medication sooner and with more specificity than is often reported in clinical studies, and the like.

During a patient interview (e.g. office visit), symptoms may not always be reported because clinicians and patients are distracted from this activity by reviewing test results and the like. Ensuring that accurate, patient generated symptom reports are captured at least with each patient touch point may be a critical deficiency in medical practice. Also, in a report authored by a patient, the symptoms tend to be more accurately described than when the same patient is interviewed (orally) by a clinician. Ensuring accurate and timely side effect reporting may be critical to proper and effective medication management.

It is therefore an object of the invention to address the shortcomings described above, along with others that are apparent in this disclosure.

SUMMARY OF THE INVENTION

In embodiments, methods and systems for automatically establishing an enhanced electronic health record (EHR) for a patient in accordance with various embodiments of the present invention may be provided. In embodiments, methods and systems may include an automatic data collection facility and a real-time data integration facility. In embodiments, the automatic data collection facility may collect data of a medically related event in proximity to a patient upon occurrence of the event. The data of the medically-related event may include medication administration data such as medication, time of administration, administration of a dosage of medication, reaction data, and the like. In embodiments, the real-time data integration facility may be in electronic communication with the automatic data collection facility. The real-time data integration facility may automatically integrate the data of a medically-related event with a patient's EHR to establish the enhanced EHR.

In embodiments, the automatic data collection facility may be a machine reader, a reader device, and the like. The machine reader may also be a bar code reader. In embodiments, the reader device may be in electronic communication with a medication administration facility. The reader device may read electronically readable information on packaging of the dosage of medication. In embodiments, a healthcare-related dashboard may be updated in real-time and contemporaneously with establishing the enhanced EHR.

In embodiments, the methods and systems for automatically establishing an enhanced electronic health record (EHR) for the patient may include an input facility adapted to prompt a user to input additional data of the medically-related event.

In embodiments, the enhanced EHR may include prescription management data for a medication that may be identifiable by the medication administration data. Further, the enhanced EHR data may represent a prescription for the medication and medication delivery data, a caregiver treatment outcome data, real-time collected vitals pre and post administration, outcome prediction and variance from prediction, historical data, facility admission data, and the like.

In embodiments, methods and systems for automatically establishing an enhanced electronic health record (EHR) for a patient in accordance with various embodiments of the present invention may be provided. In embodiments, methods and systems may include an automatic data collection facility and a real-time data integration facility. The automatic data collection facility may collect data of a medically-related event in proximity to a patient upon occurrence of the event. The data of the medically-related event may include medication administration data, such as medication, time of administration, administration of a dosage of medication, reaction data, and the like. Further, the real-time data integration facility may automatically integrate in real-time the data of a medically-related event with a patient's EHR to establish the enhanced EHR.

In embodiments, the automatic data collection facility may be a machine reader, a reader device, and the like. The machine reader may also be a bar code reader. In embodiments, the reader device may be in electronic communication with a medication administration facility. Further, the data collection may include reading electronically readable information on a packaging of the dosage of medication with the reader device.

In embodiments, the methods and systems for automatically establishing an enhanced electronic health record (EHR) for the patient may include prompting a user to input additional data of the medically-related event with a user interface associated with the data collection facility.

In embodiments, a healthcare-related dashboard with a portion of the medically-related event data may be updated in real-time and contemporaneously with establishing the enhanced EHR.

In embodiments, methods and systems for automatically establishing an enhanced electronic health record (EHR) for a patient in accordance with various embodiments of the present invention may be provided. In embodiments, methods and systems may include collecting data of a medically-related event with an automatic data collection facility in proximity to a patient upon occurrence of the event. The data of the medically-related event may include raw medication administration data, such as medication, time of administration, administration of a dosage of medication, reaction data, and the like. The raw medication data may also include a bar code. In embodiments, the raw medication administration data collected by the automatic data collection facility may be transformed with a processor into a format that may be suitable for use in an enhanced electronic healthcare database record. Further, the real-data of a medically-related event may be integrated in real-time with a patient's EHR to establish the enhanced EHR.

In embodiments, the automatic data collection facility may be a machine reader, a reader device, and the like. The machine reader may also be a bar code reader. In embodiments, the reader device may be in electronic communication with a medication administration facility. Further, the data collection may include reading electronically readable information on a packaging of the dosage of medication with the reader device.

In embodiments, the methods and systems for automatically establishing an enhanced electronic health record (EHR) for the patient may include prompting a user to input additional data of the medically-related event into a user interface associated with the data collection facility.

In embodiments, a healthcare-related dashboard with a portion of the medically-related event data may be updated in real-time and contemporaneously with establishing the enhanced EHR.

In embodiments, methods and systems for automatically maintaining an enhanced electronic health record (EHR) in accordance with various embodiments of the present invention may be provided. In embodiments, methods and systems may include an automatic data collection facility and a real-time data integration facility. In embodiments, the automatic data collection facility may collect data of a healthcare-related event in proximity to a patient upon occurrence of the event. The data of the healthcare-related event may include medication administration data, such as medication, time of administration, administration of a dosage of medication, reaction data, and the like. In embodiments, the real-time data integration facility may be in electronic communication with the automatic data collection facility. The real-time data integration facility may automatically integrate the data of a healthcare-related event with a patient's EHR to maintain the enhanced EHR.

In embodiments, the automatic data collection facility may be a machine reader, a reader device, and the like. The machine reader may also be a bar code reader. In embodiments, the reader device may be in electronic communication with a medication administration facility. The reader device may read electronically readable information on packaging of the dosage of medication.

In embodiments, the methods and systems for automatically establishing an enhanced electronic health record (EHR) for the patient may include an input facility adapted to prompt a user to input additional data of the health-related event. In embodiments, a healthcare—related dashboard that may be updated in real-time and contemporaneously with establishing the enhanced EHR.

In embodiments, the enhanced EHR may include prescription management data for a medication that may be identifiable by the medication administration data. Further, the enhanced EHR data may represent a prescription for the medication and medication delivery data, a caregiver treatment outcome data, real-time collected vitals pre and post administration, outcome prediction and variance from prediction, historical data, facility admission data, and the like.

In embodiments, methods and systems for automatically maintaining an enhanced electronic health record (EHR) for a patient in accordance with various embodiments of the present invention may be provided. In embodiments, methods and systems may collect data of a healthcare-related event with an automatic data collection facility in proximity to a patient upon occurrence of the event. The data of the healthcare-related event may include medication administration data such as medication, time of administration, administration of a dosage of medication, reaction data, and the like. In embodiments, the data of a healthcare-related event may be integrated in real-time with a patient's EHR to maintain the enhanced EHR.

In embodiments, the automatic data collection facility may be a machine reader, a reader device, and the like. The machine reader may also be a bar code reader. In embodiments, the reader device may be in electronic communication with a medication administration facility. The reader device may read electronically-readable information on packaging of the dosage of medication.

In embodiments, the methods and systems for automatically establishing an enhanced electronic health record (EHR) for the patient may include prompting a user to input additional data of the healthcare-related event. In embodiments, a healthcare-related dashboard with a portion of the healthcare-related event data may be updated in real-time and contemporaneously with establishing the enhanced EHR.

In embodiments, methods and systems for automatically maintaining an enhanced electronic health record (EHR) for a patient in accordance with various embodiments of the present invention may be provided. In embodiments, methods and systems may collect data of a healthcare-related event with an automatic data collection facility in proximity to a patient upon occurrence of the event. The data of the healthcare-related event may include raw medication administration data, such as medication, time of administration, administration of a dosage of medication, reaction data, and the like. The raw medication data may also include a bar code. In embodiments, the raw medication administration data collected by the automatic data collection facility may be transformed with a processor into a format that may be suitable for use in an enhanced electronic healthcare database record. Further, the data of a healthcare-related event may be integrated in real-time with a patient's EHR to maintain the enhanced EHR.

In embodiments, the automatic data collection facility may be a machine reader, a reader device, and the like. The machine reader may also be a bar code reader. In embodiments, the reader device may be in electronic communication with a medication administration facility. In embodiments, the data collection may include reading electronically readable information on a packaging of the dosage of medication with the reader device.

In embodiments, the methods and systems for automatically establishing an enhanced electronic health record (EHR) for the patient may include prompting a user to input additional data of the healthcare-related event into a user interface with the data collection facility. In embodiments, a healthcare-related dashboard with a portion of the healthcare-related event data may be updated in real-time and contemporaneously with establishing the enhanced EHR.

In embodiments, methods and systems for automatically establishing an enhanced electronic health record (EHR) for a patient in accordance with various embodiments of the present invention may be provided. In embodiments, methods and systems may collect data of a medically-related event with an automatic data collection facility in proximity to a patient upon occurrence of the event. The data of the medically-related event may include medication administration data and another type of data of the medically-related event. In embodiments, the medication administration data may be medication, time of administration, administration of a dosage of medication, reaction data, and the like. In embodiments, the other type of the medically-related event may include patient health condition data, patient physical activity data, patient treatment data, patient oral consumption data; patient visitor data, patient outcome data, patient psychological data, and the like. In embodiments, the patient health condition data may include patient vital signs, patient blood chemistry results, and the like. In embodiments, the patient physical activity data may include patient position and movement facilitated by a caregiver, patient sleep data, and the like. In embodiments, the patient treatment data may include bathing, dressing, wound care, bed position adjustment, physical therapy, psychotherapy, patient position adjustment, and the like. In embodiments the patient oral consumption data may represent foods prepared for the patient and foods consumed by the patient, fluids consumed by the patient, non-prescription medications consumed by the patient, and the like. In embodiments, the patient psychological data may be collected by observation of the patient by a caregiver observing the patient In embodiments, methods and systems for automatically maintaining an enhanced electronic health record (EHR) for a patient in accordance with various embodiments of the present invention may be provided. In embodiments, methods and systems may include an automatic data collection facility and a real-time data integration facility. In embodiments, the automatic data collection facility may collect data of a medically-related event in proximity to a patient upon occurrence of the event. The data of the medically-related event may include medication administration data that may include patient identification data that may be collected from a medication container contemporaneously with the medically-related event. In embodiments, the real-time data integration facility may be in electronic communication with the automatic data collection facility. The real-time data integration facility may automatically integrate the data of a medically-related event with a patient's EHR to maintain the enhanced EHR.

In embodiments, methods and systems for automatically maintaining an enhanced electronic health record (EHR) for a patient in accordance with various embodiments of the present invention may be provided. In embodiments, methods and systems may include collecting data of a medically-related event in proximity to a patient upon occurrence of the event with an automatic data collection facility. The data of the medically-related event may include medication administration data that may include patient identification data that may be collected from a medication container contemporaneously with the medically-related event. In embodiments, the data of a medically-related event may be integrated in real-time automatically with a patient's EHR to maintain the enhanced EHR.

In embodiments, methods and systems for automatically maintaining an enhanced electronic health record (EHR) for a patient in accordance with various embodiments of the present invention may be provided. In embodiments, methods and systems may collect data of a medically-related event with an automatic data collection facility in proximity to a patient upon occurrence of the event. The data of the healthcare-related event may include raw medication administration data. The raw medication administration data may include patient identification data that may be collected from a medication container contemporaneously with the medically-related event. In embodiments, the raw medication administration data collected by the automatic data collection facility may be transformed with a processor into a format that may be suitable for use in an enhanced electronic healthcare database record. Further, the data of a medically-related event may be integrated in real-time automatically with a patient's EHR to maintain the enhanced EHR.

In embodiments, methods and systems for automatically maintaining an enhanced electronic health record (EHR) for a patient in accordance with various embodiments of the present invention may be provided. In embodiments, methods and systems may include an automatic data collection facility and a real-time data integration facility. In embodiments, the automatic data collection facility may collect data of a medically-related event in proximity to a patient upon occurrence of the event. The data of the medically-related event may include medication administration data. In embodiments, the data of the medically-related event may include data for a medication that was prescribed but not administered during the occurrence of the event. In embodiments, the real-time data integration facility may be in electronic communication with the automatic data collection facility. The real-time data integration facility may automatically integrate the data of a medically-related event with a patient's EHR to establish the enhanced EHR.

In embodiments, methods and systems for automatically maintaining an enhanced electronic health record (EHR) for a patient in accordance with various embodiments of the present invention may be provided. In embodiments, methods and systems may collect data of a medically-related event with an automatic data collection facility in proximity to a patient upon occurrence of the event. The data of the medically-related event may include medication administration data. In embodiments, the data of the medically-related event may include data for a medication that was prescribed but not administered during the occurrence of the event. Further, the data of a medically-related event may be integrated in real-time automatically with a patient's EHR to maintain the enhanced EHR.

In embodiments, methods and systems for automatically maintaining an enhanced electronic health record (EHR) for a patient in accordance with various embodiments of the present invention may be provided. In embodiments, methods and systems may collect data of a medically-related event with an automatic data collection facility in proximity to a patient upon occurrence of the event. In embodiments, the medically-related event may be a medication administration event. Further, the data of the medically-related event may include a raw data for a medication that was prescribed but not administered during the occurrence of the event. In embodiments, the raw data for a medication collected by the automatic data collection facility may be transformed with a processor into a format that may be suitable for use in an enhanced electronic healthcare database record. Further, the data of a medically-related event may be integrated in real-time automatically with a patient's EHR to maintain the enhanced EHR.

In embodiments, methods and systems for maintaining a health information dashboard in accordance with various embodiments of the present invention may be provided. In embodiments, methods and systems may include an automatic data collection facility, a real-time data integration facility, and a user interface. In embodiments, the automatic data collection facility may collect data of a medically-related event in proximity to a patient upon the occurrence of the event. The data of the medically-related event may include medication administration data. In embodiments, the real-time data integration facility in electronic communication with the automatic data collection facility may automatically integrate the data of a medically-related event into a data repository. Further, the user interface may display data from the data repository. In embodiments, the displayed data may facilitate management of health care administration.

In embodiments, the user interface display may be updated with the data of a medically-related event contemporaneously with integrating the data of a medically-related event into a data repository.

In embodiments, the data repository may be an enhanced electronic health record of a patient. In embodiments, the data from the data repository may include patient attribute data, patient's prescription data, patient's validated prescription data, patient's prescription history data, and prescription substitution data. In embodiments, the data repository may relate to the time of medication administration, frequency of administration of the medication, dosage of medication administered to the patient, medication that was prescribed but not administered, and outcome data. The patient attribute data may include health condition data, patient physical activity data, patient treatment data, patient outcome data, and patient psychological data. In embodiments, the outcome data may include a patient's response to the medication, measure of the patient's health condition, improvement or worsening of the patient's health condition, improvement or worsening of a symptom, onset of new symptoms, degree of pain, degree of fatigue, physical functioning, emotional distress and social role participation, and the like.

In embodiments, the management of health care administration may include management of health care administration of a facility, management of health care administration of care planning for one or more patients, management of health care administration of facility planning, management of health care administration of insurance planning, management of health care administration of prescription writing, management of health care administration of prescription management, management of health care administration of pharma-related planning, management of health care administration of regulatory compliance, management of health care administration of use of third-party healthcare data management facilities, management of health care administration of medication administration, and the like.

In embodiments, methods and systems for maintaining a health information dashboard in accordance with various embodiments of the present invention may be provided. The methods and systems may include collecting data of a medically-related event with an automatic data collection facility in proximity to a patient upon the occurrence of the event. In embodiments, the data of a medically-related event may include medication administration data. In embodiments, the data of the medically-related event may be integrated in real-time automatically in to a data repository. Further, dashboard of a user interface data may be displayed from the data repository, the displayed data facilitating management of health care administration.

In embodiments, methods and systems for maintaining a health information dashboard in accordance with various embodiments of the present invention may be provided. The methods and systems may include collecting data of a medically-related event with an automatic data collection facility in proximity to a patient upon the occurrence of the event. In embodiments, the data of medically-related event may include raw medication administration data. In embodiments, the data of the medically-related event may be integrated in real-time automatically in to a data repository. Further, dashboard of a user interface data may be displayed from the data repository, the displayed data facilitating management of health care administration.

In embodiments, methods and systems including a dashboard system to manage the prescribing and administration of medication in accordance with various embodiments of the present invention may be provided. In embodiments, a medication administrator records (MAR) facility may be configured to access a database having information from a reporting source therein. The reporting source may include an automatic data collection facility for collecting data of a medically-related event in proximity to a patient upon the occurrence of the event. The data of medically-related event may include medication administration data. Further, a user selectable dashboard definer may be configured to provide user selectable options for defining the information from the MAR facility to be presented in a report at a dashboard. In embodiments, a display definer may be configured to operate in conjunction with the user selectable dashboard definer to define the format in which the report from the MAR facility is to be presented at a dashboard.

In embodiments, the MAR facility may be configured to determine an ordered medication for a patient and medication may be administered to a patient covered by the patient's insurance. The aggregate covered and non-covered medications may be determined into sets. Further, the report may be generated, in real-time, regarding the sets. In embodiments, the communication with the reporting source may be real-time. In embodiments, the dashboard may generate a display based on the continuously received data. In embodiments, the display may feature analysis and report tools.

In embodiments, methods and systems for predicting a health-related outcome of a patient with a health condition in accordance with various embodiments of the present invention may be provided. The methods and systems may include an automatic data collection facility, real-time data integration facility, a prediction facility, and the like. In embodiments, the automatic data collection facility may collect data of a medically-related event in proximity to a patient upon the occurrence of the event. The data of the medically-related event may include automatically collected medication administration data and outcome data. In embodiments, the real-time data integration facility in electronic communication with the automatic data collection facility may automatically integrate the data of a medically-related event into a data repository. In embodiments, the prediction facility in electronic communication with the data repository may utilize the data of a medically-related event for predicting the health-related outcome.

In embodiments, the outcome data may include the patient's response to the medication, a measure of the patient's health condition, and the like. In embodiments, the outcome data may relate to an improvement or worsening of the patient's health condition, an improvement or worsening of a symptom associated with the patient's health condition, onset of new symptoms associated with the patient's health condition, degree of pain associated with the patient, degree of fatigue associated with the patient, physical functioning associated with the patient, emotional distress associated with the patient, social role participation associated with the patient, patient's response to the medication, measure of the patient's health condition, an improvement or worsening of the patient's health condition, and the like.

In embodiments, the automatic data collection may collect data from a medication container contemporaneously with the medically-related event. The data of a medically-related event may include data for a medication that was prescribed but not administered during the occurrence of the event.

In embodiments, an input facility may be present for entering other data of the medically-related event. In embodiments, the other data may include patient health condition data patient, physical activity data, patient treatment data, patient oral consumption data, patient visitor data, patient psychological data, caregiver observations, and the like.

In embodiments, the prediction of the health-related outcome may be based on medically-related event data for a plurality of patients in the data repository. The data repository may include a plurality of real-time electronically updated patient enhanced electronic health records. The data repository may be an enhanced electronic health record of the patient. Further, the data repository may also include individual patient outcome data collected in real-time from a plurality of individual patients.

In embodiments, the prediction facility may be for collecting and organizing the outcome data for facilitating clinical outcome prediction, server executing machine learning software, an analytic workbench for drawing inferences as to whether certain data in the data repository has statistical significance in the outcome data.

In embodiments, the prediction facility may use statistical analysis techniques selected from the list containing regression analysis, iterative analysis, complex modeling, multivariable analytics, Analysis of Variance (ANOVA), Chi-square test, Correlation, Factor analysis, Mann-Whitney U, Mean square weighted deviation (MSWD), Pearson product-moment correlation coefficient, Regression analysis, Spearman's rank correlation coefficient, Student's t-test, Time series analysis, Bootstrap & Jackknife Resampling, Statistical classification, Statistical surveys, Structured data analysis (statistics), Survival analysis, Multivariate discriminant analysis, Linear discriminant analysis, Cluster analysis, and Principal component analysis.

In embodiments, predicting the health-related outcome may include weighting the outcome data. Further, weighting the outcome data may be based on financial data associated with a medication identifiable by the medication administration data. In embodiments, based on the predicted health-related outcome long-term care plan for the patient may be maintained, prescription management may be facilitated, prescription management business rules may be updated, a pharmaceutical-related plan may be updated, management of regulatory compliance may be facilitated, prescription writing based may be facilitated, facilitating management of insurance planning, facilitating management of facility planning, facilitating management of care planning for a plurality of patients, and facilitating health care administration.

In embodiments, methods and systems for predicting a health-related outcome of a patient with a health condition in accordance with various embodiments of the present invention may be provided. In embodiments, the data of a medically-related event may be collected with an automatic data collection facility in proximity to a patient upon the occurrence of the event. In embodiments, the data of the medically-related event may include automatically collected medication administration data and event outcome data. Further, the data of the medically-related event may be integrated in real-time automatically into a data repository. Additionally, the data of the medically-related event may be utilized for predicting the health-related outcome. In embodiments, collecting data of a medically-related event may include collecting data from a medication container contemporaneously with the medically-related event. The data of a medically-related event may include data for a medication that was prescribed, but not administered during the occurrence of the event. In embodiments, the outcome data is the patient's response to the medication, a measure of the patient's health condition, and an improvement or worsening of the patient's health condition.

In embodiments, methods and systems for predicting a health-related outcome of a patient with a health condition in accordance with various embodiments of the present invention may be provided. In embodiments, the data of a medically-related event may be collected with an automatic data collection facility in proximity to a patient upon the occurrence of the event. The data of the medically-related event may include automatically collected raw medication administration data and raw event outcome data. The raw medication administration data and raw event outcome data collected by the automatic data collection facility may be transformed with a processor into a format suitable for use in a medical information data repository. Further, the data of the medically-related event may be integrated in real-time automatically into the data repository. Lastly, the data of the medically-related event may be utilized for predicting the health-related outcome.

In embodiments, methods and systems for managing administration, billing, and filling orders for medication may be provided. In embodiments, the methods and systems may include a medication administration facility, a medication order and billing facility, a reporting interface, an automatic data collection facility, a real-time data integration facility, and the like. In embodiments, the medication administration facility may automatically receive data related to actual administration of medications. In embodiments, the medication order and billing facility may store data related to orders and cost of the administered medication. In embodiments, the medication administration facility, and the medication order and billing facility may be a two-way communication in real-time. Further, the medication administration facility and the medication order and billing facility may be in real-time communication with the reporting interface.

In embodiments, the data related to actual administration of medications may be automatically received from an automatic data collection facility for collecting medication administration data in proximity to a patient upon the occurrence of the administration.

In embodiments, the real-time data integration facility may be in electronic communication with the medication administration facility. The real-time data integration facility may automatically integrate the data related to actual administration of medications with a patient's electronic health record to establish the enhanced electronic health record.

In embodiments, the real-time data integration facility may be a two-way communication in real-time with the medication order and billing facility and the medication administration facility, and in real-time communication with the reporting interface.

These and other systems, methods, objects, features, and advantages of the present invention will be apparent to those skilled in the art from the following detailed description of the preferred embodiment and the drawings. All documents mentioned herein are hereby incorporated in their entirety by reference.

BRIEF DESCRIPTION OF THE FIGURES

The invention and the following detailed description of certain embodiments thereof may be understood by reference to the following figures:

FIG. 15 depicts a medicine administration dashboard.

DETAILED DESCRIPTION OF THE PREFERRED EMBODIMENT(S)

Figure 1:
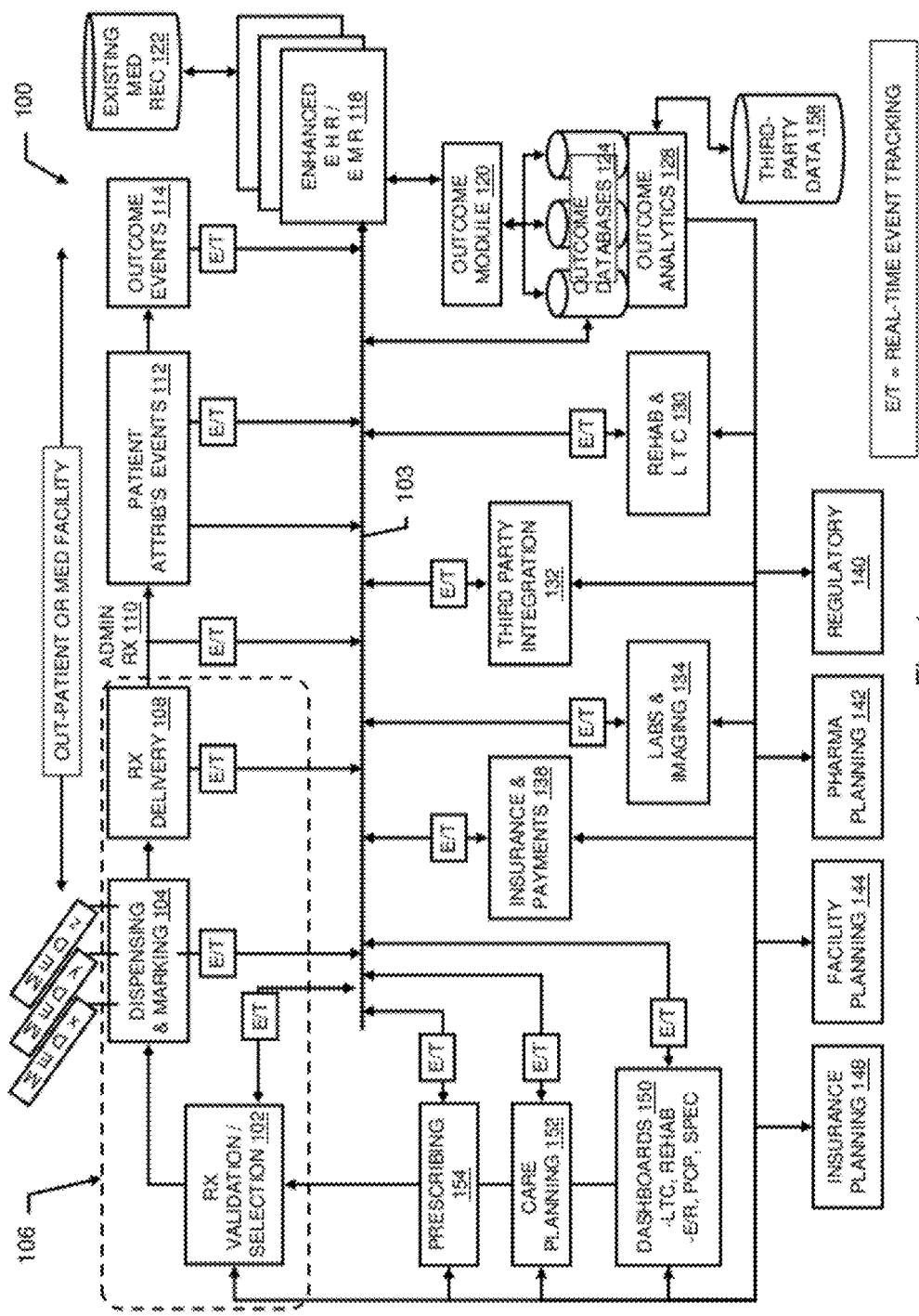
FIG. 1 depicts a block diagram of a healthcare and pharmacy data management and administration method and system (HPDMA)

FIG. 1 is a block diagram showing an overview of a healthcare and pharmacy data management and administration method and system (HPDMA) 100 that may facilitate ordering, dispensing, reporting, billing, planning, outcome collection, outcome analysis and prediction, third party data and services integration, real-time data collection and transfer, user interfaces, documentation, and the like related to a prescription, such as a prescribed medication, and to various patient-related events and outcomes, such as relating to a patient who is taking a prescribed medication. Referring to FIG. 1, various facilities may be included in the HPDMA 100 including a medical prescription (RX) validation and selection facility 102 (alternatively referred to as a medication management facility), a dispensing and marking facility 104, an RX delivery facility 108 (note items 102, 104, and 108 may collectively be referred to as a prescription management facility 106), a prescription administration facility 110 (also referred to herein as a medication administration facility), a patient attributes and events facility 112, an outcome events facility 114, an Enhanced Electronic Health Record (E-EHR)/an Enhanced Electronic Medical Record (E-EMR) facility 118, an outcome facility 120, an existing medical record facility 122, an outcome database facility 124, an outcome analytics facility 128, a rehabilitation and Long Term Care ("LTC") facility 130, a third party integration facility 132, labs and imaging facility 134, an insurance and payments facility 138, a regulatory facility 140, a pharmaceutical (pharma) planning facility 142, a facility planning facility 144, an insurance planning facility 148, a dashboard facility 150, a care planning facility 152, a prescribing facility 154 and a third party data facility 158. Each facility may individually be communicatively connected together through a network, such as the Internet, a proprietary network, a virtual private network, or the like, to facilitate real-time data capture and communication of data among the facilities. Although FIG. 1 depicts the facilities described above and elsewhere herein, HPDMA 100 may not be limited to only these facilities and may include other medical-related facilities, such as other data facilities, care facilities, prescription facilities, communication facilities, and the like.

The prescribing facility 154 may allow a doctor, physician, nurse, pharmacist, or a healthcare specialist to enter an order for a prescription of a medication or other medical care items for a patient. The HPDMA 100 may apply a plurality of identification methods to uniquely identify, record, and document details of person entering the orders. The prescribing facility 154 may be communicatively coupled in real-time to a backbone network 103. The backbone network 103 may be a network that may be communicatively coupled to other facilities of the HPDMA 100 and elsewhere and may carry medical data being communicated among the facilities, such as real-time medical data event packets, files, or streams. The exemplary medical event data being carried over the backbone 103 may include information from any of the facilities depicted in FIG. 1 including, without limitation prescribing units, care planning facilities, laboratories and imaging centers, insurance and payments units, rehabilitation and LTC facilities, electronic medical record repositories, dashboards and databases, third-party sites, healthcare facilities, and the like. In an exemplary case, the backbone network 103 may be the Internet, an intranet, a Wide Area Network, a Local Area Network, a wireless network, a personal area network, a virtual private network, or any other type of wired, wireless, or logical network including ad hoc, peer-to-peer, hub-and-spoke, tree, ring, serial, infrastructure-type protocols, and the like. The backbone network 103 may also facilitate secure communication among different facilities of the HPDMA 100, using firewalls, password protection, anti-virus protection, packet inspection, spam filtering, and other security facilities.

Further, the prescribing facility 154 may obtain patient information via the backbone network 103. The information may include the medical history, clinical outcomes, allergic reactions to certain types of drugs and similar kind of information related to the patient. The prescribing facility 154 may also allow the healthcare specialist to prescribe medication, such as through an electronic order entry facility (not shown in FIG. 1). In an example, the electronic order entry facility may comprise an interface for aiding a healthcare specialist to prescribe the medication or treatment for the patient. The prescribing facility 154 may present the obtained patient information to the healthcare specialist to help facilitate prescribing appropriate medication or treatment for the patient. Once the healthcare specialist enters the prescription of the patient in the electronic order entry facility, the prescribing facility 154 may communicate the prescription to the backbone network 103 or may sent it directly to the prescription management facility 106, and in embodiments directly to the prescription validation/selection facility 102 therein. This communication may be done in real-time as an event. Further, the prescription may be made available to all other facilities of the HPDMA 100 via the backbone network 103.

In an embodiment of the invention, the prescription from the prescription facility 154 may be raw prescription data associated with the patient. The raw prescription data may not be in a format that may be integrated with the E-EHR/E-EMR facility 118. The prescription facility 154 may include a computer (not shown in the FIG. 1) that may transform the raw prescription data to a format such that it may be integrated with the patient's EHR in the E-EHR/E-EMR facility 118.

The prescription may be received by an RX validation and selection facility 102 either directly from the prescribing facility 154 or over the backbone network 103 to which the RX validation and selection facility 102 may be communicatively coupled. The RX validation and selection facility 102 may be configured to receive/send real-time event tracking data with other patient medical related facilities. Further, the RX validation and selection facility 102 may also obtain information regarding the patient, including the past medical history of the patient, treatment outcomes for the patient (from past or current treatments), allergic reactions to certain types of drugs and similar kinds of information. The RX validation and selection facility 102 may thus embody various features to ensure improved probability of selecting and delivering the appropriate medication to the patient, such as modules for identifying patient allergies or sensitivities, modules for identifying potential interactions among medications prescribed or proposed to be prescribed, and modules that use information or insights derived from the outcome module 120, such as to propose medications that have produced favorable outcomes in other similar patients.

In an exemplary case, the RX validation and selection facility 102 may be a pharmacy facility and may include the services of a pharmacist to validate the medical prescription of the patient. In another exemplary case, the pharmacist may be provided with a graphical user interface for performing validation of the medical prescription. Further, in such an interface, a user may utilize various buttons, list boxes, and text boxes for viewing, entering and managing data, such as patient data, medication data, outcome data, and order entry data. In order to confirm the validity of data entered, the software underlying the graphical user interface may validate the entered data, such as for proper format and for the absence of various problems, such as unfavorable interactions with other medications, conflict with patient allergy information, indication of a likely unfavorable outcome, deviation for standards (such as in units prescribed, frequency of prescription, or the like).

By way of example, once the RX validation and selection facility 102 has received the medical prescription and the other details and information about the patient, the RX validation and selection facility 102 may verify formulary compliance, determine drug allergy information associated with the prescribed drugs, and confirm the drug interaction information associated with the prescribed medication. The RX validation and selection facility 102 may issue alerts or warnings to the pharmacist, the healthcare specialist entering the medication order on a patient-by-patient basis to provide an opportunity for the prescriber to consider the prescription in light of these warnings and potentially make adjustments in the prescription before the RX validation and selection facility 102 accepts the order into its processing facilities. After these activities have been accomplished and after reviewing all the relevant patient information, a pharmacist associated with the RX validation and selection facility 102 may validate the patient medical prescription. This pharmacist-based validation may be done as a manual confirmation that follows a series of automated validation steps as described herein. The RX validation and selection facility 102 may communicate the validated prescription of the patient to other facilities of the HPDMA 100 via the backbone network 103.

In an embodiment of the invention, the validated prescription from the RX validation and selection facility 102 may be raw validated prescription data associated with the patient. The raw validated prescription data may not be in a format that may be integrated with the E-EHR/E-EMR facility 118. The RX validation and selection facility 102 may include a computer (not shown in the FIG. 1) that may transform the raw validated prescription data to a format such that it may be integrated with the patient's EHR in the E-EHR/E-EMR facility 118.

After the prescription has been validated, the validated prescription may be received by the dispensing and marking facility 104. The validated prescription may be received with associated information regarding formulary compliance, drug allergy information, drug interaction information, brand versus generic prescription requirements, non-active ingredients of generic medications, costs and inventory information related to the medication, and the like. The information may be provided via a user interface which is accessible on a work station or maybe sourced from other facilities or data sources, such as through the backbone 103. The dispensing and marking facility 104 may receive the validated prescription and the associated information in real-time from the communicatively coupled back bone network 103. In an exemplary case, the dispensing and marking facility 104 may be a pharmacy or may include automated dispensing and labeling machines within a pharmacy. Although, as with all facilities described herein, this facility or portions thereof may be coded instructions executed by various processing and/or computing means disclosed herein. Further, the dispensing and marking facility 104 may prepare the medication order according to the validated medication and may associate certain relevant data with the medication orders. The associated data could include patient identification information, the facility in which the patient resides or receives care, locations within the facility (such as wing, floor, room, and the like), patient insurance information, facility personnel associated with/responsible for the patient, administration frequency, and the like. The patient-related information (e.g. patient attributes/events 112) may be received either electronically via interfaces with other systems (e.g. through the backbone 103) or via manual inputs.

The dispensing and marking facility 104 may determine which medication to dispense based on the prescription, the frequency of administration, and the like. In an example, based on inventory availability, the dispensing and marking facility 104 may apply business rules to select a medication that results in a different frequency of medication administration. The dispensing and marking facility 104 may also take into consideration patient care factors, such as sleeping hours, daylight, and the like to determine a time/date for each administration of the medication. This may be called administration frequency type. In an exemplary case, a frequency type is related to how many times per day a medication is to be administered; for example, twice a day or three times a day. Because "a day" may be defined as the waking hours of the patient, a prescription that has a frequency type of 3 times per day may result in prescription administration times of 7 AM, 4 PM, and 11 PM. For a patient that prefers to sleep later than 7 AM, the administration times may be set to 9 AM, 5 PM, and 12 AM. Of course other frequency-types and administration schedules are possible. Another type of frequency may include set intervals, such as every 120 minutes, every 4 hours, etc. Set interval frequency types may be adjusted based on the time that the patient is awake, the time that a care provider would normally be administering medication locally to the patient, and the like. It may be important to note here the difference that exists in the two exemplary cases mentioned above, which is illustrated by the example that every 12 hours is not the same as twice per day where the day is defined as the waking hours of the patient. Therefore, the methods and systems described herein are able to take into account a particular treatment's Times of Administration ("TOA"), which typically varies across different treatments, patients, environments, and the like. In embodiments, a TOA pattern is determined based on observation of outcomes using the outcome module 120, in particular to determine the influence of different TOA patterns on patient outcomes for a particular medication given to patients of particular types over time.

Further, the dispensing and marking facility 104 may communicate the medication orders and the data associated with it to a medication dispensing machine. A medication dispensing machine may dispense and pack the medications. In an example the communication may be in HL 7 format. The medication dispensing machine may be similar to the dispensing, packaging, and bar coding systems currently commercially available, such as PEARSON MEDICAL'S iPACKT60 (TRADEMARK). Such machines are able to receive instructions regarding the medication to be dispensed, grouping of the dispensed medications, and labeling or marking of the packaging for the dispensed medications. Such machines also package the dispensed medications. Such packaging may include bar-coded pillow packs for the patient. Further the dispensing machine may be located remotely. The remote dispensing of prescriptions may be supported by automated dispensing machines such as in-facility kiosks, third party home delivery chains, and the like. The remote dispensing may include security to ensure proper authentication of the recipient through means like identifiers, passwords, finger scan, and the like.

Further, the medication dispensing machine may package the dosages according to instructions from the dispensing and marking facility 104, and is able to package the dosages according to data associated with the medication order; for example, information related to the patient's identity, the time of administration, the facility in which the patient resides or receives care, locations within the facility (such as wing, floor, room, and the like), patient insurance information, facility personnel associated/responsible for the patient, and administration frequency. The dosages may be packaged in packaging comprising human and barcode information regarding the particular dosage of medications. Different dosage of medications for the same patients may be grouped together in the same package resulting from instructions to associate a patient's medication by patient identifying information, the facility in which the patient resides or receives care, locations within the facility (such as wing, floor, room, and the like), patient insurance information, facility personnel associated/responsible with the patient, administration frequency, and the like.

Further the medications packaged for a single dose may be labeled with the barcode, which may be a conventional bar code or an advanced bar code, such as having graphical elements, human readable elements, holograms, 2D or 3D features, or the like. Identification information may also be embodied in a physical tag, such as an RFID tag, or a chip, such as used in a smart card, providing enhanced tracking functionality when coupled with an appropriate reader or scanner. Such RFID, chip and similar hardware embodiments should be understood as encompassed throughout this disclosure where barcodes and similar identifying marks are described herein. In an example, the single dose packages may be referred to as pillow packs. The barcode or other identifier may uniquely identify the patient, the prescription information, the medication to be administered, and general dosing rules and guidelines. The generation of this information may be automatic and may be assembled from information received at the prescription management facility 106, such as the information received from the prescribing facility 154. Further, the information may be prepared for use by the marking machine in the prescription management facility 106 and the information may include data received from the E-EHR/E-EMR facility 118. Further in an example, a pillow pack may be limited, such as to no more than, for example, three different medications so a patient may have more than one pillow pack for an administration of medication. The pillow packs may be prepared and/or delivered individually for each administration, for all administrations in one day, in a three or four day supply, in a 30, 60, 90 day supply, and the like. In one preferred embodiment, each administration of medication, as planned by a prescribed TOA pattern, is packaged into a single pillow pack or similar package, so that the probability of the patient selecting the wrong medication, or the wrong amount of medication, is reduced.

Further, the dispensing and marking facility 104 may communicate with a plurality of dispensing locations and signal the locations to dispense specific medications. The signaling to the locations may be based on a variety of factors including immediacy of the need for the medication, geographic proximity, availability and cost of transportation. The medication dispensing and marking facility 104 may further recognize the category and composition (liquid, solid, etc.) of the to-be-dispensed medication and route the dispensing to the appropriate dispensing mechanism. The labeling information may also be routed automatically to the appropriate marking system. Further, the HPDMA 100 may have the ability to keep track of the dispensed medications based on the proposed time of administration, patient details and location of the patient (e.g. in patient resident, day patient, emergency room, clinic, third-party facility, residential home, personal address, and the like). The information may be used to assist in the accurate and efficient packaging of the medications and treatments to be delivered to the correct location. Once delivered (as described below), the HPDMA 100 may have the ability to electronically read the information from the packages of medications and treatments and confirm receipt by the appropriate personnel at the designated location.

After the prescribed medication has been properly packaged and instructions have been marked on it, the dispensed medication may be sent for delivery. The RX delivery facility 108 may be utilized for delivering the dispensed medications. It should be noted that the portions of the computerized pharmacy services disclosed in co-pending U.S. Nonprovisional patent application having Ser. No. 10/134,293 filed Apr. 29, 2002 entitled CENTRALIZED PHARMACY BUSINESS METHOD (the disclosure of which is incorporated in its entirety herein by reference) may be utilized in providing orders to customer facilities. The HPDMA 100 may support loading the packaged prescriptions into medication carts. Carts may be associated with particular care facility location properties such as a particular facility, a floor in the facility, a wing of the facility, etc. In this way, the packaged dosages having the readable information thereon regarding the location of the patient, or the cart in which the dosage should be stored, provide for easy and efficient loading of the cart. The RX delivery facility 108 may also communicate in real-time with the backbone network 103 and may communicate the delivery details of the medication to other facilities of the HPDMA 100 via the backbone network 103.

Also, because the dosages are packaged according to the relevant associated data (as described above) rather than simply in a 30-day supply per drug per patient (as is the conventional case), the HPDMA 100 may allow users to select the duration of supply. In an example, the medications packaged according to the above disclosure may be provided in shorter supplies than the typical 30-day-supply. While the duration of supply could be of any time duration, supplies for two to ten days may result in significant cost savings by eliminating the amount of drugs that need to be returned or destroyed due to stopped or changed orders.

Further, the prescription management facility 106 may be in communication with an automated dispensing cabinet (ADC) on the premises of a healthcare facility. The HPDMA 100 may perform the functionality described above and may instruct the ADC to dispense drugs once released.

The prescription management facility 106 may perform similar functions as those described above, with the alternative or additional functionality of being able to provide healthcare facility professionals with the information necessary to dispense medication from their own medication stores. Thus there may be a medication storage device or automated dispensing cabinet ("ADC") on a healthcare facility's premises, and in addition to the facilities described above, a medication supply interface. The prescription management facility 106 may be in electronic communication with the medication supply interface, and may provide notification which may be output through the medication supply interface that the medication is approved for administration and whether the medication is in the medication storage device. The medication management facility 106 may be kept constantly up to date with regard to the inventory of the medication storage facility by the ordering and administration functions described herein.

The elements within the area 106 shown in FIG. 1 may be collectively referred to as a prescription management facility 106 and may include the RX validation and selection facility 102, the dispensing and marking facility 104 and the RX delivery facility 108. The prescription management facility 106 may include other facilities as well and may not be restricted to only these three facilities. The prescription management facility 106 may include or use an information technology infrastructure, such as including one or more software applications, data storage facilities, and the like that may be accessible via an electronic communication link, such as the Internet or other network, such as any type of network described herein.

Once the medication is delivered to the desired destination, it may be administered. The administration of the medication may be conducted at the prescription administration facility 110. The prescription administration facility 110 may facilitate proper administration and real-time data capture of prescription administration information. The prescription administration facility 110 may utilize technology-enabled devices such as handheld barcode scanners, smart card chip readers, RFID readers, hologram readers, or other devices, in certain preferred embodiments used in proximity to the patient at the point and time of administration, thereby increasing the probability that data about administration accurately reflects real events. Such devices may automatically read the coded information associated with the medication. Such devices may communicate with other portable computing devices such as smart phones, PDAs, laptop computers, or other devices having a facility to enter data. The portable computing devices and/or the scanners are in communication with each facility described herein in connection with FIG. 1. At the time of data collection, the use of handheld barcode scanners combined with contemporaneous entry of patient data (often prompted by the system at the time of scanning as will be described below) may allow real-time capturing of information about the events associated with and immediately after administering medications. The handheld barcode scanner may also allow obtaining of the real-time data and contextual information for the person performing the administration. In an exemplary case, the person performing the administration may be a patient, nurse, technician, physical therapist, or some other care provider. Further, the prescription administration facility 110 may access or communicate with a data center that may provide information from any of a variety of medical information related sources. Examples of data centers that provide relevant medical information may include E-EHR/E-EMR 118, outcome databases 124, third party databases 158, any of the facilities depicted in FIG. 1, and the like. In an exemplary case, such access may typically be through a wireless connection between a technology enabled device being used in association with administration 110 and a server or other networked device. Further, the prescription administration facility 110 may be communicatively coupled to the backbone network 103 and may communicate the administration details in real-time to the other facilities via the backbone network 103. The prescription administration facility 110 may include an integration facility for automatically integrating data that may be captured in context of prescription administration and that may be related to a medically-related event, healthcare related events, patient health condition data, patient physical activity data, patient treatment data, patient oral consumption data, patient visitor data, patient outcome data patient psychological data, patient vital signs, patient dietary and nutritional data, and the like for establishing or maintaining a patient's health record in association with the E-EHR/E-EMR facility 118. In an embodiment of the invention, the data captured in context of prescription administration may be referred to as medication administration data. The prescription administration facility 110 may also prompt a user of the technology enabled prescription administration facility 110 device to enter (into the portable computing device or the scanner for example) information associated with administration of the dosages of medication and also to verify that a dosage has been administered to the patient.

In an embodiment of the invention, the medication administration data from the prescription administration facility 110 may be raw medication administration data. The raw medication administration data may not be in a format that may be integrated with the E-EHR/E-EMR facility 118. The prescription administration facility 110 may include a computer (not shown in the FIG. 1) that may transform the raw medication administration data to a format such that it may be integrated with the patient's EHR in the E-EHR/E-EMR facility 118.

Further, the prescription administration facility 110 may facilitate providing bedside prescription administration that may further facilitate capturing all caregiver observations and clinical events performed as part of the prescription administration. The data associated with the caregiver observations and clinical events performed may be captured in real-time at the bedside as described above or may be captured later from notes taken or entered into the system by the caregiver. Further, because the information is collected at the bedside the prescription administration facility 110 may collect information that may not directly relate to the prescription administration activity. Such information may alternatively be obtained by the patient attribute and events facility 112. The information may be collected using sensors. In an example the sensor may be an accelerometer or motion detector that detects patient movements, such as standing, walking, and the like. As will be described elsewhere herein, the information may further be utilized to populate an E-EHR/E-EMR facility 118 in real-time.

Further, in an embodiment of the invention, the medication administration facility 110 may include a sensor that may detect opening of a pillow pack of the medication or a bottle of the medication or any other container containing the medication. In an embodiment of the invention, the sensor may be able to identify the geo-location of the medication package at the time the medication package is opened. Further, the detected location may be recorded in the E-EHR/E-EMR facility 118. In an embodiment of the invention, the information about the detected location may be transmitted by the sensor over a wireless network. In an example, the wireless network may be a WiFi network. In another embodiment of the invention, the information about the detected location may be communicated through near field communication to a handheld scanning device being used in the medication administration events. In yet another embodiment of the invention, the information about the detected location may be communicated through near field communication to a mobile device being used in the medication administration event. Further in embodiments of the invention, the information about the location of the medication package at the time the medication package is opened may also be recorded manually at the time of administering that medication to the patient.

The bedside administration may further allow collecting data associated with elderly patients and patients in LTC. This data may include, without any limitations, psychiatric and psychologically relevant observations, along with physical data. In an example, when an elderly patient has undergone a heart surgery, the elderly patients tend to go into depression or display symptoms of psychosis that may be caused by or exacerbated by an administered medication. As the HPDMA 100 allows bedside data collection of prescription administration and treatment of the patient, the data related to the mental state of the elderly patient or the patient in the LTC may only be relevant if they are recorded by observing the patient a significant amount of the time to allow observation of changes. Further, this data may be recorded in the electronic health record of the patient by the E-EHR/E-EMR facility 118. Further, this data may be used as early indications of a related condition of depression or psychosis and may facilitate the prescription of additional medication or assigning of other therapies known to prevent deterioration in the nascent symptoms. In embodiments, the psychological observations may be associated with TOA information, so that patterns in psychological effects of medication administration can be observed and tracked, such as using outcome module 120.

Further, at the time of administration, the administering professional using the HPDMA 100 may scan the medication barcodes, which may populate various fields in the administration facility 110 that may be displayed on a screen by or on the administration facility 110 for verification and/or manual completion. Alternatively, or in conjunction with the scanning, data that may relate to the patient, care facility, care giver, environment, observations, and the like as well as data relating to the administration may be entered into the administration facility 110, such as through a user interface. In an embodiment of the invention, the handheld scanner scanning the medication barcodes or other health monitoring devices providing the patient's health condition data may generate a location data corresponding to the medication that is being administered to the patient. In an embodiment of the invention, the location data may be generated by utilizing the Global Positioning System (GPS) facility embedded in the handheld scanner or other monitoring devices. Once the information is entered, and prior to administration, the information is communicated to the medication management facility 106. If current information in the medication management facility 106 shows that there has been a change to the patient's medication, a stop order, or the like, may be communicated to the administration facility 110 and displayed via the interface on the technology enabled administration device to the prescription administrator. In this way, the HPDMA 100 may prevent the administration of discontinued medications and ensure that the correct medication and dosage is being administered at the right time. The HPDMA 100 might require the caregiver to uniquely identify themselves using a plurality of identification methodologies. The collected identification information may be validated, recorded, and stored to ensure compliance with regulations and provide tracking information for the caregiver that administered the treatments or care.

Further, the prescription administration facility 110 may include a therapeutic equivalent facility which may accept electronic medication orders and suggest therapeutic equivalents. Drug products classified as therapeutically equivalent may be substituted with the full expectation that the substituted product may produce the same clinical effect and safety profile as the prescribed product. Drug products may be considered to be therapeutically equivalent if they meet criteria such as: they are pharmaceutical equivalents (contain the same active ingredient(s); dosage form and route of administration; and strength.); they are assigned by FDA the same therapeutic equivalence codes starting with the letter "A" To receive a letter "A", the FDA designates a brand name drug or a generic drug to be the Reference Listed Drug (RLD), and assigns therapeutic equivalence codes based on data that a drug sponsor submits in an Abbreviated New Drug Application to scientifically demonstrate that its product is bioequivalent (i.e., performs in the same manner as the Reference Listed Drug). The therapeutic equivalent facility may contain a library of such therapeutic equivalents and suggest them to the prescribing professional upon order entry based on, for example, whether the proscribed medication is on the patient's insurance formulary.

Further the HPDMA 100 may utilize the patient's information including, but not limited to, age, sex, medical condition, current diagnoses, and past medication history to guide the caregiver in administering medication. Such information may, in various embodiments, be provided with security to render it anonymous, such as for compliance with regulatory requirements relating to patient privacy.

The prescription administration facility 110 and the prescription management facility 106 may allow capturing of the information about the medications that may be prescribed but not administered. Such cases may occur when a medication is prescribed but the prescription is not filled, or when the prescription has been filled in the pharmacy, but then the caregiver decides not to administer that medication or the patient declines to take the medication. The reasons for not administering the medication may include, without any limitations, that patient feels better and does not require the medication, that the patient identifies that the side effect of the medication is too risky and hence declines the medication, that the caregiver decides on a different medication, or the like. For example, if side effects of the medication include an upset stomach, and the patient already has an upset stomach, the caregiver may conclude it does not want to exacerbate that side effect with medication.

Further, once the medication is dispensed and the doctor or the physician determines that a different medication is required for the patient, some of the original medication goes unused. In such a case, the status of the unused portion of the used medication gets updated in real-time in E-EHR facility 118. The insurance and payments facility 138 may obtain the information associated with unused medication from the E-EHR facility 118 to revise the billing accordingly. The pharmacy inventory status may also be updated with information regarding the unused medication and the unused medication may be returned back to the pharmacy or destroyed. The medications for a patient in LTC or other in-patient care facility may be dispensed from the pharmacy for one dose at a time to avoid wasted medication or handling medications that may be returned to the pharmacy. Thus, in certain preferred embodiments the HPDMA 100 may track non-administered medication, such as for outcome tracking, payment/reimbursement, and other purposes.

The HPDMA 100 may further include the patient attributes and events facility 112. The patient attributes and events facility 112 may monitor change in patient's attributes in response to the prescribed medication. These changes may be communicated to other facilities via the backbone network 103. The patient attributes and events facility 112 may further track the events associated with the patient after consuming the prescribed medication. These events may be communicated in real-time to the other facilities via the backbone network 103. Further, the changes in the events and attributes of the patient may correspond to treatment outcomes. Further the patient attributes and events facility 112 may obtain the information collected at the bedside by the prescription administration facility 110. This information may include, without any limitation, on what side the patient is lying, how many times the patient has turned his side, the position of the patient, changes in the position of the patient, changes in the body position of the patient, changes in the movement of the patient, whether the patient is walking or standing or sitting or sleeping, what the patient ate or consumed, whether the patient sleeping or awake, how much did the patient eat, how much did the patient drink, how much did the patient excrete and the like. The information may further be associated with the caregiver and may include, without any limitations, changing or dressing the bandages of the patient, and the like. The monitoring of the patient's attributes and events may provide various types of data including, but not limited to, patient health condition data, patient physical activity data, patient treatment data, patient outcome data, patient psychological data and the like. Further, the various types of data may be recorded by the E-EHR/E-EMR facility 118.

In an embodiment of the invention, the various types of data from the patient attributes and events facility 112 may be raw format and may include raw patient health condition data, raw patient physical activity data, raw patient treatment data, raw patient outcome data and raw patient psychological data. The raw format of the various types of data may not be in a format that may be integrated with the E-EHR/E-EMR facility 118. The patient attributes and events facility 112 may include a computer (not shown in the FIG. 1) that may transform the raw format of the various types of data to a format such that it may be integrated with the patient's EHR in the E-EHR/E-EMR facility 118.

The outcome events facility 114 may then obtain the outcomes of the patient's attributes and the events. The outcome events facility 114 may store the obtained treatment outcomes and may also communicate them in real-time to the other facilities of the HPDMA 100 via the backbone network 103.

Further, the medical event streams on the backbone network 103, from different facilities of the HPDMA 100, may be utilized to populate the E-EHR/E-EMR facility 118. The medical event stream may include outcomes from prescription management events, healthcare planning events, laboratory events, medical payment events and treatment outcome events.

The E-EHR facility 118 may be associated with other facilities as depicted in FIG. 1 and may exchange information (e.g. real-time data) with these facilities. The E-EHR facility 118 may maintain a collection of health records of an individual and/or a group of individuals in a format that may be capable of being shared across different medical facilities of the HPDMA 100 or with external facilities. In an exemplary case, the health records may be shared electronically through the Internet and the like. Further, an E-EHR may include any related medical data and information, such as medical history, allergies, pathology and laboratory test results, medical scanning reports, region and residential information, psychological data, and the like.

Further, the E-EHR facility 118 may encompass information related to all the facilities of the HPDMA 100 including administrative, nursing, lab, clinical, radiology, pharmacy, care planning, imaging, insurance planning, facility planning, rehabilitation, and the like. An electronic communication interface may be provided for implementing receipt information by the E-EHR facility 118 from the backbone network 103 and providing the information from the E-EHR facility. Such an electronic interface may thereby facilitate utilization of the E-EHR related information anywhere within the HPDMA 100. For example, lab reports of a patient stored in an E-EHR facility 118 may be utilized during care planning to prepare a healthcare plan for a patient. Similarly, patient data related to allergies and sensitivities may be utilized by a doctor to prescribe relevant medicines and offer treatment accordingly. Further, an E-EMR may be generated in association with the E-EHR facility 118 and may be useful in an institution such as a hospital, clinic, physician's office, nursing home/center and the like.

Once the data from the medical event streams on the backbone network 103 has been stored in the E-EHR/E-EMR facility 118, the medical data may be utilized by various other facilities of the HPDMA 100. The outcome facility 120 may obtain the treatment outcome events from the E-EHR/E-EMR facility 118. The outcome facility 120 may utilize the electronic interface of the E-EHR/E-EMR facility 118 to obtain the treatment outcome data. Further, the outcome facility 120 may have a bidirectional communication with the E-EHR/E-EMR facility 118.

The E-EHR/E-EMR facility 118 may also be coupled to the existing medical record facility 122. The existing medical record facility 122 may include hard copy and/or a database that may store the existing medical records of a patient or a group of patients.

The outcome database facility 124 may be communicatively coupled to the outcome facility 120 to obtain the treatments and outcomes for the medication being administered to the patients. The outcome database facility 124 may include a plurality of databases that may store the treatments and outcomes data for a plurality of similar patients. The outcome database facility 124 may also be communicatively coupled to the backbone network 103 and may obtain treatments and outcomes data in real-time. Further, the outcome database facility 124 may communicate the treatment outcomes of the patient to other facilities of the HPDMA 100 through the backbone network 103.

Further, the outcome database facility 124 may be coupled to the outcome analytics facility 128 that may utilize the treatment outcomes of the patient to generate medical reports, medical predictions and other medical analyses. The outcome analytics facility 128 may utilize the demographic information associated with the patient, information regarding the administration of the medication and clinical outcomes, and the like to generate the reports, predictions and other analyses. The administration information may include the time of administration and the dose of medication. The output of the outcome analytics facility may be utilized by other facilities of the HPDMA 100. Further the outcome analytics facility may access the third party data 158 to produce the reports and predictions. Third-party data may include medical studies, trials, FDA related data, orange book data, and the like.

Further, the outcome data may be utilized to determine the condition of the patient's health, adverse event for a particular drug, sampling of patients with an infectious disease, monitoring of patient flow during an epidemic, outcome of a clinical test, and correlation of disease in case the clinical test is found to be positive or some other kind of outcome related to healthcare data. In this aspect, the outcome analytics facility 128 may include an analytic workbench facility that may provide different modules for conducting statistical analysis of the outcome data. Such an analytic workbench facility may implement one or more statistical techniques including, but not limited to, Analysis of Variance (ANOVA), Chi-square test, Correlation, Factor analysis, Mann-Whitney U, Mean square weighted deviation (MSWD), Pearson product-moment correlation coefficient, Regression analysis, Spearman's rank correlation coefficient, Student's t-test, Time series analysis, Bootstrap & Jackknife Resampling, Statistical classification, Statistical surveys, Structured data analysis (statistics), Survival analysis, Multivariate discriminant analysis, Linear discriminant analysis, Cluster analysis, Principal component analysis, and the like.

By leveraging the real-time bed-side data collection capabilities of the HPDMA 100 along with support for accessing a plurality of enhanced electronic health records, the outcome facilities (e.g. outcome facility 120, outcome database facility 124 and, outcome analytics facility 128) may facilitate rapidly detecting an onset of an epidemic type situation. By combining outcome analysis 128 with real-time data it may be possible to identify patients infected with an infectious disease at the first screening. For example, the various symptoms of an epidemic-type disease may be stored in the outcomes database and a patient's real-time symptoms may be captured and entered into the outcome analytics facility 128 (e.g. analytics workbench) to facilitate identifying a patient with such a disease. Likewise, the analysis capabilities of the analytic workbench may support regression analysis to facilitate determining genetic modification of a virus over a period.

Similarly, real-time event data may be associated with the outcome. The analytic workbench facility may perform statistical analysis to determine whether the occurrence of a specific event is significant to the outcome data. A feedback may be provided to the associated medical specialist, in case the event is statistical and significant to a specific patient. The analytic workbench facility may be programmed to dynamically select the best algorithm in a specific situation. Alternatively, the analytic workbench facility may include a GUI enabling the user to select the algorithm to be applied.

In association with the outcome analytics facility 128, various machine learning techniques may be implemented using neural networks to improve on the analytics as well as to facilitate predicting outcomes. Various types of neural networks may be employed including learning algorithms, reinforcement-learning algorithms, supervised learning algorithms, and unsupervised learning algorithms. Further, other techniques include genetic algorithms, biological cybernetics, biologically inspired computing, cerebella model articulation controllers, cognitive architecture, cultured neuronal networks, neural network software, neuro-fuzzy approaches, neuroscience, predictive analytics, radial basis function networks, recurrent neural networks, self-organizing maps, simulated reality, hidden markov models, kalman filters, decision theory, support vector machines, tensor product networks, time adaptive self-organizing maps, time delay neural networks and the like.

Additionally, the analytic workbench facility may utilize learning to train suitable techniques for optimum prediction. The prediction of a future outcome based in part on an earlier outcome may be an integral part of the analytic workbench facility. In this regard, the analytic workbench facility may extrapolate data to identify future events associated with the patient and raise an alert to doctors about these future events. For example, outcomes for a plurality of patients experiencing a range of symptoms who have been administered a drug may be used to predict an outcome of a patient with similar symptoms who may be prescribed a similar drug. This predicted outcome may include certain side effects that can be prevented with proper preventive treatment. Even if these side effects were not present in the FDA trials before the drug was allowed on the market, the analysis of outcomes combined with other information collected by the HPDMA 100 may facilitate predicting these outcomes in patients.

The machine learning techniques may utilize algorithms that may perform various data mining operations on the data such as classification, clustering and other data mining techniques known in the art. To this end, the effect of various drugs on a particular disease may be studied, and an identification relating to the effect of the drug may be recorded. For example, brand X may cause fewer side effects, when administered to children, than brand Y. Likewise, in another example, brand Y may be more effective in critical conditions. These analyses may help doctors and other medical staff to create a knowledge map for treatment under different conditions.

Machine learning may be performed by taking into account a weight that reinforces a particular outcome. An initial set of weights may be determined based on, for example, a prediction, theory, hypothesis, or the like as to the importance of a particular factor or factors, then adjusted by feeding actual outcomes into the machine learning system. For example, the machine learning may initially append a weight X if the drug is believed to be suitable, then adjust the weight based on actual outcomes as tracked in the outcome module 120. Likewise, if the administered drug cures the patient slowly and subsequently allows the patient to recover completely, a higher weight (XX) may be assigned by the machine learning algorithm. Similarly, if an administered drug results in quick recovery then a much higher weight (XXX) may be assigned to the medication and/or treatment by the machine learning algorithm. In an emergency situation, the doctors may use outcome prediction based on machine-learning techniques employed in the outcome analytics facility 128 to confirm an initial diagnosis that may have been made by a field emergency medical technician. In certain preferred embodiments weights will be multivariate, such as taking into account the medication, the TOA pattern for the medication, clinical treatment factors, psychological observations, and the like. Similarly, the outcomes that are fed into the machine learning system may vary, such as including extent and timing of recovery, mitigation or exacerbation of side effects, financial factors, observation of satisfaction or psychological factors, and the like.

Further, clinical outcomes of the medication may be measured using indicators like, but not limited to, disease control, risk reduction, and health care analysis of the patient undergoing treatment. Clinical outcomes of a medication may also be measured using monetary terms by analyzing the economical perspective of the medication. The method for measuring clinical outcomes in monetary terms may include: a) determining the most appropriate clinical outcome of the medication; b) establishing monetary investment on achieving the most appropriate clinical outcome, and thereafter, calculating a financial value for the most appropriate clinical outcome as per the monetary investment for the medication.

The above calculated financial value may be an indicator of the cost-benefit analysis of the medication. The financial value may be calculated for a drug, treatments, a medical facility, a health-care management solution, a disease reduction program, and the like.

The financial value may be employed as an indicator for ranking a medication, a drug, treatments, a medical facility, a health-care management solution, a disease reduction program, and the like. For example, there may be more than one effective medication that may be used to treat a set of diagnosed symptoms; one of these may be more expensive than the other but equally beneficial with regard to alleviating symptoms of the patient. In this scenario, the financial value may determine the selection of the medicine in order to provide the best clinical outcome for the dollars spent.

Other factors may be combined with the cost of medication to arrive at the most effective financial outcome in offering treatment. For instance, factors such as a pharmacy management information system, the prescription management facility 106, the insurance and payments facility 138, and the like, may be combined to arrive at numerous alternative pharmacy management features. The insurance company may select a specific pharmacy management feature to reimburse the hospital or patient in the management of a particular disease. Validation of an RX may include the rating of the medication prescribed and that rating may influence the rate of reimbursement that may be dispensed by the insurance company. For instance, one pharmacy management feature may include an RX with various factors such as expensive medications and additional therapies such as alternative medicine and psychotherapy that may be incidental to the patient's recovery; another pharmacy management feature may include other factors that include less expensive but efficacious medications and only those therapies such as physiotherapy, drug therapy and occupational therapy that may be most essential to the patient's recovery. In such a scenario, the insurance company may have the option of preferring to pay for the RX that it considers most suitable for treating the patient and, based on validation of the RX, it may prefer to reimburse cost of the latter line of treatment and reject the former.

Further, the output of the outcome analytics facility 128 may be utilized by the rehabilitation and LTC facility 130 to plan a long term care or the rehabilitation treatment for the patient. This planning may be based on the different parameters such as background needs of the patient, medical equipment needs, home healthcare environment needs, nutrition, supply, commodities, education & training, and the like. These parameters may be obtained from the reports and the predictions made by the outcome analytics facility 128. Further the rehabilitation and LTC facility 130 may obtain real-time medical event streams from the backbone network 103. The rehabilitation and LTC facility 130 may also communicate its events to other facilities via the backbone network 103. Further, the E-EHR/E-EMR facility 118 may store the event outcomes from the rehabilitation and LTC facility 130, thus creating the enhanced or enriched version of an E-EHR.

Another embodiment of the invention may provide real-time data regarding aspects of a long term health care facilities' prescription and administration of drugs. The HPDMA 100 may include a real-time reporting facility which is configured to store data related to any one of the identities of the patients, the identities of the personnel who care for or are responsible for the patient, medications prescribed, medications that were returned or destroyed, costs associated with medications that were not covered or only partially covered by a payer, costs associated with medications for which the health care facility had to pay, and the like. The real-time reporting facility may associate any of the above parameters with any other of the above parameters. The real-time reporting facility may also provide up-to-the-minute and time-based summary information regarding the above parameters and any of the related parameters. Such information may be presented to a user via the workstation, for example, with text, graphics, charts, and the like.

The output of the outcome analytics facility 128 may be utilized by the third party integration facility 132. A third party integration facility 132 may facilitate the use of third party tools, such as payment management tools, data quality tools, research tools, language translation tools, data normalization tools, and the like in association with the HDPMA 100 facilities, methods, and systems depicted in an described in relation to FIG. 1 and other figures herein.

The labs and imaging facility 134 may also utilize the predictions and reports associated with the patients from the outcome analytics facility 128 to conduct diagnostic tests on the patients. The labs and imaging facility 134 may further communicate the laboratory outcomes for the patient to other facilities of the HPDMA 100 and these outcomes may further populate the E-EHR/E-EMR facility 118.

The reports and predictions from the outcome analytics facility 128 may further be utilized by the insurance and payments facility 138 to prepare billing reports for the patient. The reports and predictions from the outcome analytics facility 128 may include details about the medications administrated to the patient. These details may be utilized by the insurance and payments facility 138 to identify the reimbursement and the non reimbursement medications. The insurance and payments facility 138 facility may further communicate these billing details over the backbone network and these details may be utilized by the other facilities of the HPDMA 100.

The output of the outcome analytics facility 128 may further be utilized by the regulatory facility 140. The regulatory facility 140 may be involved in planning and decision making for improving and meeting compliance, addressing existing deficiencies in the processes, reducing business risks, and the like.

The output of the outcome analytics facility 128 may further be utilized by the pharmacy planning facility 142. In an exemplary case, the output of the outcome analytics facility 128 may reveal that many people suffer from a side effect, e.g., stomach infection, after taking a particular medication (and in embodiments, such information is collected by prescription administration facility as described herein). In light of this observation, the pharmacy planning facility 142 may change the prescription instructions. In extension to this, the pharmacy planning facility 142 may also include devising methods and processes to make this information public by means of improving product packaging through print and electronic media, and the like. The pharmacy planning facility 142 may further include development of a medication that is easier to digest or development of a medication that may suppress the side effects of the previous drug.

The output of the outcome analytics facility 128 may further be utilized by the facility planning facility 144. In an exemplary case, the output may include the ratio of inpatient and outpatient services, older and critically sick patient population, treatment patterns, advancement in technology, health data related to diseases and conditions (asthma, cholesterol, diabetes, heart disease, hypertension, obesity, etc.), type of healthcare (ambulatory services, ER visits, etc.), data related to injuries (accidents, suicides, homicides, etc.), life stages and population (births, deaths, women's health, children's health, state and territorial distribution, etc.), lifestyle (drug use, smoking, exercise, etc.), and the like. Further, a long term care center or a facility may provide rehabilitative, restorative, and/or ongoing skilled nursing care to patients or residents in need of assistance with activities of daily living. This facility planning may require specific consideration and design than the facility planning for a general healthcare center since it may cater to the needs of a specific group (e.g., elderly or homeless) that are otherwise not able to get focused healthcare and attention. Examples of long-term care facilities may include nursing homes, rehabilitation facilities, inpatient behavioral health facilities, long-term chronic care hospitals, and the like. Long term care facilities may be designed to make them safe, functional, durable and relatively easy to maintain. Some parameters to be considered while designing long term care facilities may include design, layout, ambience, color management, dining and food management, online and kiosk-based layouts, ease of access for the handicapped and the like. For example, the facilities may be designed to include automatic ID scanners for residents using the dining facility; it may also be designed to facilitate easy movement for a patient confined to a wheelchair.

The output of the outcome analytics facility 128 may further be utilized by the insurance planning facility 148.

The planning by the insurance planning facility 148 may be done regarding coinsurance options, i.e., the amount that is required to be paid for medical care in a fee-for-service plan after meeting the deductibles. Further, the planning may also be performed regarding the suitability and selection of insurance plans based on the requirements of an individual. Examples of various plans may include basic plans, Health maintenance (HMOs), Preferred Provider Organizations (PPOs), Points of Service (POS), and the like. Other aspects that may be significant for insurance planning may include information on customary fee, exclusions, maximum out-of-pocket expenses, non-cancellation cases, premium, and the like.

The output of the outcome analytics facility 128 may further be utilized by the dashboard facility 150 to generate different kinds of reports and to allow medical-related personnel to interact with the facilities and/or data available through the HPDMA 100. In an exemplary case, the dashboard facility may provide a specialist dashboard, a clinical outcome dashboard, a Long Term Health Care (LTC) administrator dashboard, a LTC facility specific dashboard, a pharmacist dashboard, various planning dashboards, prescription management dashboards, and the like. Each dashboard may have different looks that may be represented by data entry or display fields or tabs. The dashboards may be populated in real-time with the data from any of the facilities depicted in FIG. 1 including the E-HER facility 118. Further, the dashboard facility 150 may be communicatively coupled to the backbone network 103 to allow real-time updating of an onscreen display of a dashboard with information collected in real-time (e.g. medication administration or patient event data).

The output of the outcome analytics facility 128 may further be utilized by the care planning facility 152. Care planning may include the planning of any aspect of patient care and may be based at least in part on data provided by an E-EHR/E-EMR 118, actual outcomes 124, predicted outcomes, and other analytics provided by the outcomes analytics facility 128. A physical rehabilitation facility manager may adjust a schedule of care takers and rehabilitation specialists based on the outcomes or predicted outcomes for patients being treated in regional hospitals. A nurse may be notified that a patient on her shift has recently started a medication that, based on an outcome prediction, will make the person thirsty, so that the nurse can ensure that the patient has plenty of fluids available. These are only examples of a few potential care planning facility 152 features and therefore are not representative of all of the features of the care planning facility 152.

Figure 2:
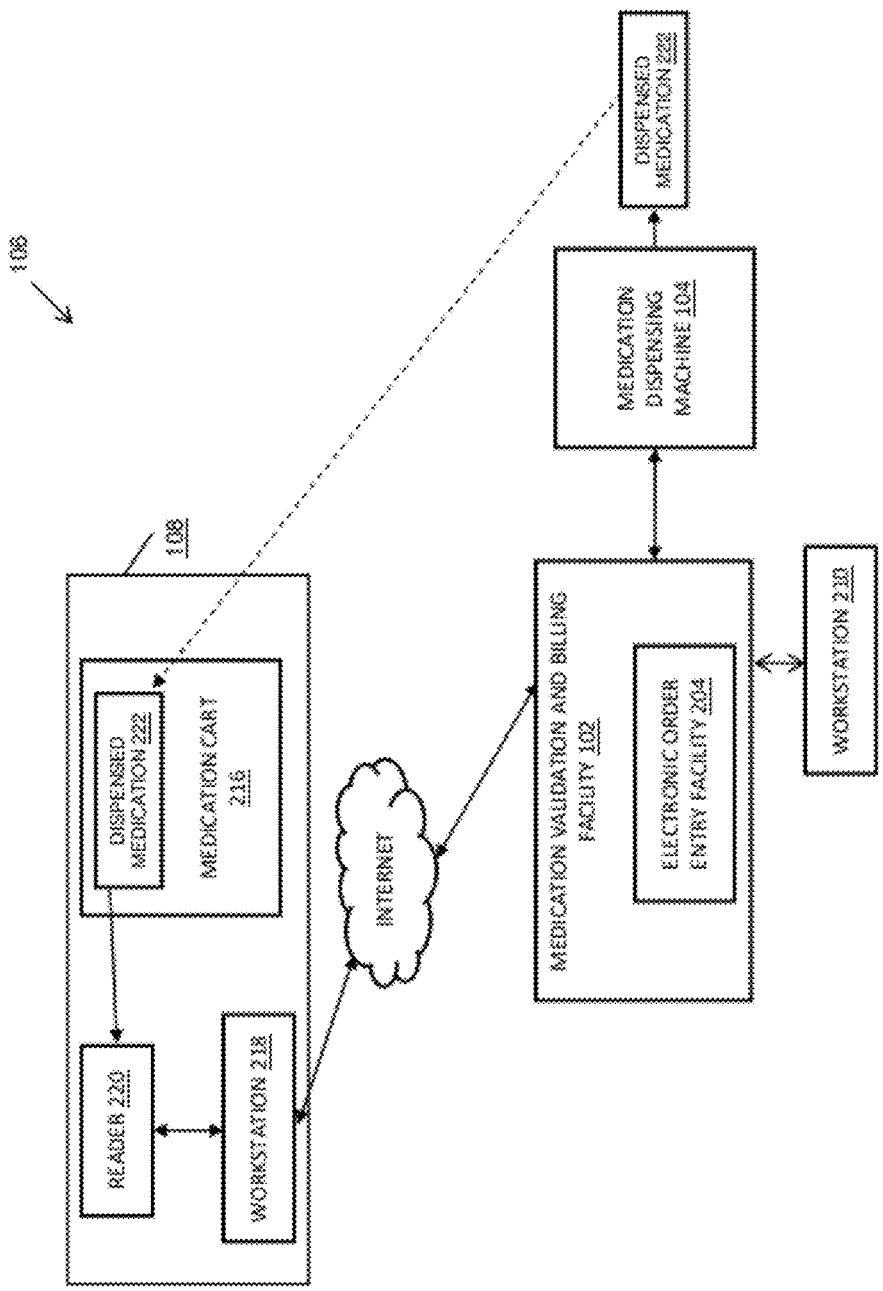
FIG. 2 depicts a block diagram of a portion of the HPDMA.

FIG. 2 is a detailed schematic depiction of an exemplary embodiment of medication management facility 106. The medication management facility 106 may include a medication validation and billing facility 102 and an electronic order entry facility 204 accessible by a validation workstation 210 and coupled to a medication dispensing machine 104 that may generate patient and dose specific packaged medication 222. The medication management facility 106 may also include a medication or RX delivery facility 108 that may include a medication cart 216 on which the dispense medication 222 may be arranged so that it can be read by an id reader 220 that may communicate directly or through a workstation 218 with the medication validation and billing facility 102, such as through the Internet.

As with all facilities described herein, some of the facilities depicted in FIG. 2 may be embodied as physical devices (e.g. computers, machines, carts, packaged medicine, scanners, and the like), and some may be embodied as either software or a combination of software and hardware. In an example, electronic order facility 204, medication validation and billing facility 102 may be embodied as one or more software applications executing on a processor, such as a web server that is in communication with the other devices as depicted in FIG. 2.

The electronic order entry facility 204 may include a user interface for aiding a health specialist to enter electronic medication orders and other prescription-type orders. The user interface may be displayed on the validation workstation 210, a prescribing facility 154 (as shown in FIG. 1), any other electronic communication device (e.g. a mobile phone, a hand-held prescription entry device, and the like). The medication validation facility 102 may use security-type identification methods to uniquely identify, record, and document the person entering the orders. As described herein, the medication validation and billing facility 102 may be configured to facilitate verifying formulary compliance of the ordered medication(s), determining drug allergy information associated with the prescribed drugs, confirming the drug interaction information associated with the entered electronic medication orders, and other prescription validation, inventory compliance checks, billing compliance checks, and the like. On the basis of any of these or other validation checks performed by the facility 102, a signal may be sent to the source (e.g. a workstation, etc) of the electronic medication order to warn the prescriber on a patient-by-patient basis. Such warnings may need to be resolved before accepting the order.

To facilitate compliance with pharmacy regulations and generally support a high degree of quality control, a user interface accessible on the validation workstation 210 may include a utility that may allow a pharmacist to approve the electronic medication orders after having reviewed all the relevant information. The approval of the electronic medication orders may also herein be referred to as releasing the orders. Further, the medication validation and billing facility 102 may associate relevant data to the released orders, such as patient identifying information, the facility in which the patient resides or receives care, locations within the facility (such as wing, floor, room, etc.), patient insurance information, facility personnel associated/responsible for the patient, administration frequency, and the like. The information regarding the patient may be received either electronically via interfaces to other systems (e.g. as depicted in FIG. 1) or via manual input (e.g. through a user interface of the validation workstation 210).

After the medication order has been approved, the medication validation and billing facility 102 may communicate the released orders and the data associated therewith to a medication dispensing machine 104. In an example, the communication between the medication validation and billing facility 102, and the medication dispensing machine 104 may be in HL7 format. The medication dispensing machine 104 may also receive instructions regarding the medications to be dispensed, how to group the dispensed medications, and how to label the packaging of the dispensed medications 222. On the basis of the received instructions, the medication dispensing machine 104 may package the medications into individually packaged dosages. The medication dispensing machine 104 may also package the dosages according to data associated with the order, for example, information related to the patient's identity, the time of administration, the facility in which the patient resides or receives care, locations within the facility (such as wing, floor, room, etc.), patient insurance information, facility personnel associated/responsible for the patient, administration frequency, medication cart number, and the like. The dosages may be packaged in packaging comprising human and electronically readable information regarding the particular dosage of medications. Electronically readable information could, in embodiments, be bar-coded, although any other traceable marking or device may be employed (RFID, 2D code, matrix code, and the like). In an example, the medication dispensing machine 104 may package bar-coded pillow packs for the patient. Further, different dosages of medications for the same patients could be grouped together in the same package resulting from instructions to associate a patient's medication by patient identifying information, the facility in which the patient resides or receives care, locations within the facility (such as wing, floor, room, etc.), patient insurance information, facility personnel associated/responsible with the patient, administration frequency, and the like.

Further in an embodiment of the invention, the dispensed medications 222 may be packaged and transported to a health care facility that may be local to the dispensing machine 104 or may be remotely located. The dispensed medications 222 may be transported (e.g. on a medication cart 216 into which the packaged medication dosages may be loaded) from the dispensing machine 104 to a health care facility. In an example, the health care facility may receive a plurality of medication carts 216, each of which may be associated with a particular location in the facility such as a particular facility, a floor in the facility, a wing of the facility, etc. In this way, the packaged dosages having readable information thereon that describe the intended location of the patient or the cart in which the dosage should be stored, may provide for easy and efficient loading of a medication cart 216. The dispensed medicine 222 may be automatically loaded onto one of the medication cards 216 that may be located near the dispensing machine 104. Alternatively, the dispensed medication 222 may be transported in bulk to a distribution location (e.g. a nurse's station or an in-house pharmacy) and loaded onto a medication card 216 manually.

To facilitate management of medications stored on a medication cart 216, a reader 220 and a medication workstation 218 may be used in the processing of medicine cart-based dispensed medications 222. One or more user interfaces displayed on the medication workstation 218 may support various work flow processes associated with medication dispensing, transport, delivery, and the like. The reader 220 and medication workstation 218 may be used at any of a variety of events (e.g. as defined by the work flows) associated with the sorting, distribution, transport, delivery, unpacking, administration, and disposal of dispensed medications 222. In an example of remote sorting and medication cart 216 loading, a person may use a code reader to capture a marked code on a pillow pack of medication and select a medication cart loading work flow. The captured data may be transmitted (e.g. over the internet) to the medication validation and billing facility 102 where it may be used to lookup medication cart 216 loading instructions that may then be sent back to the medication workstation 218 to be used by the person loading the medication cart 216. In an example of dispensed medication 222 being transported in the medication cart 216, a person may scan a label on the medication cart 222 and select a transportation work flow. The scanned data may be communicated to the validation and billing facility 102 which may respond with specific facility floor and wing information that may be displayed on the medication workstation 218. The person may use the displayed location information to forward the medication cart 216. Upon arrival of the medication card 216 at the designated floor/wing, a person (e.g. a nurse) may scan the label on the cart 216 again to signify that the cart 216 has been received. Further in the example, to begin delivering the individual medication dosages to patients on the wing, a nurse may scan the cart 216 label and select a final delivery workflow on the medication workstation 218. Although the exemplary embodiments described above include specific communications with the medication validation and billing facility 102, some or all of these communications may be changed to support batch information transfer. For example, when the medication cart 216 is loaded near the medication dispensing machine 104, a batch of data representing the loaded cart 216 may be sent to medication workstation 218 to facilitate autonomous handling of the loaded cart 216 at the selected destination (e.g. long term care facility). Other combinations of real-time and batched communications are possible and are included herein.

Figure 3:
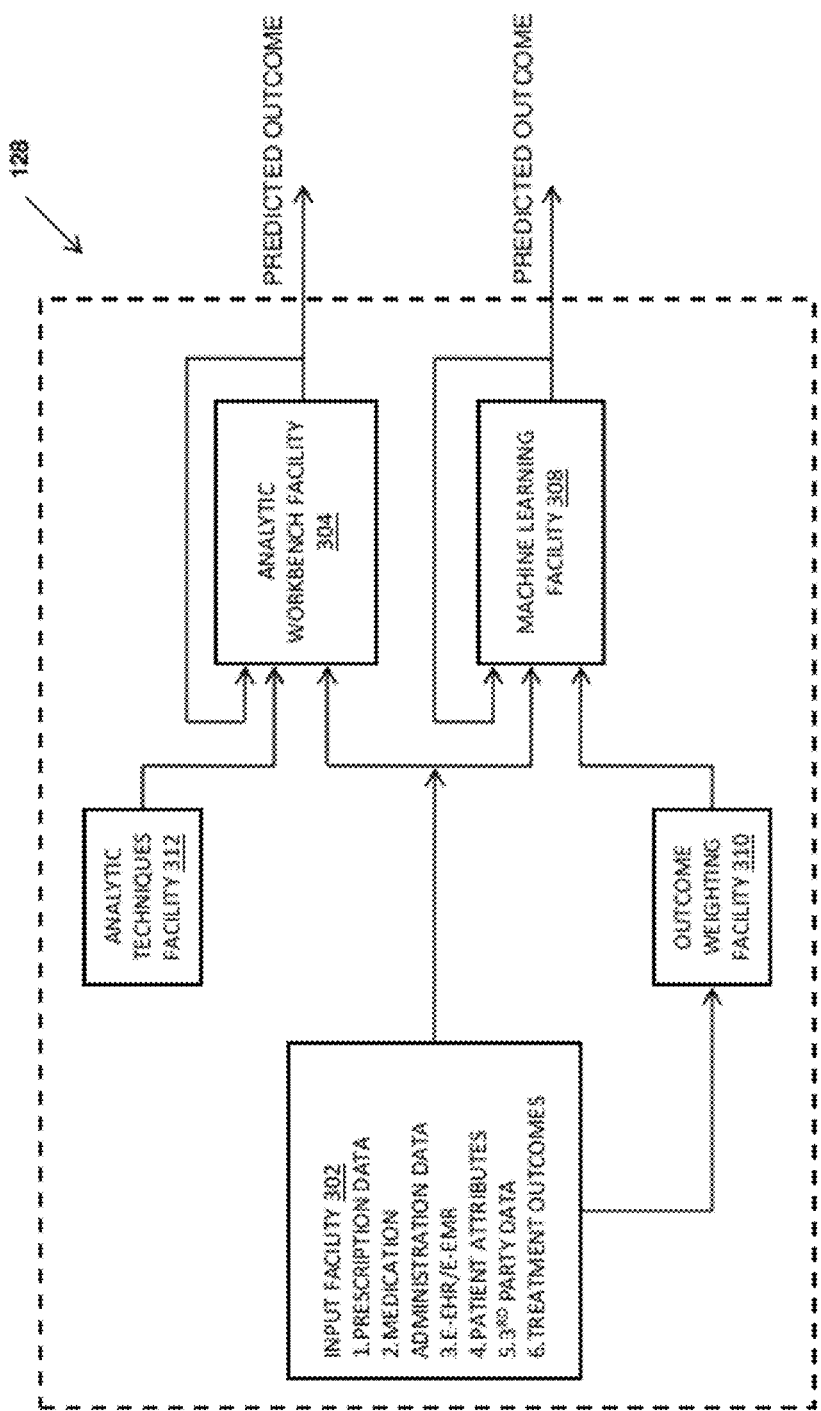
FIG. 3 depicts a block diagram of another portion of the HPDMA.

FIG. 3 depicts a detailed diagrammatic view of an exemplary embodiment of the outcome analytics facility 128, in accordance with an embodiment of the invention. The outcome analytics facility 128 may be utilized to determine the condition of the patient's health, adverse event for a particular drug, sampling of patients with an infectious disease, monitoring of patient flow during an epidemic, outcome of a clinical test, correlation of disease in case the clinical test is found to be positive or some other kind of outcome related to healthcare data, and many other types of outcome analytics. Results of the outcome analytics facility 128 may be used by other facilities as depicted in FIG. 1 and its accompanying descriptions.

The outcome analytics facility 128 may include an input facility 302, an analytic workbench facility 304, a machine learning facility 308, and an outcome weighting facility 310, and an analytics technique facility 312. The input facility 302 may facilitate receiving a variety of different types of outcome data to be analyzed, such as data from the outcome databases 124, the third party databases 158, and the like. Data that may be processed by the outcome analytics facility 128 may include prescription data, medication administration data, E-EHR/E-EMR data, data associated with patient's attributes, third party data, treatment outcomes and the like. The input facility 302 may provide some initial data processing to normalize data and/or otherwise transform it to be suitable for further analysis by the analytic workbench facility 304, the machine learning facility 308, and/or the outcome weighting facility 310. Further, the input facility 302 may provide data provided to the analytics facility 128 to analytics processing facilities that may include the analytic workbench facility 304 or the machine learning facility 308. For example, the input facility 302 may provide a training data set to the machine learning facility 308 for training the machine learning facility 308. In another example, the input facility 302 may optionally direct received outcome data to an outcome weighting facility 310.

In an embodiment of the invention, the analytic workbench facility 304 may predict an outcome of a medically-related event by implementing one or more statistical techniques obtained from the analytic technique facility 312. The analytic technique facility 312 may include, without any limitation, regression analysis, iterative analysis, complex modeling, multivariable analytics, Analysis of Variance (ANOVA), Chi-square test, Correlation, Factor analysis, Mann-Whitney U, Mean square weighted deviation (MSWD), Pearson product-moment correlation coefficient, Regression analysis, Spearman's rank correlation coefficient, Student's t-test, Time series analysis, Bootstrap & Jackknife Resampling, Statistical classification, Statistical surveys, Structured data analysis (statistics), Survival analysis, Multivariate discriminant analysis, Linear discriminant analysis, Cluster analysis, Principal component analysis, and the like. Depending on the type of prediction or analysis function that is to be performed by the analytics facility 128, one or more of these techniques may be selected for use by the analytics engine. The analytic techniques facility 312 may be a database of algorithms that may be accessible to the analytics engine facility 304.

Similarly, real time event data may be associated with the outcome. The analytic workbench facility 304 may perform statistical analysis to determine whether the occurrence of a specific event is significant to the outcome data. Feedback may be provided from the analytics facility 128 to a caregiver in case the event is statistical and significant to a specific patient. In another embodiment, the analytic workbench facility 304 may include a feedback loop that may be utilized for correcting the output and/or the outcome. For example, the data provided to the analytics engine facility 304 may have missing data; the missing data may be fitted accordingly to the standard techniques known in the art. In addition, the output may be fed back into the analytics engine facility 304 for correcting the deviation of output to the actual output; for example, degeneration of virus may follow a Poisson's distribution rather than exponential distribution.

Further, the analytic workbench facility 304 may be programmed to dynamically select the best algorithm in a specific situation. Alternatively, the analytic workbench facility 304 may include a GUI enabling the user to select the algorithm to be applied. Additionally, the analytic workbench facility 304 may utilize the previous learning to train in suitable techniques for optimum prediction. In an embodiment, the prediction of the future event based on the earlier event may be an integral part of the analytic workbench facility 304. In this regard, the analytic workbench facility 304 may extrapolate data to identify future events associated with the patient and raise an alert to doctors about these future events. For example, administration of aspirin may reduce the phenomena of clotting in a patient; however, because of an emergency, the drug (aspirin) may be administered to the patient. In this scenario, the analytic workbench facility 304 may alert the medical staff about the possible reduction in clotting of blood. The doctor operating upon this patient may be informed in advance in order to take remedial action.

In another embodiment of the invention, a machine learning facility 308 may be implemented using neural networks to produce the predicted outcomes. Various types of neural networks may be employed including learning algorithms, reinforcement-learning algorithms, supervised learning algorithms, and unsupervised learning algorithms. Further, other techniques include genetic algorithm, biological cybernetics, biologically inspired computing, cerebella model articulation controller, cognitive architecture, cultured neuronal networks, neural network software, neurofuzzy, neuroscience, predictive analytics, radial basis function network, recurrent neural networks, self-organizing map, simulated reality, hidden markov model, kalman filter, decision theory, support vector machine, tensor product network, time adaptive self-organizing map, time delay neural network and the like.

Further, the machine learning facility 308 may be used to perform various data mining operations on the data such as classification, clustering and other data mining techniques known in the art. To this end, the effect of various drugs on a particular disease may be studied, and an identification relating to the effect of the drug may be recorded. For example, brand X may cause fewer side effects, when administered to children, than brand Y. Likewise, in another example, brand Y may be more effective in critical conditions. These analyses may help doctors and other medical staff to create a knowledge map for treatment under different conditions.

In an embodiment, machine learning may be performed by taking into account a weight from an outcome weighting facility 310 that reinforces a particular result. For example, the machine learning facility 308 may apply a weight X in an outcome prediction if a drug associated with the prediction is found to be suitable. Likewise, if the administered drug cures the patient slowly and subsequently allows the patient to recover completely, a higher weight (XX) may be assigned to the outcome in the machine learning algorithm. Similarly, if an administered drug results in quick recovery then a much higher weight (XXX) may be assigned to the outcome in the machine learning algorithm. In an embodiment, both the analytics engine facility 304 and the machine learning facility 308 may be simultaneously utilized for predicting the outcome of the input data. For example, the input data may be first passed to the analytics engine facility 304 and subsequently to the machine learning facility 308 for determining the predicted data. In another example, the input data may be first passed to the machine learning facility 308 and subsequently to the analytics engine facility 304 for determining the predicted data.

In another embodiment, a feedback loop may be provided in association with the machine learning facility 308 to reintroduce a part of the predicted outcome data back into the machine learning facility 308. In this scenario, the feedback loop may either be a positive feedback or a negative feedback, reinforcing the outcome in the first case and damping the outcome in the latter case. In another embodiment, the machine learning may be in the form of weighted feedback and the weights introduced in the feedback loop may determine the outcome of the predicted data.

Figure 4:
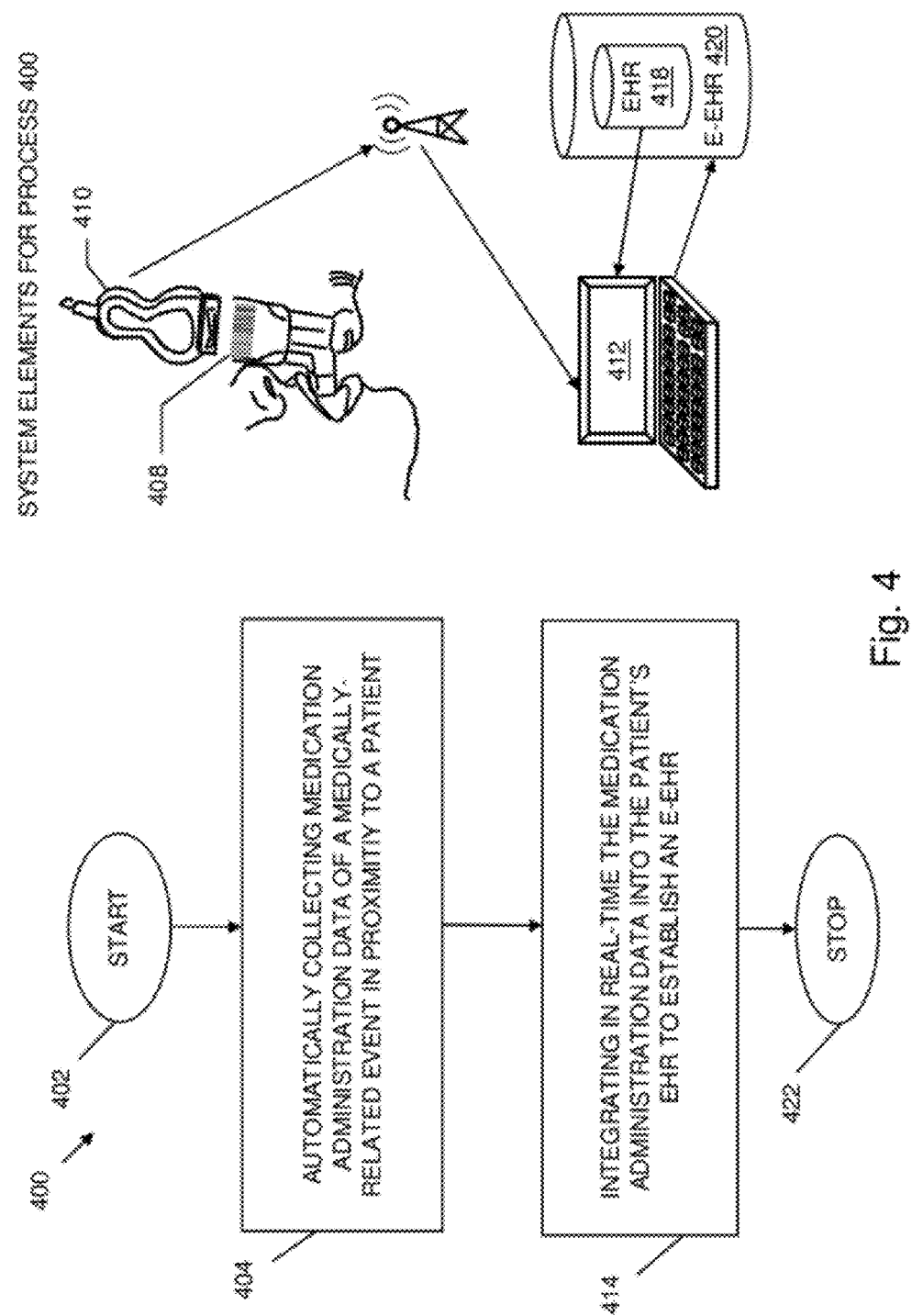
FIG. 4 depicts a flow chart and exemplary structural elements of a bed-side process of establishing an enhanced electronic health record.

FIG. 4 illustrates a process and system 400 for automatically establishing an Enhanced Electronic Health Report (E-EHR) with medication administration data of a medically-related event that is automatically collected in real-time in proximity to a patient, in accordance with an embodiment of the invention. The process begins at step 402. At step 404, medication administration data 408 of the medically-related event associated with the patient may be collected. The step 404 of collecting the medication administration data 408 of the medically-related event may be accomplished by an automatic data collection facility in proximity to the patient such as those described herein. In embodiments, the automatic data collection facility may be a machine reader. In an embodiment of the invention, the machine reader may be a handheld barcode reader facility 410. The handheld barcode reader facility 410 may read the barcodes on the packaging of a dosage of medication and may be in electronic communication with the prescription administration facility (not shown in the FIG. 4). The medication administration data 408 may be raw medication identification data that may be transformed to be suitable or used with a medication information database, or it may include the medication, time of administration, dosage, reaction data, and administration of a dosage of medication.

As described herein, additional data about the medically-related event (which in embodiments may be the medication administration data 408) may be fed into a computer 412. As an example, a caregiver might scan the coded information on a medication packet to initiate the process 400. The coded information may be automatically read by the automatic data collection facility. The medication administration facility (110 in FIG. 1) may also prompt the user to enter other relevant data about the patient's current condition at the time of medication administration, which in embodiments such input may be into the automatic data collection facility or into one of the various smartphones, computing devices, etc. in electronic communication with the automatic data collection facility and/or other facilities disclosed in connection with FIG. 1.

After the medication administration data 408 of the medically-related event associated with the patient has been collected at step 404, the handheld barcode reader facility 410 may communicate via an electronic communication, the collected medication administration data 408, to the computer 412, which may represent any of the facilities depicted in FIG. 1 (e.g. prescription management facility 106, prescribing facility 154, outcome database module 124, and the like). In an embodiment of the invention, the electronic communication may be the Internet. Thereafter, at step 414 the medication administration data 408 and other information may be integrated automatically in real-time with the patient's EHR 418 to establish the E-EHR 420 of the patient. The step 414 of integrating the medication administration data 408 and other information may be accomplished by using the computer 412. The step 414 may further include using the computer 412 to transform the raw medication administration data so that it can be integrated with the patient's EHR. The process ends at step 422.

Figure 5:
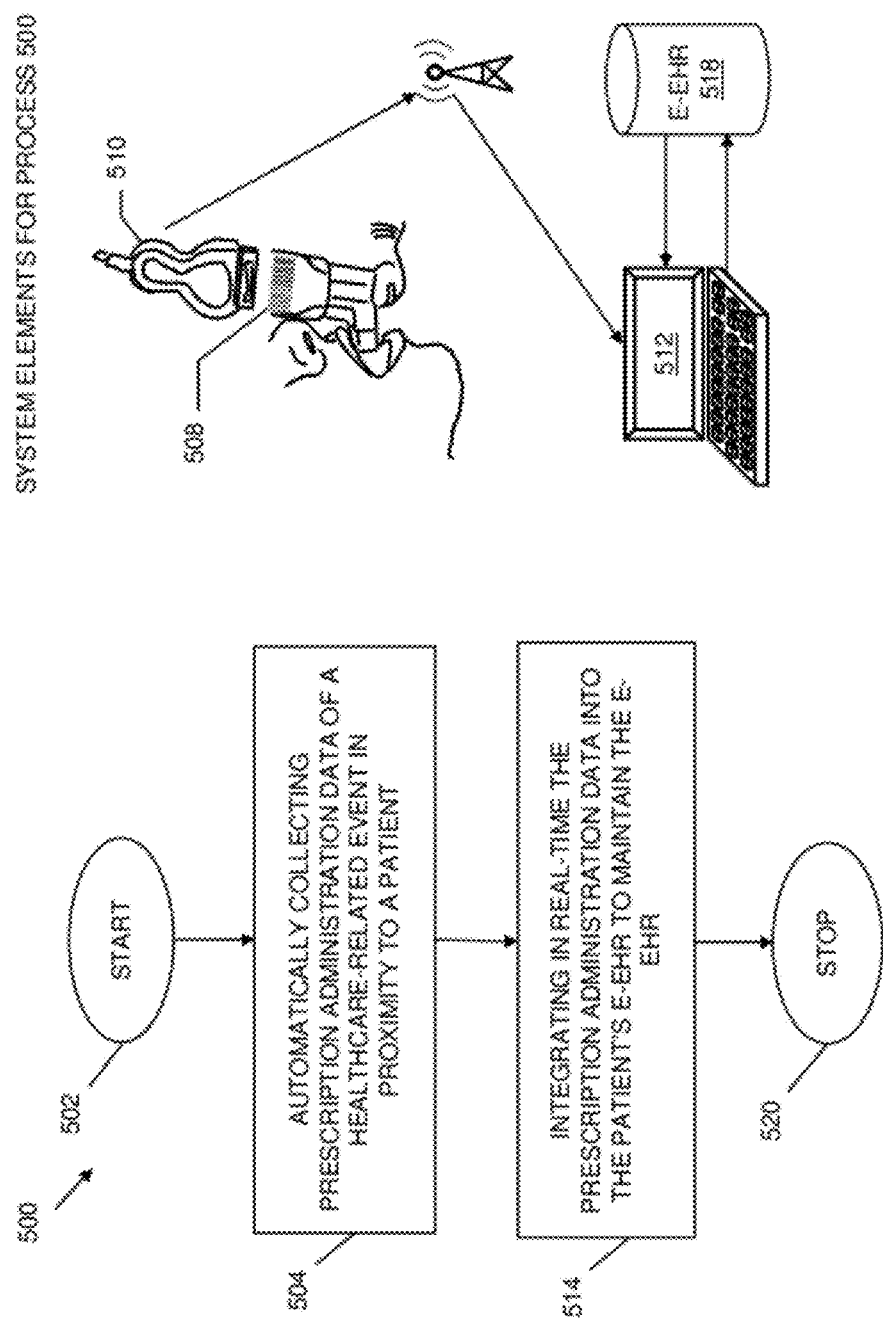
FIG. 5 depicts a flow chart and exemplary structural elements of a bed-side process of maintaining an enhanced electronic health record.

FIG. 5 illustrates a process and system 500 for automatically maintaining an E-EHR with prescription administration data of a healthcare-related event that is automatically collected in real-time in proximity to a patient, in accordance with an embodiment of the invention. The process begins at step 502. At step 504, the prescription administration data 508 of a healthcare-related event associated with a patient may be collected. The step 504 of collecting the prescription administration data 508 of the medically-related event may be accomplished by an automatic data collection facility in proximity to the patient such as those described herein. In embodiments, the automatic data collection facility may be a machine reader. In an embodiment of the invention, the machine reader may be a handheld barcode reader facility 510. The barcode reader facility 510 may read the barcodes on the packaging of the dosage of medication and may be in electronic communication with the prescription administration facility (not shown in the FIG. 6). Further, the prescription administration data 508 may be raw prescription administration data that may be transformed to be suitable or used with a medication information database.

As described herein, additional data about the medically-related event (which in embodiments may be the prescription administration data 508) may be fed into a computer 512. As an example, a caregiver might scan the coded information on a medication packet to initiate the process 500. The coded information may be automatically read by the automatic data collection facility. The medication administration facility (110 in FIG. 1) may also prompt the user to enter other relevant data about the patient's current condition at the time of medication administration.

After the prescription administration data 508 of the medically-related event associated with the patient has been collected at step 504, the handheld barcode reader facility 510 may communicate via an electronic communication, the collected prescription administration data 508, to the computer 512 which may represent any of the facilities depicted in FIG. 1 (e.g. prescription management facility 106, prescribing facility 154, outcome database module 124, and the like). In an embodiment of the invention, the electronic communication may be the Internet. Thereafter, at step 514 the prescription administration data 508 and other information may be integrated automatically in real-time with the patient's E-EHR facility 518 to maintain the E-EHR facility 518. The step 514 of integrating the prescription administration data 508 and other information may be accomplished by using the computer 512. The step 514 may further include using the computer 512 to transform the raw prescription administration data 508 so that it can be integrated with the patient's EHR. The process ends at step 520.

Figure 6:
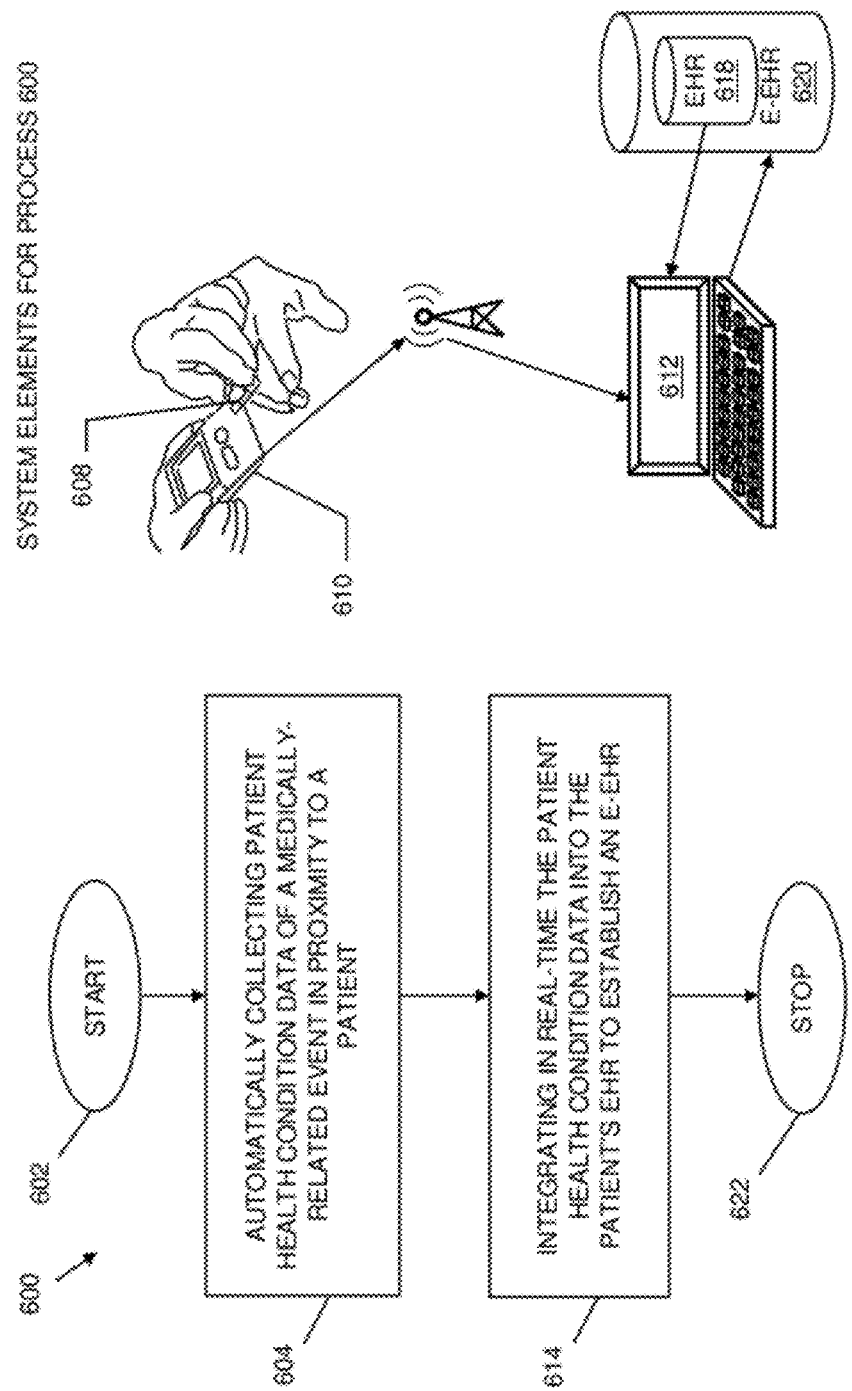
FIG. 6 depicts a flow chart and exemplary structural elements of a bed-side process of collecting patient health condition data to establish a enhanced electronic health record.

FIG. 6 illustrates a process and system 600 for automatically establishing an E-EHR with patient health condition data of a medically-related event that is automatically collected in real-time in proximity to a patient, in accordance with an embodiment of the invention. The process begins at step 602. At step 604, patient health condition data 608 of the medically-related event associated with the patient may be collected. The step 604 of collecting the patient health condition data 608 of the medically-related event may be accomplished by an automatic data collection facility in proximity to the patient such as those described herein. In embodiments, the automatic data collection facility may be a health condition monitor. In an embodiment of the invention, the health condition monitor may be a handheld blood glucose monitoring facility 610. The handheld blood glucose meter facility 610 may monitor the blood glucose level associated with patient and may be in electronic communication with the prescription administration facility (not shown in the FIG. 6). The patient health condition data 608 may be raw health condition data that may be transformed to be suitable or used with a medication information database, or it may include patient vital signs, patient blood chemistry results, and the like.

As described herein, additional data about the medically-related event (which in embodiments may be the patient health condition data 608) may be fed into a computer 612. As an example, a caregiver might monitor the blood glucose level associated with the patient by using the handheld blood glucose monitoring facility 610 to initiate the process 600. The monitored information may be automatically read by the automatic data collection facility. The medication administration facility (110 in FIG. 1) may also prompt the user to enter other relevant data about the patient's current condition at the time of medication administration.

After the patient health condition data 608 of the medically-related event associated with the patient has been collected at step 604, the handheld blood glucose monitoring facility 610 may communicate via an electronic communication, the collected patient health condition data 608, to the computer 612 which may represent any of the facilities depicted in FIG. 1 (e.g. prescription management facility 106, prescribing facility 154, outcome database module 124, and the like). In an embodiment of the invention, the electronic communication may be the Internet. Thereafter, at step 614 the patient health condition data 608 and other information may be integrated automatically in real-time with the patient's EHR facility 618 to establish the E-EHR facility 620 of the patient. The step 614 of integrating the patient health condition data 608 and other information may be accomplished by using the computer 612. The step 614 may further include using the computer 612 to transform the raw health condition data so that it can be integrated with the patient's EHR. The process ends at step 622.

Figure 7:
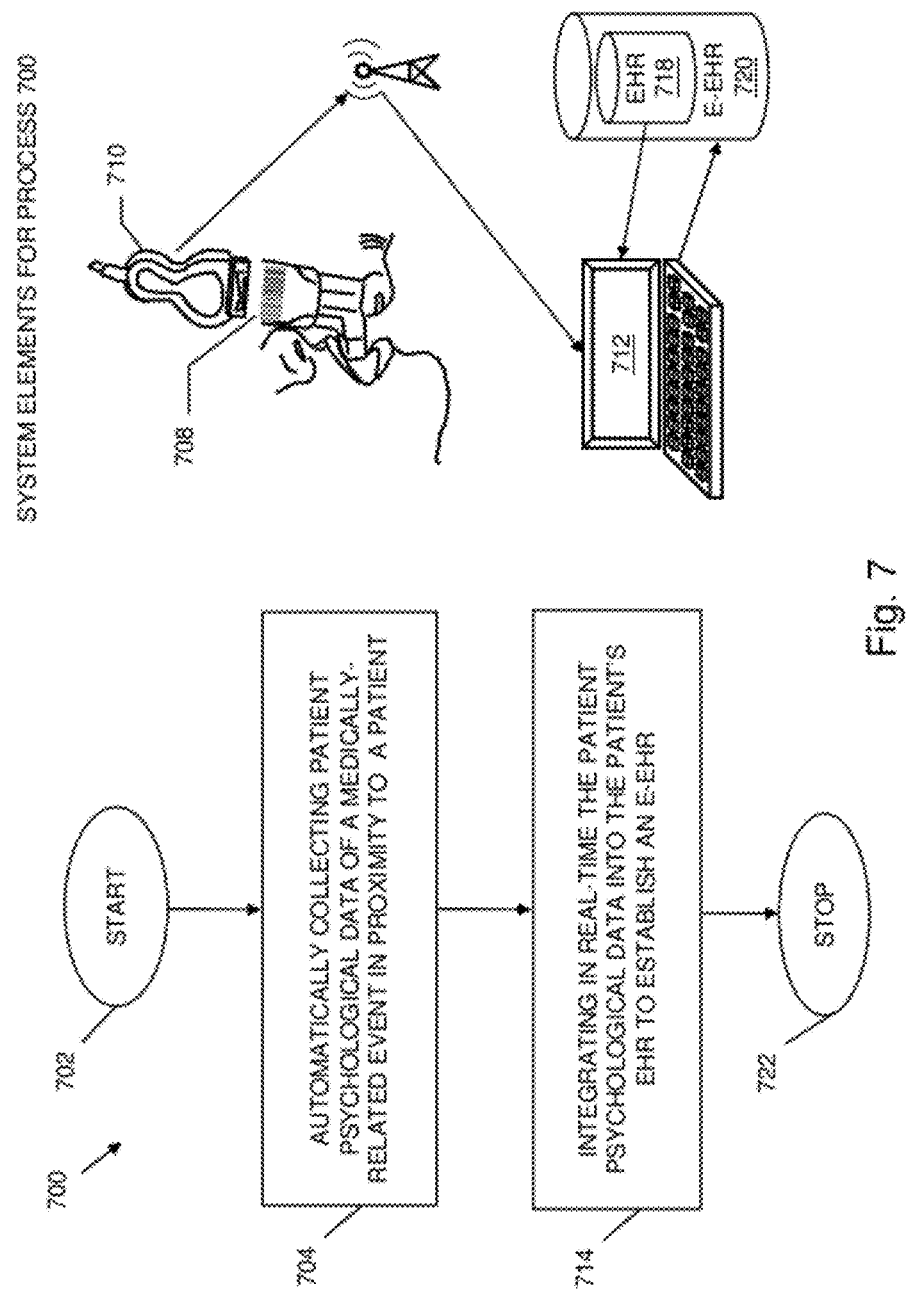
FIG. 7 depicts a flow chart and exemplary structural elements of a bed-side process of collecting patient psychological data associated with a medically-related event to establish a enhanced electronic health record.

FIG. 7 illustrates a process and system 700 for automatically establishing an E-EHR with patient psychological data of a medically-related event that is automatically collected in real-time in proximity to a patient, in accordance with an embodiment of the invention. The process begins at step 702. At step 704, the patient psychological data 708 of the medically-related event associated with the patient may be collected. The step 704 of collecting the patient outcome data 708 of the medically-related event may be accomplished by an automatic data collection facility in proximity to the patient such as those described herein. In embodiments, the patient psychological data 708 may be collected upon observation of an occurrence of the medically-relevant event. Further, the automatic data collection facility may be a machine reader. In an embodiment of the invention, the machine reader may be a handheld barcode reader facility 710. The handheld barcode reader facility 710 may read the barcodes on the packaging of a dosage of medication and may be in electronic communication with the prescription administration facility (not shown in the FIG. 7). Further, the patient psychological data 708 may be raw psychological data that may be transformed to be suitable or used with a medication information database.

As described herein, additional data about the medically-related event (which in embodiments may be the patient psychological data 708) may be fed into a computer 712. As an example, a caregiver might scan the coded information on a medication packet to initiate the process 700. The coded information may be automatically read by the automatic data collection facility. The medication administration facility (110 in FIG. 1) may also prompt the user to enter other relevant data about the patient's current condition at the time of medication administration.

After the patient psychological data 708 of the medically-related event associated with the patient has been collected at step 704, the handheld barcode reader facility 710 may communicate via an electronic communication, the collected patient psychological data 708, to the computer 712 which may represent any of the facilities depicted in FIG. 1 (e.g. prescription management facility 106, prescribing facility 154, outcome database module 124, and the like). In an embodiment of the invention, the electronic communication may be the Internet. Thereafter, at step 714 the patient psychological data 708 and other information may be integrated automatically with real-time into the patient's EHR facility 718 to establish the E-EHR facility 720 of the patient. The step 714 of integrating the patient psychological data 708 and other information may be accomplished by using the computer 712. The step 714 may further include using the computer 712 to transform the raw psychological data so that it can be integrated with the patient's EHR. The process ends at step 722.

Figure 8:
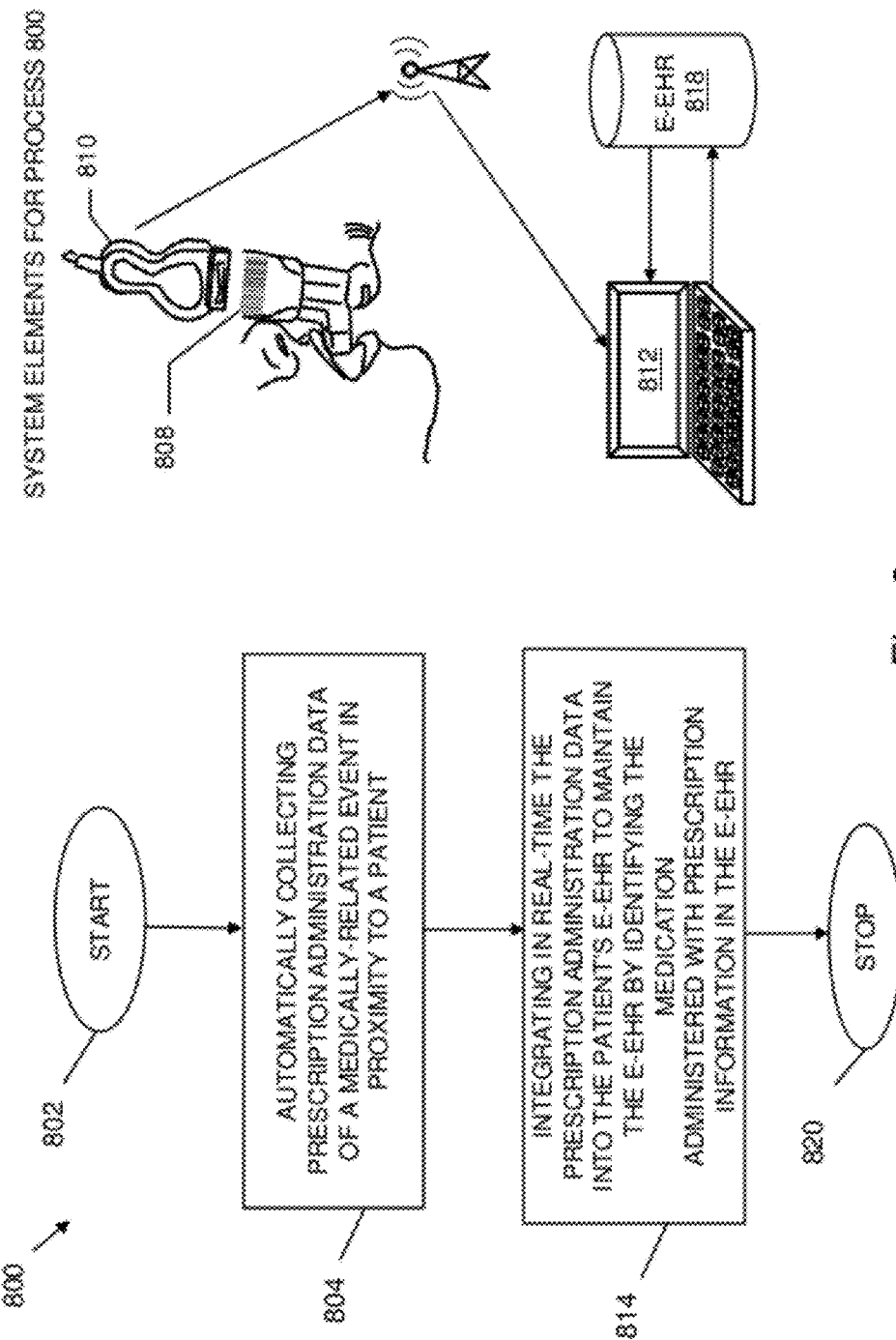
FIG. 8 depicts a flow chart and exemplary structural elements of a bed-side process of identifying medication based on an enhanced electronic health record.

FIG. 8 illustrates a process and system 800 for automatically maintaining an E-EHR with administration data of a prescription for a patient that is collected during a medically-related event automatically and in real-time while in proximity to the patient. The process begins at step 802. At step 804, prescription administration data 808 related to the medically-related event associated with the patient may be collected. The step 804 of collecting the prescription administration data 808 of the medically-related event may be accomplished by an automatic data collection facility in proximity to the patient such as those described herein. In embodiments, the prescription administration data 808 may be collected upon observation of an occurrence of the medically-relevant event. Further, the prescription administration data 808 may be identifiable by the prescription management data in patient's EHR. Further, the automatic data collection facility may be a machine reader. In an embodiment of the invention, the machine reader may be a handheld barcode reader facility 810. The handheld barcode reader facility 810 may read the barcodes on the packaging of a dosage of medication and may be in electronic communication with the prescription administration facility (not shown in the FIG. 8). Further, the prescription administration data 808 may be raw prescription administration data that may be transformed to be suitable or used with a medication information database.

As described herein, additional data about the medically-related event (which in embodiments may be the prescription administration data 808) may be fed into a computer 812. As an example, a caregiver might scan the coded information on a medication packet to initiate the process 800. The coded information may be automatically read by the automatic data collection facility. The medication administration facility (110 in FIG. 1) may also prompt the user to enter other relevant data about the patient's current condition at the time of medication administration.

After the prescription administration data 808 of the medically-related event associated with the patient has been collected at step 804, the handheld barcode reader facility 810 may communicate via an electronic communication, the collected prescription administration data 808, to the computer 812 which may represent any of the facilities depicted in FIG. 1 (e.g. prescription management facility 106, prescribing facility 154, outcome database module 124, and the like). In an embodiment of the invention, the electronic communication may be the Internet. Thereafter, at step 814 the prescription administration data 808 and other information may be integrated automatically with real-time into the patient's E-EHR facility 818 to maintain the E-EHR facility 810. The step 814 of integrating the prescription administration data 808 and other information may be accomplished by using the computer 814. The step 814 may further include using the computer 812 to transform the raw prescription administration data so that it can be integrated with the patient's E-EHR facility 818. The process ends at step 820.

Figure 9:
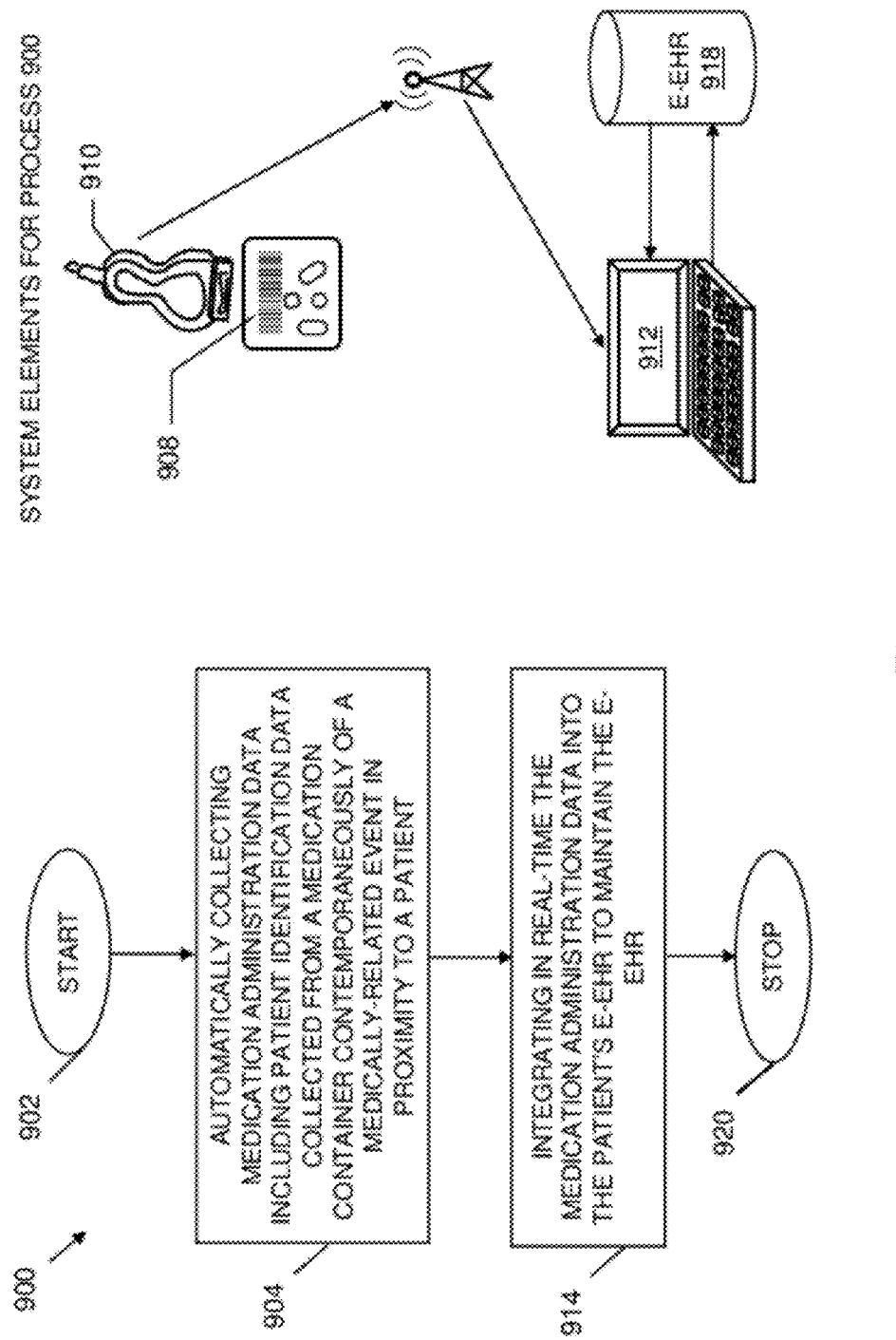
FIG. 9 depicts a flow chart and exemplary structural elements of a bed-side process of collecting medication information in association with a medically-related event.

FIG. 9 illustrates a process and system 900 for automatically maintaining an E-EHR with medication administration data that includes patient identification data of a medically-related event that is automatically collected in real-time in proximity to a patient, in accordance with an embodiment of the invention. The process begins at step 902. At step 904, medication administration data 908 of the medically-related event associated with the patient may be collected. The step 904 of collecting the medication administration data 908 of the medically-related event may be accomplished by an automatic data collection facility in proximity to the patient such as those described herein. In embodiments, the automatic data collection facility may be a machine reader. In an embodiment of the invention, the machine reader may be a handheld barcode reader facility 910. The handheld barcode reader facility 910 may read the barcodes on the packaging of a dosage of medication and may be in electronic communication with the prescription administration facility (not shown in the FIG. 9). The medication administration data 908 may be raw medication identification data that may be transformed to be suitable or used with a medication information database, or it may include patient identification data that may be collected from a medication container contemporaneously with the medically-related event.

As described herein, additional data about the medically-related event (which in embodiments may be the medication administration data 908) may be fed into a computer 912. As an example, a caregiver might scan the coded information on a medication packet to initiate the process 900. The coded information may be automatically read by the automatic data collection facility. The medication administration facility (110 in FIG. 1) may also prompt the user to enter other relevant data about the patient's current condition at the time of medication administration.

After the medication administration data 908 of the medically-related event associated with the patient has been collected at step 904, the handheld barcode reader facility 910 may communicate via an electronic communication, the collected medication administration data 908, to the computer 912 which may represent any of the facilities depicted in FIG. 1 (e.g. prescription management facility 106, prescribing facility 154, outcome database module 124, and the like). In an embodiment of the invention, the electronic communication may be the Internet. Thereafter, at step 914 the medication administration data 908 and other information may be integrated automatically in real time with the patient's E-EHR 918 to maintain the E-EHR 918 of the patient. The step 914 of integrating the medication administration data 908 and other information may be accomplished by using the computer 912. The step 914 may further include using the computer 912 to transform the raw medication administration data so that it can be integrated with the patient's EHR. The process terminates at step 920.

Figure 10:
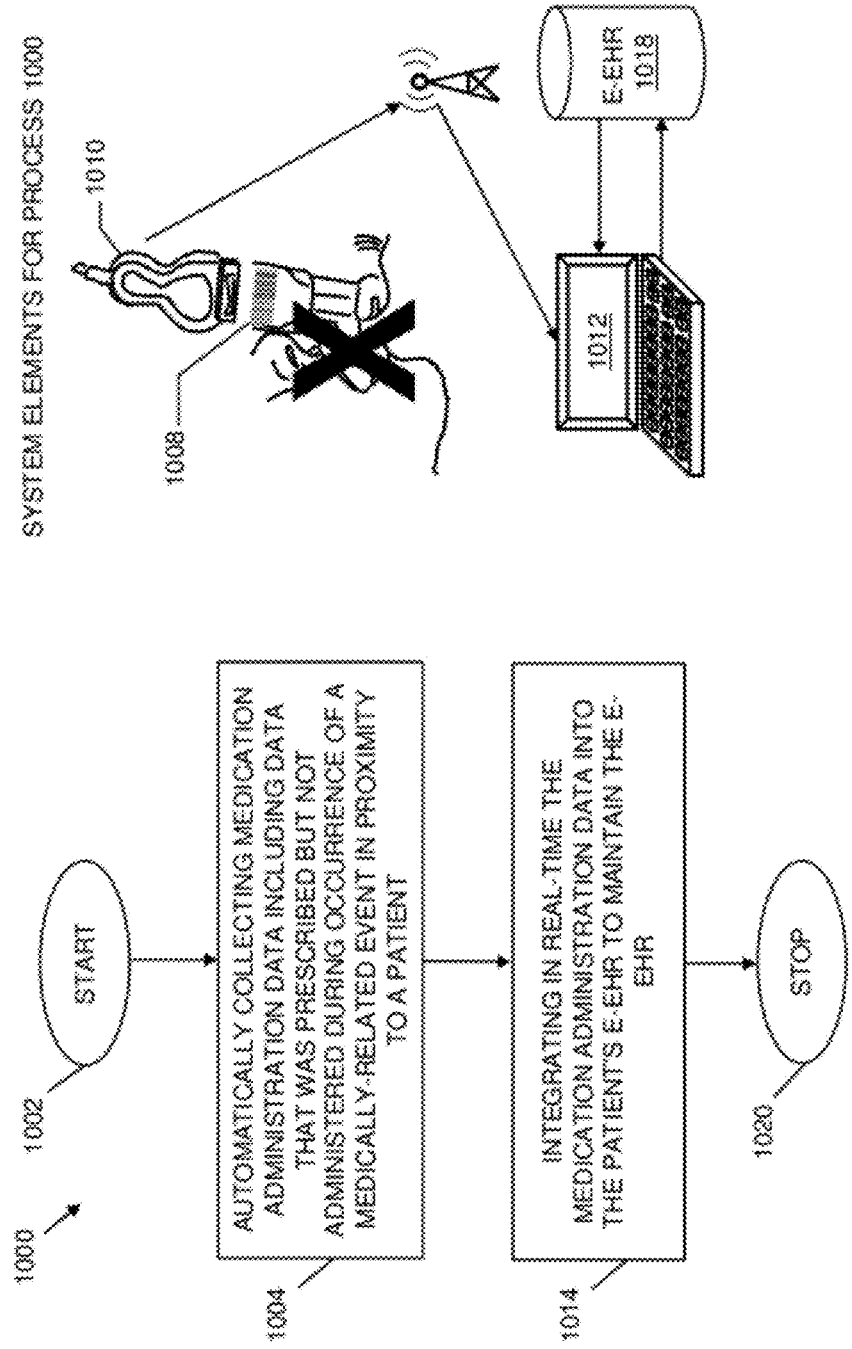
FIG. 10 depicts a flow chart and exemplary structural elements of a bed-side process of collecting non-administered medication information in association with a medically-related event.

FIG. 10 illustrates a process and system 1000 for automatically maintaining an E-EHR with medication administration related data of medication that is not administered in a medically-related event that is automatically collected in real-time in proximity to a patient, in accordance with an embodiment of the invention. The process begins at step 1002. At step 1004, medication administration data 1008 of the medically-related event associated with the patient may be collected. The step 1004 of collecting the medication administration data 1008 of the medically-related event may be accomplished by an automatic data collection facility in proximity to the patient such as those described herein. In embodiments, the automatic data collection facility may be a machine reader. In an embodiment of the invention, the machine reader may be a handheld barcode reader facility 1010. The handheld barcode reader facility 1010 may read the barcodes on the packaging of a dosage of medication and may be in electronic communication with the prescription administration facility (not shown in the FIG. 10). The medication administration data 1008 may be raw medication identification data that may be transformed to be suitable or used with a medication information database, or it may include a medication data that was prescribed but not administered during the occurrence of the event.

As described herein, additional data about the medically-related event (which in embodiments may be the medication administration data 1008) may be fed into a computer 1012. As an example, a caregiver might scan the coded information on a medication packet to initiate the process 1000. The coded information may be automatically read by the automatic data collection facility. The medication administration facility (110 in FIG. 1) may also prompt the user to enter other relevant data about the patient's current condition at the time of medication administration.

After the medication administration data 1008 of the medically-related event associated with the patient has been collected at step 1004, the handheld barcode reader facility 1010 may communicate via an electronic communication, the collected medication administration data 1008, to the computer 1012 which may represent any of the facilities depicted in FIG. 1 (e.g. prescription management facility 106, prescribing facility 154, outcome database module 124, and the like). In an embodiment of the invention, the electronic communication may be the Internet. Thereafter, at step 1014 the medication administration data 1008 and other information may be integrated automatically in real time with the patient's E-EHR 1018 to maintain the E-EHR 1018 of the patient. The step 1014 of integrating the medication administration data 1008 and other information may be accomplished by using the computer 1012. The step 1014 may further include using the computer 1012 to transform the raw medication administration data so that it can be integrated with the patient's EHR. The process ends at step 1020.

Figure 11:
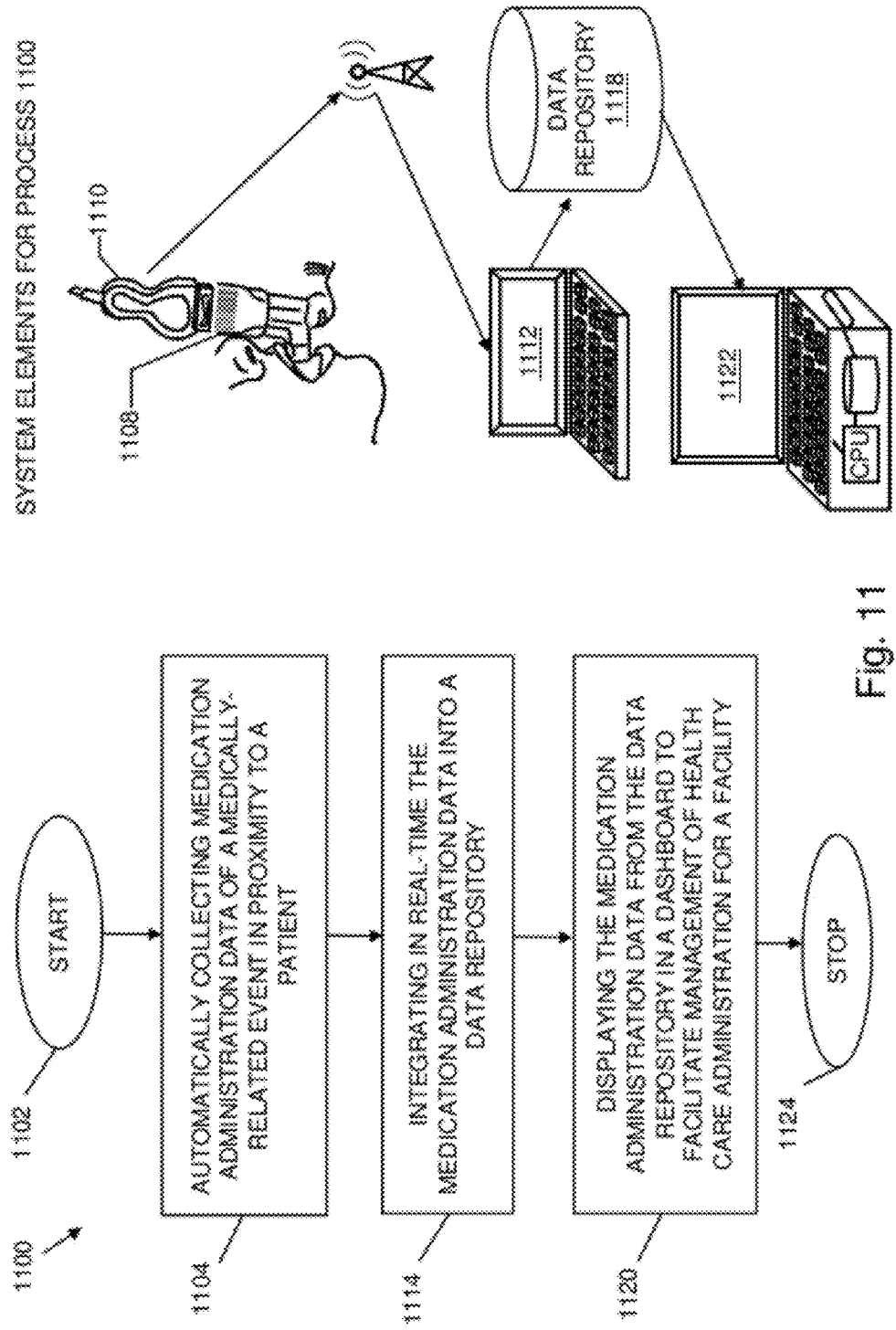
FIG. 11 depicts a flow chart and exemplary structural elements of a bed-side process of medically-related event data collection for real-time updating of a dashboard.

FIG. 11 illustrates a process and system 1100 for maintaining a health information dashboard with medication administration data of a medically-related event that is collected in real-time in proximity to a patient, in accordance with an embodiment of the invention. The process begins at step 1102. At step 1104, medication administration data 1108 of the medically-related event associated with the patient may be collected. The step 1104 of collecting the medication administration data 1008 of the medically-related event may be accomplished by an automatic data collection facility in proximity to the patient such as those described herein. In embodiments, the automatic data collection facility may be a machine reader. In an embodiment of the invention, the machine reader may be a handheld barcode reader facility 1110. The handheld barcode reader facility 1110 may read the barcodes on the packaging of a dosage of medication and may be in electronic communication with the prescription administration facility (not shown in the FIG. 11). The medication administration data 1108 may be raw medication identification data that may be transformed to be suitable or used with a medication information database, or it may include the medication, time of administration, dosage, reaction data and administration of a dosage of medication.

As described herein, additional data about the medically-related event (which in embodiments may be the medication administration data 1108) may be fed into a computer 1112. As an example, a caregiver might scan the coded information on a medication packet to initiate the process 1100. The coded information may be automatically read by the automatic data collection facility. The medication administration facility (110 in FIG. 1) may also prompt the user to enter other relevant data about the patient's current condition at the time of medication administration. Further, the medication administration data 1108 may be raw medication identification data that may be transformed to be suitable or used with a medication information database.

After, the medication administration data 1108 of the medically-related event associated with the patient has been collected at step 1104, the handheld barcode reader facility 1110 may communicate via an electronic communication, the collected medication administration data 1108, to the computer 1112 which may represent any of the facilities depicted in FIG. 1 (e.g. prescription management facility 106, prescribing facility 154, outcome database module 124, and the like). In an embodiment of the invention, the electronic communication may be the Internet. Thereafter, at step 1114 the medication administration data 1108 and other information may be integrated automatically in real time with a data repository 1118. In an embodiment of the invention, the data repository 1118 may be the E-EHR of the patient. The step 1114 of integrating the medication administration data 1008 and other information may be accomplished by using the computer 1112. The step 1114 may further include using the computer 1112 to transform the raw medication administration data so that it can be integrated with the data repository 1118.

At step 1120, after the medication administration data 1108 has been integrated with the data repository 1118, the medication administration data 1108 may be displayed on a dashboard of a user interface to facilitate the management of health care administration for a facility. In an embodiment of the invention, the step 1120 may be accomplished by using a computer 1122. The computer 1112 may include: (a) an input data port to obtain the medication administration data 1108 from the data repository 1118, (b) a database for storing the obtained medical administration data 1108, (c) a Central Processing Unit (CPU) for processing the stored medical administration data 1108, and (d) a user interface to display the processed medication administration data 1108. The process ends at step 1124.

Figure 12:
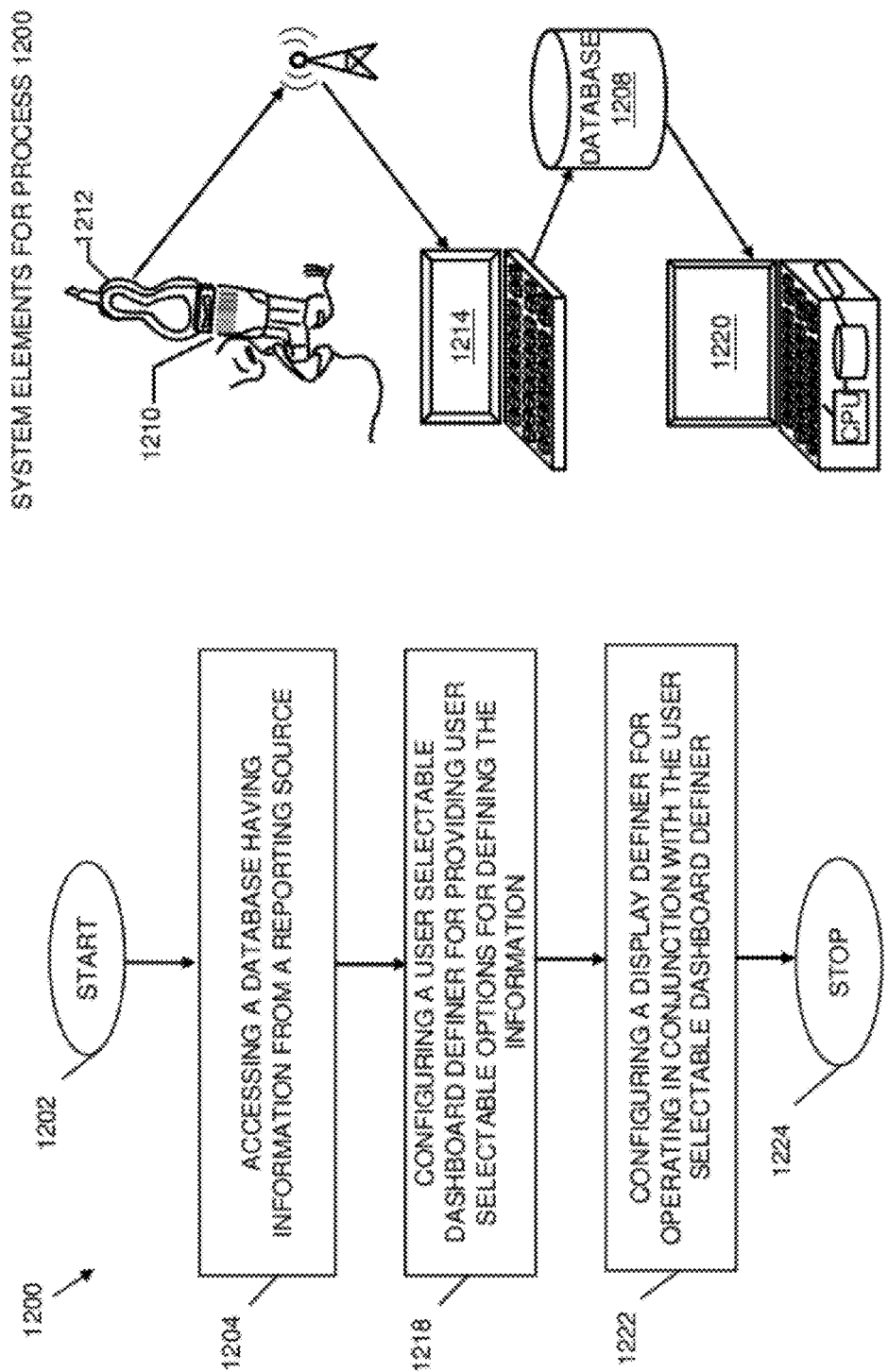
FIG. 12 depicts a flow chart and exemplary structural elements of a process of configuring a dashboard.

FIG. 12 illustrates a process and system 1200 for managing prescription and administration of a medication, in accordance with an embodiment of the invention. The process begins at step 1202. At step 1204, a database 1208 having information from a reporting source may be accessed. In an embodiment of the invention, the reporting source may include an automatic data collection facility for collecting medication administration data 1210 of a medically-related event in proximity to a patient upon the occurrence of the event such as those described herein. In embodiments, the automatic data collection facility may be a machine reader. In an embodiment of the invention, the machine reader may be a handheld barcode reader facility 1212. The handheld barcode reader facility 1212 may read the barcodes on the packaging of a dosage of medication and may be in electronic communication with the prescription administration facility (not shown in the FIG. 12). The medication administration data 1210 may be raw medication identification data that may be transformed to be suitable or used with a medication information database, or it may include the medication, time of administration, dosage, reaction data, and administration of a dosage of medication.

As described herein, additional data about the medically-related event (which in embodiments may be the medication administration data 1210) may be fed into a computer 1214. As an example, a caregiver might scan the coded information on a medication packet to initiate the process 1200. The coded information may be automatically read by the automatic data collection facility. The medication administration facility (110 in FIG. 1) may also prompt the user to enter other relevant data about the patient's current condition at the time of medication administration.

After the information has been accessed from the reporting source at step 1204, at step 1218, a user selectable dashboard definer may be configured to provide user selectable options for defining the information from the database 1208. In an embodiment of the invention, the information from the database 1208 may be defined to be presented in a report at a dashboard. In an embodiment of the invention, the step 1218 may be accomplished by using a computer 1220. The computer 1220 may include: (a) an input data port to obtain the medication administration data 1210 from the data repository 1118, (b) a database for storing the obtained medical administration data 1210, (c) a Central Processing Unit (CPU) for processing the stored medical administration data 1210, and (d) a user interface to display the processed medication administration data 1210. Further, at step 1222, a display definer may be configured to operate in conjunction with the user selectable dashboard definer to define the format in which the report from the database 1208 may be presented at the dashboard. The process ends at step 1224.

Figure 13:
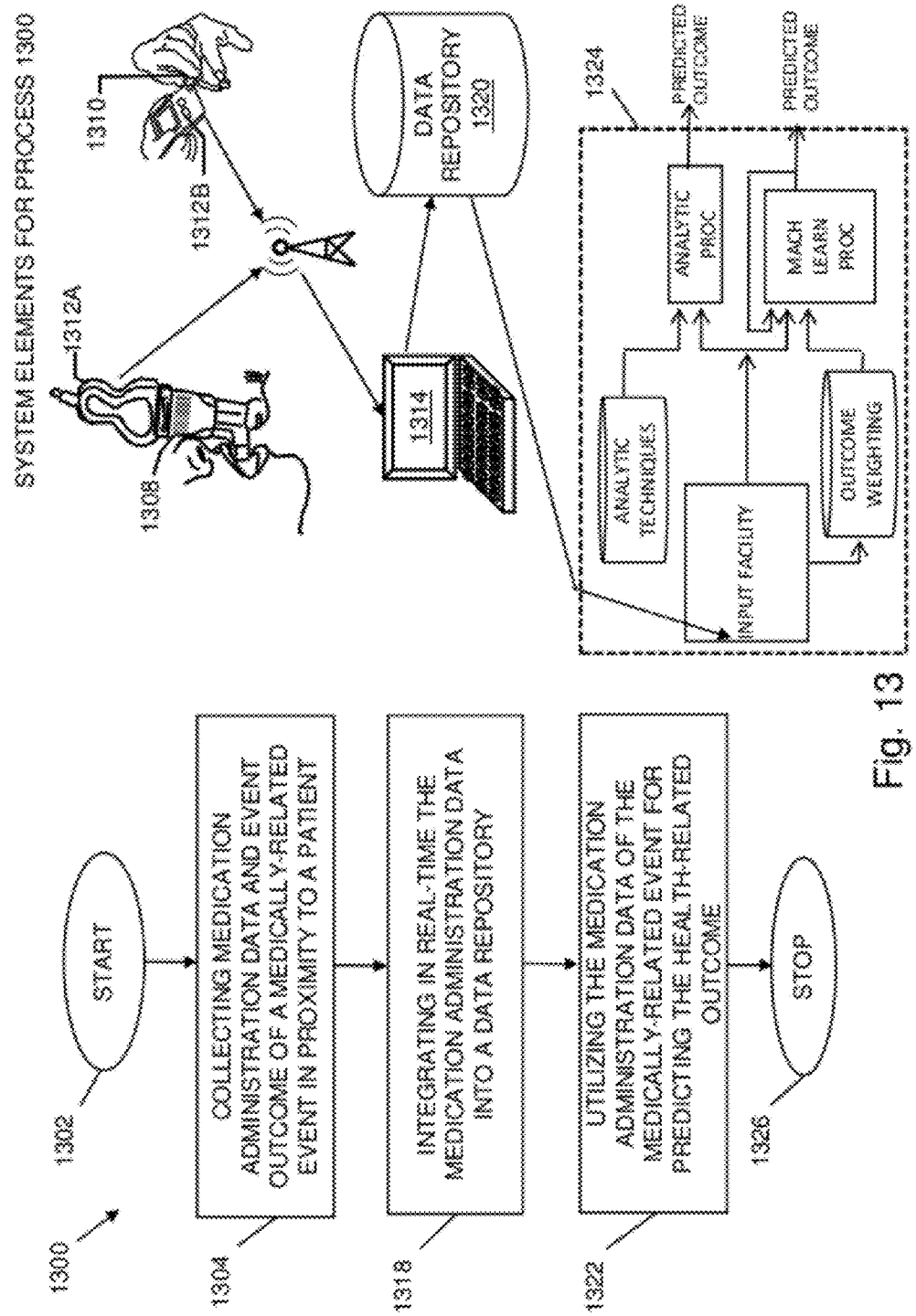
FIG. 13 depicts a flow chart and exemplary structural elements of a process of predicting a medical event outcome.

FIG. 13 illustrates a process and system 1300 for predicting a health-related outcome of a patient with a health condition, in accordance with an embodiment of the invention. The process begins at step 1302. At step 1304, medication administration data 1308 and patient health condition data 1310 of a medically-related event associated with the patient may be collected. The step 1304 of collecting the medication administration data 1308 and patient health condition data 1310 of the medically-related event may be accomplished by an automatic data collection facility in proximity to the patient such as those described herein. In embodiments, the automatic data collection facilities may be a machine reader, health monitoring device, and the like. In an embodiment of the invention, the machine reader may be a handheld barcode reader facility 1312A. The handheld barcode reader facility 1312A may read the barcodes on the packaging of a dosage of medication and may be in electronic communication with the prescription administration facility (not shown in the FIG. 13). In another embodiment of the invention, the health monitoring device may be a handheld blood glucose monitoring facility 1312B. The handheld blood glucose monitoring facility 1312B may monitor the blood glucose level associated with patient and may be in electronic communication with the prescription administration facility (not shown in the FIG. 13). Further, the medication administration data 1308 may include raw medication administration data that may be transformed to be suitable or used with a medication information database, or may include the medication, time of administration, dosage, reaction data, and administration of a dosage of medication. Further, the patient health condition data 1310 may be raw health condition data that may be transformed to be suitable or used with a medication information database, or it may include patient vital signs, patient blood chemistry results, and the like.

As described herein, additional data about the medically-related event (which in embodiments may be the prescription administration data 1308 and the patient health condition data 1310) may be fed into a computer 1314. As an example, a caregiver might monitor the blood glucose level associated with the patient by using the handheld blood glucose monitoring facility 610 or might scan the coded information on a medication packet to initiate the process 600. The monitored information or the coded information may be automatically read by the automatic data collection facility. The medication administration facility (110 in FIG. 1) may also prompt the user to enter other relevant data about the patient's current condition at the time of medication administration.

After the medication administration data 1308 and the patient health condition data 1310 of the medically-related event associated with the patient has been collected at step 1304, the handheld barcode reader facility 1310 and the handheld blood glucose monitoring facility 1312B may communicate via an electronic communication, the collected medication administration data 1308, and the patient health condition data 1310 to the computer 1314 which (as in all embodiments herein) may represent or provide access to any of the facilities depicted in FIG. 1 (e.g. prescription management facility 106, prescribing facility 154, outcome database module 124, and the like). In an embodiment of the invention, the electronic communication may be the Internet. Thereafter, at step 1318 the medication administration data 1308, the patient health condition data 1310, and other information may be integrated automatically in real-time with a data repository 1320. In an embodiment of the invention, the data repository 1320 may be the E-EHR of the patient. The step 1318 of integrating the medication administration data 1308, the patient health condition data 1310 and other information may be accomplished by using the computer 1314. The step 1318 may further include using the computer 1314 to transform the raw medication administration data and the raw health condition data so that it can be integrated with the data repository 1320.

At step 1322, after the medication administration data 1308 and the patient health condition data 1310 has been integrated with the data repository 1320, the medication administration data 1308 and the patient health condition data 1310 may be utilized for predicting the heath record outcomes. In an embodiment of the invention, the step 1322 may be accomplished by the outcome analytics facility 1324. The functionality of the outcome analytics facility 1324 may be similar to the outcome analytics facility 128 as depicted in FIG. 3. The process ends at step 1326.

Figure 14:
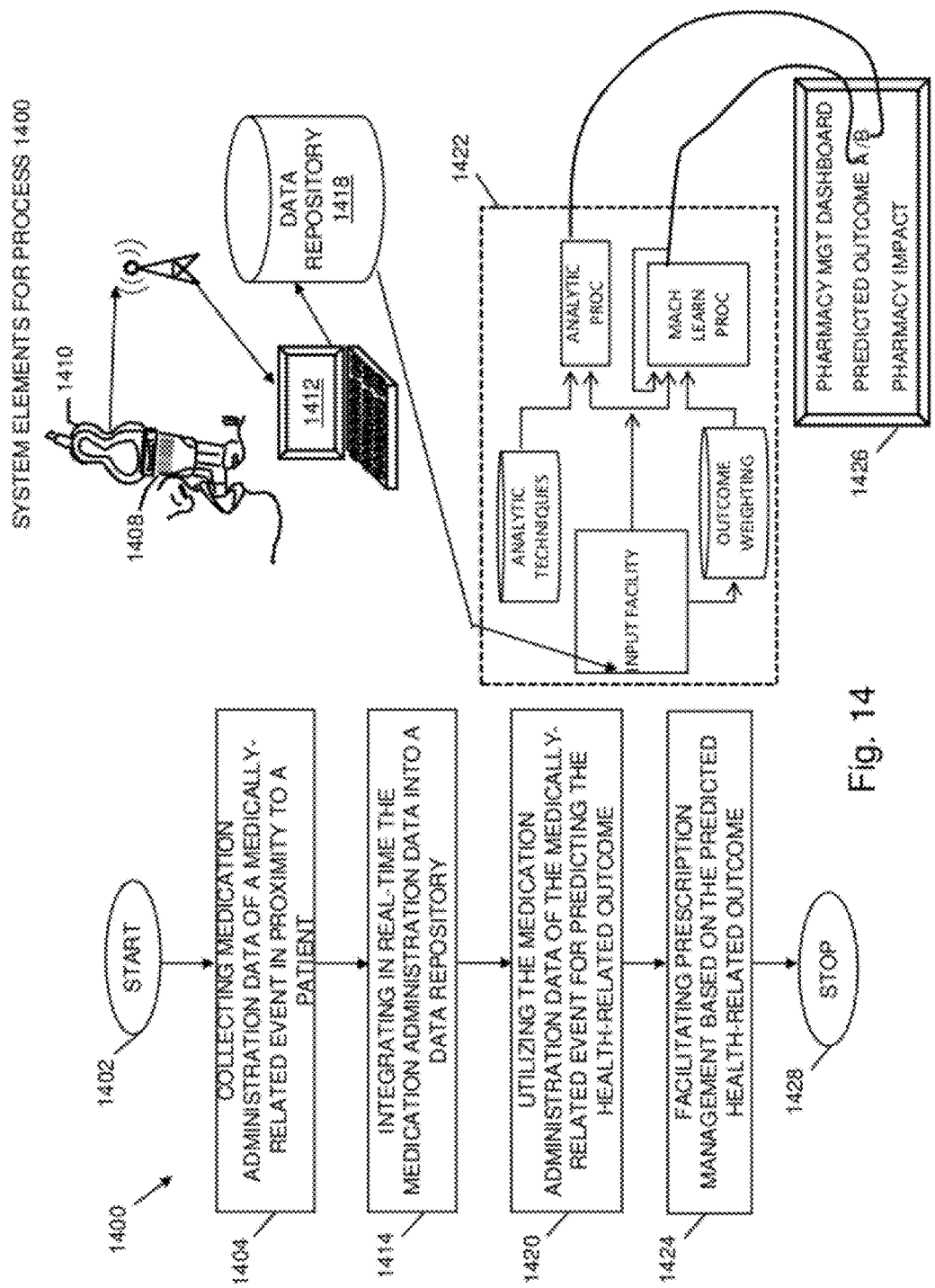
FIG. 14 depicts a flow chart and exemplary structural elements of a process of using medical event predicted outcomes in a medical-related dashboard.

FIG. 14 illustrates a process and system 1400 for predicting a health-related outcome of a patient with a health condition, in accordance with an embodiment of the invention. The process begins at step 1402. At step 1404, medication administration data 1408 of a medically-related event associated with the patient may be collected. The step 1404 of collecting the medication administration data 1408 of the medically-related event may be accomplished by an automatic data collection facility in proximity to the patient such as those described herein. In embodiments, the automatic data collection facilities may be a machine reader. In an embodiment of the invention, the machine reader may be a handheld barcode reader facility 1410. The handheld barcode reader facility 1410 may read the barcodes on the packaging of a dosage of medication and may be in electronic communication with the prescription administration facility (not shown in the FIG. 14). Further, the medication administration data 1408 may include raw medication administration data that may be transformed to be suitable or used with a medication information database, or may include the medication, time of administration, dosage, reaction data, and administration of a dosage of medication.

As described herein, additional data about the medically-related event (which in embodiments may be the prescription administration data 1408) may be fed into a computer 1412. As an example, a caregiver might scan the coded information on a medication packet to initiate the process 1400. The coded information may be automatically read by the automatic data collection facility. The medication administration facility (110 in FIG. 1) may also prompt the user to enter other relevant data about the patient's current condition at the time of medication administration.

After the medication administration data 1408 of the medically-related event associated with the patient has been collected at step 1404, the handheld barcode reader facility 1410 may communicate via an electronic communication, the collected medication administration data 1408, to the computer 1412 which may represent any of the facilities depicted in FIG. 1 (e.g. prescription management facility 106, prescribing facility 154, outcome database module 124, and the like). In an embodiment of the invention, the electronic communication may be via the Internet. Thereafter, at step 1414 the medication administration data 1408 and other information may be integrated automatically in real-time with a data repository 1418. In an embodiment of the invention, the data repository 1418 may be the E-EHR of the patient. The step 1414 of integrating the medication administration data 1408 and other information may be accomplished by using the computer 1412. The step 1414 may further include using the computer 1412 to transform the raw medication administration data so that it may be integrated with the data repository 1418.

At step 1420, after the medication administration data 1408 has been integrated with the data repository 1418, the medication administration data 1408 may be utilized for predicting the heath record outcomes. In an embodiment of the invention, the step 1420 may be accomplished by the outcome analytics facility 1422. The functionality of the outcome analytics facility 1422 may be similar to the outcome analytics facility 128 as depicted in FIG. 3. Further at step 1424, the predicted output generated by the outcome analytics facility 1422 may be utilized to facilitate prescription management as depicted by pharmacy management dashboard 1426. The process ends at step 1428.

The FIG. 15 illustrates an exemplary dashboard 1500 to depict a medication administration event for a patient in the Long Term Care (LTC), in accordance with an embodiment of the invention. In an embodiment of the invention, the dashboard 1500 may be populated with the real-time data from the E-EHR/E-EMR facility (not shown in FIG. 1). Further, at the time of administration of medication, the caregiver administering the medication to the patient may utilize technology-enabled devices such as handheld barcode scanners or other devices at the point of administration. The use of handheld barcode scanners may allow real-time capturing of information about the events associated with medication administration. In an embodiment of the invention, the information captured upon scanning of the barcodes may be displayed by the dashboard in an area 1502. Further, the items depicted in area 1504 may also be loaded automatically on the dashboard as the barcodes are detected by handheld barcode scanners. The items in the area 1504 may include, but not limited to, patient name, patient ID, location of the patient, and the administrator/caregiver ID. In an embodiment of the invention, the caregiver may confirm the items displayed in the area 1504 by selecting an option YES as displayed in area 1510A. In another embodiment of the invention, the caregiver may reject the items displayed in the area 1504 by selecting an option NO as displayed in the area 1510A.

Further, in an embodiment of the invention, after the caregiver has confirmed the items displayed in area 1504, an area 1508 may get displayed automatically. In an embodiment of the invention, the area 1508 may include the medication name that is being administered to the patient. In an embodiment of the invention, the caregiver may confirm the displayed medication in the area 1508 by selecting an option YES as displayed in area 1510B. In another embodiment of the invention, the caregiver may reject the displayed medication in the area 1508 by selecting an option NO as displayed in the area 1510B.

Further, in an embodiment of the invention, after the caregiver has confirmed the medication displayed in area 1508, an area 1512 may get loaded automatically on the dashboard. The items in the area 1512 may include, but not limited to, the administration date, the administration time, the dose administered to the patient, the medication prescription (RX) written for the patient, the RX approved, the information about first filling of the medication, the information about last filling of the medication, the delivery date of the medication, and the like.

Further, in an embodiment of the invention, the dashboard 1500 may display an area 1514 to prompt the caregiver to enter information about the medication administration event. The entered information may include, but not limited to, administrator observations, the details of the vitals associated with the patient, the review of prior symptoms associated with the patient, nay new symptoms after the medication was administered to the patient, and the like.

Computer-based or electronic order entry may guide doctors, nurses, and other authorized staff through quick and efficient electronic ordering of medication, related treatment, and clinical care services required by patients. The clinical care services may include diet, nutrition, therapy, lab services, and the like. This in turn may streamline the interaction between the pharmacy/medication supply units and healthcare entities. Time consumed in placing the orders via conventional mediums such as phone calls and faxes may be reduced. In addition, automated, real time alerts and warnings may be issued regarding allergies, clinical interactions, dosage, duration issues, and generic substitutions. Further, online help regarding medicines and regulatory compliance may also be offered by the system. This process may improve patient safety and reduce medication errors through increased order accuracy. Further, less time may be spent on ordering and chasing down incomplete, inaccurate, or missing orders. Thus, the time saved through use of an automated system may be utilized in better patient care.

Referring again to FIG. 1, various facilities for managing and/or tracking different prescription management events, such as validation, selection, dispensing, marking, and delivery are depicted among several other facilities and features of the invention. A prescription management facility 106 may include a validation/selection facility 102, a dispensing and marking facility 104 and a delivery facility 108 apart from other facilities as shown in FIG. 1. These facilities may be configured to receive/send real time event tracking data with other patient medical related facilities. Real time tracked events from various medical related event streams may be utilized by the prescription management facility 106 for real time and automated entries, processing, and checks. Medical event streams may include information from prescribing units, care planning facilities, laboratories & imaging centers, insurance & payments units, rehabilitation and long term care facilities, electronic medical record repositories, dashboards and databases, third party sites, healthcare facilities, and the like.

The prescription management facility 106 may include one or more interfaces that may facilitate entry of order data. Orders associated with the various prescription management services may be placed via any of several mediums including submitting an order form over the Internet, accessing the interface through public and/or private kiosks, submitting orders (e.g. prescriptions) through mobile phones (SMS and calls), electronic fax, system-to-system order transfer, wireless portable devices (e.g. dedicated prescription management devices), and the like. For example, a nursing home care provider secure website may be designed wherein orders for patients may be entered by physicians, medical consultants, nurses, healthcare staff, and the like. The prescription management interface(s) may be configured with security provisions that may restrict orders from being entered and/or discontinued except by a nurse practitioner, doctor or a specialist and not by any other facility staff or employee.

The prescription management facility 106 interface may include a graphical user interface for order entry. In such an interface, a user may utilize various buttons, list boxes, and text boxes for entering and managing order data. In order to confirm the validity of data entered, the software underlying the graphical user interface may validate the entered data. For example, if the age of the patient may only be recorded in numeric format, JavaScript code embedded in the interface software may disallow the entry of non-numeric data into the age field. Likewise, other validation may be embedded into the graphical user interface to ensure the validity of the data.

Orders entered in the prescription management facility 106 may allow selection and/or verification of record through an interface such as GUI. As described above, the validation and verification of order entered may be performed in real-time during entry. For example, a nursing home portal may contain patient profiles collected from various dashboards, electronic medical records, databases, and the like. Access to the portal may require user authentication.

In addition to real time validation of order data entered into data fields of a user interface, user authentication may be employed and may be provided in the form of login credentials, encrypted passwords, voice-based authentication, physical authentication, biometric (e.g., use of eye scan or finger prints), and other types of user-based authentication. To further ensure security of patient records, an order entered by a medical practitioner may require authenticating the medical practitioner for a particular patient by validating other aspects such as referrals, signed patient agreements to be treated, and the like. In addition, medical order entry may require selection of an order type through menus or tabs that may be enabled for the patient/provider combination and may correspond to various parameters, such as new orders, admissions record, prior authentication, history, allergies, physician's orders, and the like.

Validating a physician's orders may include requiring access to detailed information of the patient such as current diagnosis and orders, discontinued orders, allergies and reactions, and the like. Although this information may be collected in real time from the prescription desk of the physician or medical consultant, a judicious, error-free, quick, and responsive method of collecting such real time information may be aided by using patient identification (ID) numbers or codes. For example, there may be approx. 250 patient entries with the name Allen Smith known to the pharmacy management facilities. However, when Allen Smith's ID No. SYS2244 is used, only the medical information that corresponds to a particular Allen Smith may be fed in to the prescription management system to access detailed patient information. Validation may rely on information in the selected profile (e.g., the patient has been prescribed two dosage of Aspirin EC oral tablets and one dosage of Azathiocrine—50 mg tablets, to be consumed once a day at 8:00 AM in the morning) to help avoid potentially dangerous discrepancies in prescription management. In this example, new prescription information (e.g., received from a physician's hand-held prescribing unit) may indicate use of a particular drug; however, the existing prescription information may indicate potential adverse side effects due to this combination of medications. In such a case, real-time validated information may be sent to the physician's hand-held prescribing unit as an alert to possibly adjust the prescription before the patient leaves the office. Alternatively, the validated information may be sent as a reminder to a nurse at the time of administration to ensure that the proper precautions have been taken to allow the combination of medications in the patient.

The prescription management facility 106 may rely on information received from prescribing units, laboratories, imaging units, and the like to ensure a prescription is validated. The prescription management facility 106 may affect correlation between the tests, results, dosage frequency (high, medium, low), and/or efficacy of the prescribed drug for validation. For example, data from imaging tests may indicate a very low bone density in a patient who has been prescribed high dosage of steroids for a problem unrelated to her bones. The correlation of the imaging data with the new prescription for steroids may indicate potential further deterioration of the patient's bone density; therefore alerts and/or reminders may be sent to the concerned entities (e.g. doctor, patients, prescription management facility, and the attendants) regarding these potential damaging adverse effects.

Similarly, real time information may be collected from third party sources, pharmacy planning units, regulatory databases, and the like regarding the interaction, effects, and detailed reviews of various drugs and their interaction. This may be helpful in managing adverse reactions of various medicines on patients as well as educating/informing healthcare professionals and doctors about new findings on the drugs and their interaction. This process may be specifically significant in cases where new drugs for chronic or pandemic diseases are prescribed, consumed, and tested. This may be explained with the help of the following example.

During a pandemic contagious virus spread, a particular medication 'X' may be prescribed. Real time information regarding the usage, effects, and disposal (complete medication cycle) may be collected and analyzed by the pharmacy planning and regulatory units. Data may be collected from nursing care centers, hospitals, patient responses, clinics, and the like that indicates that this medicine 'X' results in certain side effects such as nausea, diarrhea, and extreme body ache. Clinical trials and analysis may recommend that these side effects are suppressed if the medicine 'X' is supplemented with medicine 'Y.' Information from clinical trial laboratories may be sent in real time to the various facilities including validation and selection facility of the prescription management facility. Upon validation of the 'order entry' form for a patient, a safety check may be conducted to ensure that medicine 'X' and medicine 'Y' are prescribed together for any reported case of the above disease. Thus, the validation and safety checks may be in real time and actionable.

The prescription management facility 106 may also include automated insurance coverage checks. Information regarding the patient's insurance plan, medicines and treatments covered under that plan, and payment option details may be accessed in real time by the prescription management facility 106. Verification of insurance information may be significant since coverage of patients within any particular insurance company may vary. As shown in FIG. 1, event information from insurance planning and insurance and payments facilities may be collected in real time and shared with the prescription management validation and selection facility 102. The prescription management facility 106 may validate that a medication being prescribed to a patient is covered by the patient's policy with the insurance company to avoid use of non-covered medications that may result in phenomenally high expenses for the patient.

In another example, information regarding the validity and payment details for a patient's insurance policy may be shared with the medication facility. In case, the last premiums have not been paid, the patient or his/her caretakers may be informed regarding the same. In certain cases, provisions may be made to facilitate payments from the closest kiosk within the healthcare facility.

The prescription management facility 106 may also include automated insurance claims processing checks. The information for prescribed medications or indicative symptoms of a disease may be shared with the insurance processing and payment facility. Other information that may be shared may be frequency and duration of the treatment, professional information of the surgeon or healthcare, percentage of payment to be borne by the insurance company and the like. This information may be automatically compared by the prescription management facility 106 with information supplied by the patient and any discrepancy between the two may be reported. This automatic process may speed-up the portion of the prescription management cycle related to insurance claims processing.

In an embodiment, the system may select and validate order information for various information fields such as order type, medication, dosage, frequency, day's supply, dispensing quantity, special instructions, physician information, etc. This information may be significant in facilitating automated medication dispensation processes. For example, it may be pertinent to correctly calculate the day's supply of medication and its dispensing quantity based on the total length of the physician's prescription.

Duplication of orders may be recorded in real time. In response to any duplicate entry of order an error message may be displayed, alerting the user of a duplicate entry. Order information may also be validated for possible duplicate orders.

The prescription management facility 106 may include inventory management capabilities in that the system may match a prescribed drug with the pharmacy inventory. Discrepancies, such as low inventory, unavailability of a drug or its substitute, and the like may result in an order for this particular drug being prepared. Through proper inventory management, a medication dispensing process associated with the pharmacy management facilities may be a just-in-time dispensing process that may judiciously assess the quantity and time of delivery for orders. For a healthcare facility, the orders may also be dispensed as per the internal organization or layout. For example, separate orders may be prepared for separate floors (e.g., ground, first, second, etc.) or by nursing station (pediatrics, dental, gynecology, etc.) or by type of patients (inpatient or outpatient wards) Such an automated medication dispensing process may reduce the dispensing time required, mitigate financial risk and administrative burden from unused quantities, and minimize wastes and unnecessary expenses, thereby providing an efficient system capable of meeting patient needs.

Automation, accuracy, and efficiency may be enhanced with bar coded patient medicine packs that may be utilized in combination with technology enabled medicine pack bar code readers by healthcare professionals (e.g., nurses) to administer and track in real time medications and treatments for each patient. The bar coded med packs may ensure safe, proper, and timely administration of drugs to patients. These bar codes may be read with the help of scanners, camera-based mobile phones, or any other wired or wireless device with scanning or imaging capabilities. The data encoded in the bar code, matrix code, line code, 1D code and the like may be a unique prescription identifier that also identifies essential attributes of the prescription. For example, the code may include a unique prescription identifier and a unique dosage identifier. This information may be used to lookup further detailed information about the planned medication administration event, such as the medication, the dosage, the time of administration, the patient, the expected location of the patient, and the like. Alternatively, more extensive information may be coded into the label or identifier that may include the patent name and ID for example, to allow for manual or semi-automated verification of the patient data by the nurse at the time of administration without the need of a network connection to a facility such as the prescription management facility 106.

The prescription management facility 106 may handle automated refill orders and refill alerts to further improve prescription management efficiency.

The prescription management facility 106 may include a therapeutic equivalent facility which accepts electronic medication orders and suggests therapeutic equivalents. Drug products classified as therapeutically equivalent may be substituted with the full expectation that the substituted product will produce the same clinical effect and safety profile as the prescribed product. In embodiments, drug products may be considered to be therapeutically equivalent if they meet these criteria: they are pharmaceutical equivalents (contain the same active ingredient(s); dosage form and route of administration; and strength.); they are assigned by FDA the same therapeutic designates a brand name drug or a generic drug to be the Reference Listed Drug (RLD), and assigns therapeutic equivalence codes based on data that a drug sponsor submits in an Abbreviated New Drug Application to scientifically demonstrate that its product is bioequivalent (i.e., performs in the same manner as the Reference Listed Drug). The therapeutic equivalent facility may contain a library of such therapeutic equivalents and suggests them to the prescribing professional upon order entry based on for example, whether the proscribed medication is on the patient's insurance formulary.

Real time tracking of medical events may be facilitated with the help of a record system stored in a database. For this purpose, one or more databases may be maintained, such as a distributed database. A distributed database model may facilitate replication of data so that failure of one of the nodes may not affect the performance of the overall system (fault tolerance) and as a result, the data may be available 24×7.

Data stored in the distributed database may be fragmented horizontally, vertically or in a mixed mode, i.e., involving both horizontal and vertical fragmentation for increasing the retrieval of data. For example, the records for Pittsburgh may be horizontally fragmented and stored in one of the distributed database nodes located at Pittsburgh. By horizontally fragmenting the records corresponding to Pittsburgh, the records for Pittsburgh may be placed in a database node located at Pittsburgh. Usually, patients and doctors residing in Pittsburgh may be serviced from the database node located in Pittsburgh. Records corresponding to other locations may be also be maintained at each location; that is, a database node.

Data stored in the databases may include medical content in the form of prescription by a doctor, surgical reports, pathological tests, patient's medical history, and the like. While legacy data may be stored in the database for record keeping, this data may be continuously updated with real-time data received at the database from various other facilities. Further, the database may be enabled to update information in real-time. In an embodiment, the database may be an OLAP Online Analytical Processing.

The database may include capabilities of transforming the data into a required format. For example, data may be received from a number of facilities such as an MRI facility. This may require transformation to an acceptable format before it may be stored in the database. In this aspect, the database may itself include software facilities for transforming data into an acceptable format. Alternatively, data may undergo a transformation in a transformation facility for converting the data into a format acceptable for storing the same in the database.

The database may provide one or more streams to registered data users regarding medical events. For example, an RSS feed may be provided, and registered users may receive medical event data related to their patients, latest trends in medical sciences, drug developments, administration of new drugs to patients and their outcomes and the like.

Data security may be ensured in the medical facility through authentication requirements. For example, an entry for a record to be stored in a database may only be made upon proper authentication of a user along with an entry of his personal as well as log in details. In another embodiment of a fully automated tracking and record keeping database management system, unique log in credentials may be provided to users who are registered with the medical facility and corresponding details of users are gathered and stored in a separate database once during registration. Any subsequent correspondence from a registered user may be accompanied with certain security checks to confirm already stored details of the registered users. Further, various records of the database may be encrypted for a secured access by an authorized and intended person only. Encryption of the records of a database in the medical facility implements an authorization protocol that can be decrypted by a specific secured key only. In an embodiment, a token may be issued to a user on any type of association with the database that may enable further processing and assist in track keeping of database communications. The token, in an embodiment, may be generated using an automated system in the form of an email.

The information stored in databases may be utilized for generating reports, sheets, updates, and sending auto-generated emails to intended recipients. Such reports, updates and emails may be customized for a particular person or a section of people. Further, such customized reports and emails may be generated periodically or on demand. The reports and emails may depict simple medical information in textual form for a period of time, statistical analysis based on data, forecasted details pertinent to healthcare, medical suggestions and the like.

The pharmacy or medication unit may be either in-house or remote. The in-house pharmacy system may be an automated, self service dispensing system that may be located in the vicinity of the healthcare facility. The system may be endowed with sufficient stocks (e.g., 350 SKUs) to meet immediate patient medication needs at any given time. In other cases, remote pharmacies may interact with the healthcare facility via wired or wireless networks. The medications and the packaging may be supplemented with electronically readable information. The electronic/machine readable information may be a RFID tag, barcode, optical disk, and the like.

Remote dispensing of prescriptions may be supported by automated dispensing machines such as in-facility kiosks, third party home delivery chains, and the like. Remote dispensing may include security to ensure proper authentication of the recipient through such means as identifiers, passwords, finger scan, and the like. Further, the medications usage from the dispenser may be tracked using tags, scanners, or sensors.

Similarly to integrated prescription dispensing facilities, remote dispensing means may be able to detect nearly exhausted supply levels.

In accordance with embodiments of the present invention, smart phones and other similar wired or wireless devices may be used for implementing the given invention. Similar to a web application, the present invention when enabled on a smart phone or may be used for various functions for prescription management such as order entry, safety checks and alerts, insurance coverage checks and claims processing, medication dispensation, care planning, and the like. Smartphone applications may take advantage of high resolution interfaces available on some smart phones. The interfaces may be graphical, tactical, touch-based, web-based, gesture-based, intelligent user interface, motion tracking interface, multi-screen interface, text user interface, voice user interface, and the like. A prescription management smartphone application may interact with various databases such as electronic medical records database, regulatory database (e.g., FDA), laboratories and imaging database, physician's health records, and the like.

A smartphone application may alternatively be available for patient use and may be used to create medication alerts for a patient in real time. For example, information about a patients purchase an over-the-counter generic drug may be captured in real time and sent to the prescription management facility 106 where validation may determine that other prescriptions that the user it taking may result in a severe reaction to a composition in the purchased drug. This information may be immediately broadcasted in real time to the user's smartphone application or as an automated voice call and/or a text message. In addition, information provided in the alert may suggest substitutes that the user may purchase.

The prescription management facility 106 may include a physician ordering facility that may capture prescription behaviors and/or practices of a physician to help improve validation, quality of prescriptions, and the like. In an example, a physician may routinely ask his nurse to submit prescriptions for him. The system may recognize that prescriptions coming from a variety of nurses in the doctor's office are all authorized by the same doctor and may use this information to automatically associate prescriptions from these nurses with this doctor.

In-patient facilities (hospitals, nursing homes, long term care, residential rehabilitation centers, and the like) typically collect new patient information during a patient admission process. A pharmacy management facility may include built-in capabilities to capture and/or receive complete patient information from a facility admission module, thereby reducing the opportunities for typographical or other human data entry errors. In addition, admissions modules often automatically collect medical history information (from the patient, a representative, or a medical record). This information can be processed through the built-in admissions information sharing modules and presented in a form that is most useful to the prescription management, dispensing, and validation facilities.

The invention may further include a prescription administration facility 110 to facilitate proper administration and real time data capture of prescription administration information. By utilizing technology enabled devices such as handheld or other devices at the point of administration, important information about the events associated with and immediately after administering medications may be captured in real time. Such technology enabled devices may also benefit the administration process by providing real time data and contextual information for the person performing the administration (e.g. a patient, nurse, technician, physical therapist, or other care provider). The prescription administration facility 110 may access or communicate with a data center that may provide information from any of a variety of medical information related sources as depicted in FIG. 1. Such access may typically be via a wireless connection.

In an exemplary case, the wireless connectivity may be Internet. In other exemplary cases, the wireless connectivity may be WI FI, WiMax, Bluetooth, Infrared and other similar types of wireless technologies. In an embodiment of the invention, the wireless connectivity may be a secured connectivity. The security may be of different types including Wireless Encryption Protocol (WEP), WI FI Protected Access Pre Shared Key (WPA-PSK), MAC address filtering and the like. WEP works by establishing a shared key between the clients (network cards) and the wireless router, then using the key to encrypt and de-encrypt the data passing between them. WPA-PSK is a WI FI standard that improves upon the security features of WEP. To use WPA-PSK, a shared key or "pass phrase" is set. Using Temporal Key Integrity Protocol (TKIP), WPA-PSK automatically changes the keys at a preset time interval, thus making breach of security difficult. In MAC address filtering, each network adapter or card (wired or wireless) has a unique number assigned to it called a MAC address. As a result, if a wireless USB adapter is plugged into a computer, it will show its own MAC address when connected to the Internet.

The technology enabled prescription administration facility 110 may facilitate providing bedside prescription administration that may further facilitate capturing all care giver observations and clinical events performed as part of the prescription administration. The prescription administration facility 110 may further provide step-by-step guidance and alerts for working with and providing care for patients. The prescription administration facility 110 may further guide nurses through administering and documenting medication and treatment for each patient. Patient-specific medication packs provided from the prescription management facility 106 may include bar-codes that may facilitate bedside verification for all medication and treatment at the moment of administration. As described herein, the information captured on the bar-code label or other identifier may include a unique dosage-specific identifier that, when presented to the prescription management facility 106, can be used to lookup all of the essential patient information. Alternatively, essential patient information may also be encoded in the identifier so that a caregiver may manually or semi-automatically verify patient information without the need of a network connection to the prescription management facility 106. The prescription administration facility 110 may also facilitate automatic collection of data for documentation of all medication and treatment administration activities using bed-side readers, scanner, proximity detectors, and the like. The bed-side data capture facility 110 may include a plurality of visual and/or audible prompts to which a nurse or other caregiver may response to capture information that my not be readily captured automatically in all instances (e.g. coloration of patient's skin, condition of patient's hair, and the like). In an embodiment of the invention, the prescription administration facility 110 may collect data that includes, without limitations, medically-related event, healthcare related events, patient health condition data, patient physical activity data, patient treatment data, patient oral consumption data, patient visitor data, patient outcome data and patient psychological data. Further, the prescription administration facility 110 may include a real-time data integration facility that may provide integration of this collected data with the E-EHR/E-EMR facility 118. In an example, the patient health condition data may include the patient's vital signs collected automatically at the time of medication administration and/or at other times, such as through the use of wireless body monitors that may be in wireless communication with the HPDMA 100. In another example, the patient physical activity data may include patient's position and movement facilitated by the caregiver and patient sleep data. In yet another example, the patient treatment data may include bathing, dressing, wound care, bed position adjustment, physical therapy, psychotherapy and patient position adjustment. In yet another example, patient oral consumption data may include foods prepared for the patient and foods consumed by the patient, fluids consumed by the patient and non-prescription medications consumed by the patient.

The prescription administration facility 110 may also collect medication administration data from coded information of the packages of medications, for example, the medication pillow packs. The medication administration data from the medication pillow packs may include patient identification information. The prescription administration facility 110 may also collect data for the medication that was prescribed but not administered to the patient.

Further, an electronic history of each activity and dosage for automatic, anytime reporting and documentation may also be achieved with the prescription administration facility 110. To help with ensuring proper patient communication and care is provided by all care givers, the prescription administration facility 110 may access patient records to automatically display patient pictures, medication pictures and additional information that may aid verification and prescription safety. The prescription administration facility 110 may further provide 24×7 access to pharmacy experts through wireless connectivity capabilities described herein.

Further in an embodiment of the invention, prescription administration facilities may include integration of the computing device with a scanner for scanning barcodes. The barcode scanning recognition technology may capture medication data, patient data (e.g. through scanning of a wristband, or other identifier), administrator data (e.g. through scanning of the administrator ID badge), and the like in real time and allow the caregivers to chart and maintain all critical patient information as they administer. At the time of prescription administration, the administering professional using the prescription administration facility 110 may scan barcodes, which will populate various fields in the prescription administration tracking records. Alternatively, or in conjunction with the scanning, the data relating to administration may be entered into the prescription administration facility 110. In embodiments, once the information is entered, and prior to administration, the information may be validated such as through communicating with the prescription management facility 106 data servers. In an exemplary case, the barcode scanner (hereinafter the barcode scanner will be interchangeably referred to barcode reader) may be a handheld scanner. The handheld scanner may have a handle and typically a trigger button for switching on the light source associated with the scanner.

The barcode scanner may work with different technologies. In an example, the barcode reader may be a Pen-type reader. The Pen-type readers consist of a light source and a photodiode that are placed next to each other in the tip of a pen or wand. To read a bar code, the tip of the pen moves across the bars in a steady motion. The photo-diode measures the intensity of the light reflected back from the light source and generates a waveform that is used to measure the widths of the bars and spaces in the bar code. Dark bars in the bar code absorb light and white spaces reflect light so that the voltage waveform generated by the photo diode is a representation of the bar and space pattern in the bar code. This waveform is decoded by the scanner.

In another example, the barcode scanner may be a laser scanner. Laser scanners work the same way as pen type readers except that they use a laser beam as the light source and typically employ either a reciprocating mirror or a rotating prism to scan the laser beam back and forth across the bar code. As with the pen type reader, a photodiode is used to measure the intensity of the light reflected back from the bar code. In both pen readers and laser scanners, the light emitted by the reader is rapidly varied in brightness with a data pattern and the photodiode receive circuitry is designed to detect only signals with the same modulated pattern.

In yet another example, the barcode reader may be a Charge-Coupled Device (CCD) reader. The CCD readers use an array of hundreds of tiny light sensors lined up in a row in the head of the reader. Each sensor measures the intensity of the light immediately in front of it. Each individual light sensor in the CCD reader is extremely small and because there are hundreds of sensors lined up in a row, a voltage pattern identical to the pattern in a bar code is generated in the reader by sequentially measuring the voltages across each sensor in the row. The difference between a CCD reader and a pen or laser scanner is that the CCD reader is measuring emitted ambient light from the bar code whereas pen or laser scanners are measuring reflected light of a specific frequency originating from the scanner itself.

In yet another example, the barcode reader may be camera based readers. The camera based readers use a small video camera to capture an image of a bar code. The reader then uses sophisticated digital image processing techniques to decode the bar code. Video cameras use the same CCD technology as in a CCD bar code reader except that instead of having a single row of sensors, a video camera has hundreds of rows of sensors arranged in a two dimensional array so that they can generate an image.

In yet another example, the barcode reader may be Omni-directional barcode scanner. The Omni-directional scanning uses a series of straight or curved scanning lines of varying directions in the form of a starburst, a lissajous pattern, or other multi-angle arrangement are projected at the symbol and one or more of them will be able to cross all of the symbol's bars and spaces, no matter what the orientation.

Further in embodiments of the invention, the barcode scanner may be connected to the computing device via a serial interface, a proprietary interface, a keyboard wedge, a Universal Serial Bus (USB) connector, any wireless network and the likes.

To ensure proper prescription administration, a variety of validity checks may be performed, some of which have already been described herein. Information related to the prescription administration that may be validated include information such as the number of times the medication is to be provided to the patient in a day, the dosage of the medication, the details of the personnel associated or the responsible with the patient, and the like. Validation may fail if any criterion established relative to these validation points is not met. In an example, if a nurse scans a prescription medicine dosage pack for a patient but during validation, the system determines that the patient has already received a maximum daily dose within the last 24 hours, the system may alert the nurse to the potential overdose. This validation may be possible because the prescription administration facility 110 may allow real time access to medical record information and prescription information provided by the prescription management facilities and other facilities as depicted in FIG. 1. Validation may also involve sending real time information collected during bedside preparation for administration to the prescription management facility to ensure that there has not been a change to the patient's medication that may impact the administration to be performed. In embodiments, this is made possible by the real-time connectivity between the relevant facilities of the system described in FIG. 1, which in this case includes the prescription management facility and the prescription administration facility. If so a stop order or the like may be communicated by the medication management facility and displayed via an interface on the prescription administration electronic device. In this way, the system may prevent the administration of discontinued medications and ensure that the correct medication and dosage is being administered at the right time. Under certain conditions the system might require the caregiver to uniquely identify himself or herself using a plurality of identification methodologies. The collected identification information may be recorded and stored to ensure compliance with regulations and provide tracking information for the caregiver that administered the treatments or care.

Data collected may include actual administration times, drug administered, dosage, patient, personnel who performed the administration (e.g. to track when a shift change has resulted in a different nurse administering a prescription that the one who prepared it from the pharmacy or medicine cart), timing and route of administration (e.g. a refrigerated prescription may be dispensed from a refrigerated storage but may not be administered for several minutes or even hours due to limited staffing or large patient load or the like), therapeutic equivalent considerations, and the like.

The prescription administration facility 110 may also provide alerts for the refills by scanning the barcodes. This alert may notify the pharmacy that a refill for a particular medication is required. Further, the prescription administration facilities may calculate the expiry dates for the bulk items. A bulk item or non-cycle medication is a medication that is not machine dispensable for each dosage, the bulk items may include gels and creams. The scanning of barcodes may further provide the medications a list. The list may include information about which medication is to given at what time and the like.

Further in an embodiment of the invention, the HPDMA 100 may allow feeding of a Minimum Data Set (MDS) with the health status of each patient. The MDS for each patient may be coupled to the care planning facility 152 to develop individual care plans that outline the appropriate interventions required to address specific ailments, handicaps, and other health care needs. In an embodiment of the invention, the coupling may be achieved by integrating the medication administration record (MAR) of the patient into the MDS of the patient. Further, a portion of the patient care plan may be devised using an interface associated with the prescription management facility 106. The care plan may provide a road map to guide all the caregivers who are involved with the patient or residents care. The MDS may provide a comprehensive assessment of each patient's functional capabilities and may help care providers (e.g. nursing home staff) to identify health problems associated with the patient. A list of deficiencies with the patient's overall health and well being may also be generated and recorded in association with the MDS. On the basis of the health problems, a proper plan for the patient may be devised for resolving the health problems or improving the health of the patient.

The HPDMA 100 may also allow measuring and tracking of the clinical outcomes for the patient which may allow devising of effective health care plans for the patient. Further, a decision making tool may be provided to the health care specialist to design the health care plan for the patient. This decision tool may obtain data associated with the patient from the prescription management facility 106 and the medication administration facility 110. The decision tool may also obtain anecdotal data, and the narrative data provided by the nurses in the form of their notes and the ADL information. In an embodiment of the invention, the decision tool may also capture the nursing notes directly from the MAR charts. Further, clinical algorithms may be provided that may suggest changes in the patient's medication. These changes may include change in dosage of the medication, change in the therapy and the like. These changes may be based on the clinical outcomes of the current medication and therapies administered to the patient. Further, the different clinical outcomes may be for pain management, treatment and prevention of pressure ulcers or bed sores, disease specific behavior management related to using anti-psychotic drugs or diabetes programs. Each type of clinical outcome may require focus and collection of different kinds of data associated with the disease and its outcome. Further, each type of data may be data object for the MDS. The HPDMA 100 may also provide different types of physiological sensors to populate data into the MDS.

The HPDMA 100 may also allow tracking of the electronic ordering form for ordering the medication associated with the prescription management facility 106 for populating the MDS. The MDS may record different types of prompts that may occur while filling up the electronic order form. The HPDMA 100 may also allow tracking of the medication administration facility 110 for populating the MDS. The MDS may record different types of prompts that may occur while administrating the medication to the patient. The prompts may include warnings and alerts. The HPDMA 100 may also allow tracking of the documentation module for populating the MDS.

Further in embodiments of the invention, the populated MDS may be combined with additional features to facilitate implementation of special instructions or to act as reminders. In an example, a voice activated head set may be provided to the patient in LTC; this headset may react to verbal inputs and record what is said aloud by the patient and this data may be added to the MDS. In another example, a nurse alarm system may be provided to the LTC patient that alerts the nurse at a nurse station that the patient needs to be attended to. In yet another example, wound management tools may be linked to the MDS. This wound management tool may be in the form of a mobile device application ("App") that is able to scan the patient's wounds and the image may be transmitted to the health care specialist who may then provide advice on how to better manage the healing process of the wound. This application is useful in situations where the patient care facility is remotely located and the specialist is not readily available. In addition, in some instances the second opinion of another medical professional may be required and in this event, an App may be useful in transmitting real life images of the condition of the patient.

In yet another example, the MDS may be linked with pain management tools. The relative intensity of the pain being felt by the patient who may be terminally ill may be recorded and transmitted to the MDS; this data may then be accessed by the nurses and/or attending doctors and the pain management medication may be altered accordingly. In this application, the dosage of the pain medication will correspond exactly to the condition of the patient on that day and excess or inadequate dosages based on conditions recorded a few days ago may be avoided.

Further in embodiments of the invention, the MDS may be populated with data received from the sources of the E-EHR facility 118. The sources of E-EHR facility may include, but not limited to, the prescription management facility 106, the prescription administration facility 110, the patient attributes and events facility 112 and outcome events facility 114. The MDS may also be populated with the new data elements within the E-EHR facility 118. The HPDMA 100 may further provide data or format conversion techniques that may support recording of data in the MDS directly from the existing records in the E-EHR facility 118.

In an example of MDS data collection, a US federally mandated Minimum Data Set of data to be collected periodically from health care facilities to qualify for Medicare/Medicaid reimbursement has been defined. Such an MDS is generally collected first when a patient enters a facility in which MDS is required and then again periodically as part of a Resident Assessment Program. The methods and systems of data collection, real-time collection and exchange, and the like as described herein for the HPDMA 100 may contribute to the effective and thorough collection of MDS at any of a wide variety of patient touch points as described herein and elsewhere. The use of technology enabled data collection device to collect real-time data in proximity to patients may also facilitate the collection, roll-up and transmission of MDS to State and/or Federal authorities (e.g. at the Centers for Medicaid and Medicare Services (CMS)).

The healthcare management platform 100 may provide recording and charting of different kinds of information and events occurring in the system. In an embodiment of the invention, this recording and charting of information may be achieved by entering data in various charts electronically. The HPDMA 100 may also provide a plurality of different types of charts that may include information collected from a wide diversity of important and potentially very different information sources, some of which are described herein.

In an embodiment of the invention, the HDMA 100 may provide a reporting capability that may facilitate generating an Electronic Medicine Administration Record (e-MAR) chart. A Medicine Administration Record may include information about the patient and his/her condition (name, DOB, ID number, personal physician, allergies, general diagnosis); the name of the medication, the medication abbreviation or code, the date that the medication was started, the diagnosis/purpose/condition relevant to the medication, the strength of the medication, the dosage form (e.g. pills, drops, ointment, other), the dose, the route of administration (mouth, ear, eye, intravenous, etc.), the frequency of administration, the prescribed administration times, the length of time that the prescription is to be given, and any special precautions or contraindications; name of person administering medication; and a chart of medication over time. The e-MAR chart may be configured by accessing one or more databases (e.g. E-EHR, outcome database, and the like as shown in FIG. 1) having information from a plurality of reporting sources. In an embodiment of the invention, the reporting sources may include, without limitation, the prescription management facility 106, the medication administration facility 110, the patient attributes and outcomes facility 112, the E-EHR facility 118, and other medical information and patient care facilities. In an embodiment of the invention, the e-MAR chart may depict data that is directly aggregated from the prescription management facility 106 and the medication administration facility 110. Further, when a health specialist or a physician enters a medical prescription through the electronic order facility provided by the prescribing facility 154, certain of that medical prescription data may get recorded into an e-MAR chart, for example contraindications and duration of prescription. The e-MAR chart may also be updated with medical prescription validation data that may be obtained in real time for the patient from aspects of the HPDMA 100, such as the marking and dispensing facility 104.

The invention allows for a typical MAR to be enhanced with additional information. In embodiments, the e-MAR chart may further depict a record of the time at which the nurse is notified about the medication for the patient, where the medication is available and when the nurse was informed. The medication may be available at the floor, the wing or the online medication cart. After the medication is made available, the nurse may scan the barcode labels to obtain information about the medication dosage, time for medication, frequency of the medication and the like. The nurse may compare the image of the patient in the system with the image obtained from the bar code data. This comparison may confirm the patient for which the medication has been received. All these activities performed by the nurse after obtaining the medication may get recorded in the e-MAR chart. The warnings or alerts that the nurse may receive upon scanning the barcode may also get recorded in the e-MAR chart. The alerts and warnings may be for a particular drug allergy or reactions and the like. The e-MAR chart may also include a record of the medication administered by the nurse to the patient. Further, the e-MAR chart may include a record of the forms filled by the nurses while administering to the patient. In an embodiment of the invention, the recorded data in the e-MAR chart may be used to populate the patient's health records in the E-EHR facility 118. In another embodiment of the invention, the recorded data in the e-MAR chart may be used to populate the MDS.

In another embodiment of the invention, the HPDMA 100 may provide an Electronic Treatment Authorization Request (e-TAR) form. The e-TAR form may allow authorization requests to be created and updated online. Enquires related to authorizations and responses for requests made may also be conducted online. These online activities may provide more accurate diagnosis code and may also provide accurate billing codes. Further in an embodiment of the invention, the data in the e-TAR form may be pulled in to the prescription management facility 106. The physician or the health specialist may utilize the authorization details filled for certain types of drugs and treatments while prescribing the medication and treatment for the patient. In another embodiment of the invention, the details filled in the e-TAR form may be recorded as the EHR of the patient in E-EHR facility 118. In yet another embodiment of the invention, the details filled in the e-TAR form may be utilized to populate the MDS.

In another embodiment of the invention TAR's are treatment administration records and are created by assimilating the data relative to the treatment of the patient (which as described herein is collected in various ways including automatically via various sources). Due to the system having the various facilities described herein, which are (in embodiments) in real-time communication with one another, typical information collected about the treatment of a patient can be continually updated into a TAR. In this manner, TAR's accessible through the system are always current and need not be assembled retroactively as is the case with most MARs and TARs currently.

Further in an embodiment of the invention, the HPDMA 100 may facilitate providing charts for recording subsets of data, such as a vital signs chart for depicting the vital signs of the patient during administration. The different vital signs of the patient may include, without limitations, body temperature, pulse rate (or heart rate), blood pressure and respiratory rate. These vital signs associated with patient may be measured by the health specialist using the technology enabled automatic data collection devices described herein that may automatically collect and/or generate data suitable for displaying a vital signs chart.

Further in an embodiment of the invention, the HPDMA 100 may facilitate providing charts for recording specialized assessments through the use of the real-time data collection and transfer capabilities described in reference to FIG. 1 (e.g. laboratory and/or therapeutic services, and the like).

Report generation, dashboard interfaces, and the like may provide essential means for accessing, managing, and using the information that may be collected throughout the electronic real time medical information collection and processing system depicted in FIG. 1. Report generation and dashboard capabilities may be provided by dashboard facility 150 depicted in FIG. 1. As depicted in FIG. 1, the dashboard facility 150 may be communicatively coupled in real time with any of the facilities show including the group of facilities within the prescription administration facilities 110, the prescription management facilities 106, and any other facility depicted.

The real time reporting facilities may generate reports by obtaining data from any of a plurality of data sources, such as the sources depicted in FIG. 1. Dashboards as may be supported by the real time reporting facilities may also be used to display the obtained data in a coherent format that may allow viewing a wide variety of important patient related information, such as the identity of a patient, the personnel who cared for or who are responsible for a patient, medical history and prognosis, medications prescribed, medications that needed to be returned or destroyed, costs associated with medications that were not covered or only partially covered by a payer, costs associated with medications for which the health care facility had to pay, and the like. The real time reporting facility may also provide up to the minute, time-based summary information regarding the above parameters and any of the associated parameters. Such information may be presented to a medical professional through a graphical user interface with text, graphics, charts, images, audio, and the like. In an embodiment, the graphical user interface may be associated with a computing device including, a mobile device, a PDA, a laptop, a smartphone and the like, In an embodiment of the invention, the real time reporting facility may provide a Long Term Care (LTC) administrator dashboard. The LTC administrator dashboard may be utilized to manage and plan the records and medication of patients that require long term care. An LTC administrator dashboard may include the facility configured to access a database having information from a plurality of reporting sources. In an exemplary case, the reporting sources may include the prescription management facility 106, the medication billing and dispensing facility, the medication dispensing machine, the medication administration facility, and an electronic health records facility. The LTC administrator dashboard may also include a user selectable dashboard definer configured to provide user selectable options for defining the information from the facility to be presented in a report at the dashboard. The LTC administrator dashboard may further include a display definer configured to operate in conjunction with the user selectable dashboard definer to define the format in which the report from the facility is to be presented at the dashboard.

The LTC administrator dashboard may include a facility to provide the type and cost of drugs consumed by the patient in a particular time period. Variable time periods may be provided by the LTC administrator dashboard and for each selected time period the dashboard may provide the type and cost of the drugs. This facility may further provide the cost of drugs consumed by each patient in a particular selected time period. In an exemplary case, the LTC administrator dashboard may provide an interface for selecting a particular time period and a search engine for selecting a particular patient.

The LTC administrator dashboard may further provide a field for obtaining insurance or Medicare costs. Many insurance plans and Medicare do not pay for custodial care in which the patient receives assistance with activities of daily living. These activities may include dressing, bathing, using the bathroom and mobility. Thus the LTC administrator dashboard may provide information regarding the expenses that are covered by the insurance plans and also those expenses which are not covered by the insurance plans or Medicare.

Further, the LTC administrator dashboard may provide an interface for resolving issues related to reimbursements. This interface may optimize and increase the reimbursement for the care provided, and reduce the non-reimbursed items for the patient and the facility. In an exemplary case, the dashboard may keep track of reimbursements for Part A services and Part B services for Medicare as well as services that have not been reimbursed.

The LTC administrator dashboard may also provide an interface to obtain and update the status of bed occupancy. The interface may provide options to select a bed and a room for the LTC patient. This may also support editing the patient's room information, putting a bed on hold status for the patient, maintaining the process of room/bed numbers as well as assigning the wing/unit to those rooms/beds. Further, LTC administrator dashboard may provide recalculations for differences in cost of beds when a patient has been moved from one bed to another in the same facility. Recalculations may also be needed when the bed is used in different shifts by the same or different patients; e.g. a patient may need the bed in the morning for dialysis and in the evening for another related treatment.

The LTC administrator dashboard may provide a field for maintaining drug utilization records. For instance, the LTC administrator dashboard may record the specific drug used by the patient in a particular medical condition, along with details of dosage, time period during which drug was administered, reactions or side effects of the said drug, resulting change in medication, improved or deteriorated condition of patient after using that specific drug, and the like. Further, the dashboard may provide such an interface for each patient in the facility.

In another embodiment of the invention, the real time reporting facility may provide an LTC facility specific dashboard. The LTC facility specific dashboard may be utilized for specific treatments and facilities that may be provided to the patients in long term care. The LTC facility specific dashboard may include an interface for obtaining Electronic-Medication Administration Record (e-MAR, embodiments of which have been described above) corresponding to a patient. The interface may provide the report that may serve as a legal record of the drugs administered to the patient at a particular facility by the nurse or any other healthcare professional. The nurse or healthcare professional may sign on the e-MAR at the time that the drug or device is administered. An e-TAR report may also document that the treatment that has been provided to the patient.

The LTC facility specific dashboard may also provide a field for maintaining billing and claim records. This field may calculate and provide bills corresponding to each patient for a desired time period. The field may also provide preview of the monthly bills for a particular patient.

The LTC facility specific dashboard may further provide a field for providing the EHR, MAR, or any other data collected or stored by the facilities described herein corresponding to individual patients or group of patients. Data may include a range of data in comprehensive or summary form, including demographics, medical history, medication and allergies, immunization status, laboratory test results, radiology images, and billing information.

The LTC facility specific dashboard may also include an electronic order facility. The electronic order facility may include an interface for aiding an individual to a health care facility to enter electronic medication, treatment and other orders. The system in certain conditions may require additional identification methods to uniquely identify, record, and document the care giver entering the orders.

The LTC facility specific dashboard may further include a facility for tracking the care plan and clinical outcome of the patient. With this facility, the user may be able to track the current care plan of the patient in run time. The facility may also allow the user to track the clinical outcome of the patient. This facility may provide the updated information of the care plan and the clinical outcome.

Further, the LTC facility specific dashboard may also provide a field to interchange the therapeutic data related to a patient or a group of patients. This field may identify the most cost effective drug for a based on the margin for a facility availed by the patient. The field may also suggest a preferred list of drugs for a particular medication for the patient. This preference may depend on several factors including availability of the drugs, cost and the like. Further in cases of emergencies, the field may also suggest or change a particular medication with blanket approvals. This may be useful as it may reduce cycle time for taking approvals from individual doctors, other physicians and pharmacists.

The LTC facility specific dashboard may further provide a field for choosing the non-formulary drugs. The field may further help the user to note a drug if the ordered medication is on the formulary.

This dashboard may display data (which is collected in real-time and which is continuously updated) about the medications that are being prescribed and administered to each patient as well as any other data collected by the system. It can be broken down by facility, floor, wing, groups of facilities, etc. It can be broken down by patient. The LTC administrator can also view a dashboard of the costs of the medications that a patient is taking, the amount of reimbursement the LTC will receive for the meds, the payment history of the patient, and the like. The dashboard provides the LTC administrator with the ability to can examiner such things as: the most costly med, the most costly patient (in terms of meds administered and prescribed), what nurse administers the most medications. Any information collected by the system can be selected and group according to user preference and/or preselected parameters of patient, facility, floor, wing, groups of facilities, attendant staff, dose, cost, reimbursed amount from patient, insurance or any government program. This information may assist the LTC admin in making operational decision regarding such things as therapeutic equivalents, staff, and other facility needs.

In an embodiment of the invention, the real time reporting facility may be useful for monitoring automated real time surveillance or public safety monitoring. In an example, a dashboard may be useful for monitoring surveillance activities related to bioterrorism or epidemics. For instance, when the number of patients suffering from a particular disease significantly exceeds a normal occurrence number, a monitoring dashboard may be updated by the real time surveillance facility to display a potential indication of an outbreak of an epidemic. This information could prove to be invaluable in implementing preventive measures in a timely manner.

Further in an embodiment of an invention, the real time reporting facility may provide dashboards for a wide variety of uses and needs for different users to generate different kinds of reports and manage various facilities. In an exemplary case, the dashboards available may include a specialist dashboard, a clinical outcome dashboard, a Long Term Health Care (LTC) administrator dashboard, a LTC facility specific dashboard, a pharmacist dashboard, various planning dashboards, prescription management dashboards, and the like. Each different dashboard may have different looks that may be represented by data entry or display fields or tabs. The dashboards may be populated in real time with the data from any of the facilities depicted in FIG. 1 including the E-EHR/E-EMR facility 118 that may also be updated in real time with patient healthcare related event data from any of the electronic real time data collection facilities depicted in FIG. 1. In an example, the patient healthcare related event data may include administration events, treatment outcomes and patient touch points. Further, the dashboards may include tracking facility (not shown in figure) that may track and organize the information on the care and cost being spent on the patients and correlate it to previous/subsequent medical treatments.

Dashboards for specialists who are monitoring a patient such as a neurological physician, an endocrinologist, a cardiologist and a general physician may facilitate the collection and analysis of various tests, procedures, observations, and the like that may be conducted by or ordered by a specialist. Inputs from each of these representative specialists may be collated in a single report that each specialist may view through a specialist dashboard. By being able to view real time information about the patient, events, outcomes, tests, and the like, a medical specialist may provide inputs for further medication of the patient (e.g. remotely).

Further, dashboards may be utilized to manage care planning Care planning dashboards may include a facility configured to access a database having information from a plurality of reporting sources, such as those sources depicted in FIG. 1 including, without limitation the prescription management facility 106, the medication administration facility 110, patient attributes and outcomes 112, an Enhanced Electronic Health Records (E-EHR) facility 118, and other medical information and patient care facilities. A care planning dashboard may also facilitate preparing different care plans for different patients. The care plans for any patient may be based on the needs of the patients that may be ascertained from profile information or medical history. For example, an over-weight patient may be offered a weight reduction care plan. Similarly, a person with high systolic blood pressure may be offered a care plan that emphasizes exercise and restricted food regime for controlling the blood pressure, and the like.

Dashboards may also be found in association with a clinical outcome facility that may record anecdotal and empirical data related to the patient care. A clinical outcome dashboard may further include a user selectable dashboard definer configured to provide user selectable options for defining the information associated with the clinical outcome facility to be presented in a report such as on a display of the dashboard. The dashboard may also include a display definer configured to operate in conjunction with the user selectable dashboard definer to define the format in which the report from the clinical outcome facility is to be presented at the dashboard.

The clinical outcomes dashboard may allow managing outcome data such as the patient's information from various sources and may include a diagnosis details, a history of the patient and related past clinical outcomes. Any information in the clinical outcome facility that may be managed by the clinical outcome dashboard may have been collected automatically, such as by using multiple sensors at a variety of patient medical information touch points including the prescription management facility 106 (e.g. the dispensing and marking facility), the prescription administration facility 110, the outcome events facility 114, an external data source not shown in FIG. 1, and the like.

The clinical outcome dashboard may further provide fields to group the patients. The patients may be grouped on the basis of their prognosis, medication, treatment, attending support staff, doctor in charge, location of the patient, facility personnel associated/responsible with the patient, and the like.

The clinical outcome dashboard may allow the user to input test results of the clinical outcomes for different patients. In an exemplary case, the dashboard may provide a menu of the different tests that may be prescribed based on the diagnostic outcome. The different tests may include lipid profile, glucose test, blood test, sodium test, potassium test, liver function test or some other type of medical tests. The dashboard may further update these test results in real time.

The clinical outcome dashboard may further provide an interface to obtain data from the prescription administration facility 110. This data may include information about the type of medication given to the patient, the time of administration, the amount of dosage, reactions and the like. Data at the medication administration facility may be updated in the real time and thereafter the updated data may reflect on the dashboard.

The clinical outcome dashboard may further describe different types of therapies that may be relevant to the patients' condition. The different therapies may include Chemotherapy, Physiotherapy, Surgical Intervention, Post-operative therapy, Integrative Therapy, Cognitive Behavioral Therapy, Psychodynamic, Developmental Therapy, and the like.

Based on the outcomes of the clinical tests, the clinical outcome dashboard may provide or suggest new therapies or drugs for the patients. In an example, if a patient is a diabetic and after the clinical outcome it is identified that the patient also has heart problems, then the dashboard may suggest a different drug for the patient. Similar logic may be applied by the dashboard with regard to therapies. In an embodiment of the invention, the dashboard may apply a clinical algorithm tool to suggest new therapies and drugs. For instance, a patient with a history of high blood pressure and newly diagnosed with high diabetes may not be prescribed the same medication as another patient who only suffers from borderline diabetes.

The clinical outcome dashboard may further provide interface to change the medication dosage of the patient. The change in dosage could occur as an outcome of clinical trials on the patient. This change will be communicated in the network and accordingly instructions will be sent to the pharmacy. For instance, a high blood pressure patient being treated with a specific drug may require a change after it is found that he has developed a persistent cough on account of that drug.

Further, the clinical outcome dashboard may allow the user to segment the outcomes according to different fields. These fields may be age of the patient, type of disease among patients, the medication given to the patients and the like.

In yet another embodiment of the invention, the real time reporting facility may provide a pharmacist dashboard. The pharmacist dashboard may provide different fields to a pharmacist while the medication is being verified and is being dispensed from the pharmacy. The pharmacist dashboard may provide a field for viewing the placed electronic orders.

The pharmacist dashboard may further provide a field to track the data corresponding to patient. This data may be utilized while verifying or altering the medications for patients.

The pharmacist dashboard may also provide a field to receive and track the therapeutic interchanges for a patient for which the blanket approvals have been provided.

The pharmacist dashboard may further provide tools and analytics to a pharmacist to provide a better medication to the patient. These tools may suggest drugs and therapies to the pharmacist for the patient. The tools and analytics may apply some algorithms and utilize past data, past history of the patient, clinical outcomes, and the like to provide these suggestions to the pharmacist.

In accordance with an embodiment of the present invention, physician ordering facility may be provided for administering and managing physician's prescribing practices for a variety of functions, and specifically for a patient care function.

The physician ordering facility may utilize significant data about the patient care from the history or previous records. The data may include prescribing practices administered for predicting or diagnosing a specific user in real time. The patient care records may include variety of information fields such as demographics, medical history, medication and allergies, immunization status, laboratory test results, radiology images, billing information, and the like.

Information from the Electronic Health/Medical Record (EHR/EMR) may be utilized either standalone or in combination with other data by the physician ordering facility. For example, a user in case of emergency may be admitted in a hospital in Chicago, while on a business trip. The identification number of user may be used to access information from the EHR regarding the existing health conditions, past prescriptions, and any special needs may be accessed from his home town (for example, Kansas City). This may facilitate immediate and effective medical response for the user.

In an embodiment, the data from the EHR may be combined with the aggregated data from third parties such as FDA regulation data. The combined data may be further processed along with real time pharmacy data (for example, from the closest neighborhood pharmacy or drug store) to obtain relevant prescription information for the patient.

In accordance with an embodiment of the present invention, the information from the EHR/EMR may be used to populate the various fields of dashboards and similar other graphical interfaces. Examples of such dashboards may include clinical outcomes dashboard, long term care administrator dashboard, long term care facility specific dashboard, pharmacist dashboard, physician ordering facility dashboard, and the like. These dashboards have been explained in conjunction with various examples earlier in the description.

For creating fields corresponding to clinical outcomes dashboard, information or documentation such as physician, nurse, and other clinician notes, flow sheets, pre-operative notes, transcriptions, medical records abstracts, advanced directives, living wills, procedural consents, medical chat records, physiological monitoring outcomes, and the like from the EHR may be utilized.

In accordance with other embodiments of the present invention, administration, nursing, laboratory, clinical, and radiology etc. Data may be used in combination with the pharmacy data to generate fields, tabs, menu, or interface for dashboards.

In embodiments, the data may be a combination of system data, system metadata, system patient information, contextual data or some other type of data.

The administrative data may include information related to registrations, admissions, discharge, transfer (RADT) data. The EHR may include levels of information regarding patient (e.g., name, demographics, next of kin, employer information, chief complaint, patient disposition.)

The laboratory data may include orders, results from laboratory instruments, schedules, billing, and other administrative information. Similarly, radiology data may include patient radiology data (e.g., orders, interpretations, patient identification information), and images information.

Information for dashboard fields may also be obtained from traditional patient records such as progress notes, reports, medications, and orders of diagnostic patient data such as medical images, electrocardiograms, scanned documents, and the like. In embodiments, information from traditional medical records may be directly utilized for generating the field codes for various dashboards.

In other embodiments, information from traditional records may be first recorded in electronic form such as in EHR/EMR and may be subsequently utilized by the dashboards.

For example, physician's scribbling and notes (e.g., response of a patient with a disjointed shoulder pain) in a hospital facility during a visit may be entered manually into an electronic database (e.g., spreadsheet). This information may be used to generate or populate a field code 'motor nerve response' in the dashboard in the drill-down view.

In accordance with an embodiment of the present invention, the content may be uploaded in the EMR/EHR in real time from various sources. Examples of sources may include patient's attribute events, prescriptions, care planning, long term, laboratory data, and the like.

In accordance with an embodiment, EHR/EMR data may be utilized for administrating care planning facility. In addition, this data may be utilized to create an interface for care planning and management by healthcare professionals and staff Data from electronic records that may be utilized for care planning and administration may include information on office visits, emergency rooms, hospital-in patients, hospital out-patients, rehabilitation, long term care facilities for care planning and nursing, and the like.

For example, information collected from EHRs of a number of patients may indicate a growth in number of caretakers who stay with the patients. In light of this information, the administrative dashboards may be designed to include field codes related to preferences for caretakers of patients (e.g., meal choices, special needs).

Similarly, the information from EHR regarding special needs of a patient under long term care and observations may be updated and made available in real time to the nursing staff.

Care plan for an emergency room may be intensive and focused. Multidisciplinary team of experts may be deployed in the ER areas to meet the variety of situations. In addition, individualized care plans may be developed for an emergency department.

Similarly, care plan for a rehabilitation center may focus on a number of parameters such as background needs of the patient, medical equipment needs, home healthcare environment needs, nutrition, supply, commodities, education & training, and the like.

Also, the needs of inpatients and outpatients may be different, emphasizing the need for different care plans for both of them. Inpatients may require nutritional and daily care (temporary) support such as bathing or dressing while outpatients may prefer a short queuing time for medications and check-up.

Maternity wards may also require a well designed care planning; for example, requirement for a hygienic and separate ward for newborns and those with special needs.

All the needs described above may be carefully administered by utilizing the data from the electronic records, existing medical and hospital records.

In accordance with an embodiment of the present invention, information from electronic health/medical records may also be used for facility planning and operations.

Information from electronic health/medical records may be related to the mix ratio of inpatient and outpatient services, older and critically sick patient population, treatment patterns, advancement in technology, health data related to diseases and conditions (asthma, cholesterol, diabetes, heart disease, hypertension, obesity, and the like), type of healthcare (ambulatory services, ER visits, and the like), data related to injuries (accidents, suicides, homicides, and the like), life stages and population (births, deaths, women's health, children's health, state and territorial distribution, and the like.), lifestyle (drug use, smoking, exercise, and the like).

In embodiments, the in-patient data from EHR may include the number of patients under 'critical conditions.' In such cases, the facility planning in terms of resource allocation, forecasting, scheduling, and the like may be performed effectively.

Similarly, non-patient aggregated EHR content such as for people accompanying the patients may be used to design the facility operations. For example, a number of wait-in chairs, automatic dispensers for basic utilities, coffee vending machines, and the like may be installed in a given facility to cater to the needs of the caretakers.

EHR/EMR data may also be helpful in planning facility operations with regard to medication supply management. For example, data from aggregated health records may be collected and analyzed periodically to assess information fields corresponding to medications. In case the records indicate high consumption patterns for Zyprexa for schizophrenic symptoms, the medication supply management system may collaborate with the pharma planning facility to identify drugs that may be less expensive and may be used as a substitute for Zyprexa.

Similarly, in case the records indicate that drugs containing ibuprofen composition do not show high efficacy in a particular group of individuals, substitutes such as herbal substitutes or any other drug composition may be introduced in the medications supply.

Facility design may facilitate smooth flow of medication supply chain. A separate section or layout may be designed for provision of medicines and other health related equipments and aids such as belts, bandages, syringes, and the like.

In accordance with an embodiment of the present invention, these medicine counters may also be self-help desk counters or online kiosks. Provision of such medication centers may facilitate smooth workflow for patients, administrators, guardians, etc.; they may be effective due to reduction in time between diagnosis and administration of medicines, and may be cost effective. In addition, it may also reduce the problems associated with non-availability of certain medications outside the hospital premises.

In another embodiment of the present invention, enhanced electronic health and medical records data may be utilized to plan new services for the healthcare facility. The aggregated data collected from E-EHRs may indicate that healthcare services may need to be revamped and redesigned in order to facilitate growth. For example, performance indicators in a rehabilitation center with regard to information dispersed on the helpdesk may be collected and analyzed. In case the results obtained from the collected data indicate that approximately 65 percent of elderly people were not able to follow instructions provided at the helpdesk, it may indicate a need for improvements in the services (such as requirement of hearing aids and friendly visual signage on the helpdesk.)

Similarly, data collected from E-EHRs may be used to plan for subscriber preferences. For example, 'energy drink preference' field codes of an E-EHR may indicate that more number of individuals prefer 'Drink X' over 'Drink Y' suggesting that more number of vending machines with 'Drink X' may be installed. As an alternate example, two subscribers providing packaging cartons for medical supplies may be compared on the basis of the EHR data such that subscriber 'A' (whose packaging is found to be water proof has been consistently rated better by the healthcare professionals) may be chosen for a contractual agreement with the healthcare facility.

In an embodiment, E-EHR data may also be used for planning insurance coverage plans and insurance reimbursement processes.

For example, electronic records of a group of individuals from a family may suggest a family based insurance plan; specific information may be provided to these individuals regarding the various aspects of a family insurance plan.

In certain cases, a generic profile of patients and their caretakers saved in the electronic medical records may be utilized for providing insurance planning facilities. For example, insurance may be offered to an individual with a high risk job profile, suggested by the records for people visiting a healthcare center.

Further, E-EHR data regarding unused medications by any individual in a given period may be used for insurance processing such as payment/co-payment and reimbursement options.

In accordance with an embodiment of the present invention, electronic data or health records may also be used for financial modeling and reporting to assess performance of one or more facilities.

With regard to financial modeling, variety of data both primary and secondary information such as demographics, disease patterns and trends, market segments, demand and supply dynamics, competitive profiles, consumption patterns, and the like may be collected from the health records, along with the information about the tangible and intangible resources available with the healthcare facility. This information may be further used to design appropriate financial models with regard to healthcare business valuation, cost of capital, portfolio options, risk modeling, option pricing, and the like for the healthcare and medication management facility.

In an embodiment, the estimated costs and financial forecasts may be presented in the form of spreadsheets, reports, and other such presentation formats.

For example, financial modeling may be performed based on the data collected from health records regarding the diminishing resources or obsolescence of a technology (e.g., health records indicating a number of cases wherein a tumor was not detected in the early stages due to existing technology limitations). This activity may be helpful in justifying a future course of action for a healthcare facility (e.g., justifying new technology acquisition for ultrasound and imaging).

An enhanced electronic healthcare record (E-EHR) may be associated with the facilities of the invention as depicted in FIG. 1 and elsewhere and may exchange information (e.g. real time data) with the facilities. The E-EHR/E-EMR facility 118 may maintain a collection of health records of individuals and/or groups in a digital format that is capable of being shared across a medical facility or with external facilities electronically such as through Internet and the like. An E-EHR may include any medical related data and information, such as a medical history, allergies, pathology and laboratory test results, medical scanning reports, region and residential information, and the like.

An enhanced E-EMR (E-EMR) may be generated in association with the E-EHR/E-EMR facility 118 and may be useful in an institution such as a hospital, clinic, physician's office, nursing home/center and the like. The E-EHR/E-EMR facility 118 facility may encompass information related to care across all settings and services such as administrative, nursing, lab, clinical, radiology, pharmacy, care planning, imaging, insurance planning, facility planning, rehabilitation, and the like without limitations. An electronic communication interface for implementing retrieval of information by the E-EHR/E-EMR facility 118 and push-out of information from the E-EHR/E-EMR facility 118 may be provided thereby facilitating utilization of E-EHR related information anywhere within an entire medical facility. For example, lab reports of a patient stored in an E-EHR/E-EMR facility 118 may be utilized during care planning to prepare a healthcare plan for a patient. Similarly, data related to allergies and sensitivities for a patient may be utilized by a doctor to prescribe relevant medicine and offer treatment accordingly. The E-EHR/E-EMR facility 118 may interconnect electronically with a variety of medical related facilities (e.g. those within and without a central facility, those depicted in FIG. 1, and the like) thereby forming a networked system where medical information of a patient or a group of patients flows in real time.

The E-EHR/E-EMR facility 118 may capture information from existing medical records as well as third party data sources. The electronic health facility may be connected with various other facilities for data collection using sensing and monitoring devices. For example, updates regarding relevant information from other facilities may be sensed by sensing and monitoring techniques and automatically delivered to be updated with the E-EHR. In embodiments, delivery and receipt of information may be facilitated through wireless methods of communication. Similarly, any information from the E-EHR may also be retrieved by other facilities though wireless communication. In an embodiment, RSS data feed may be utilized to automatically retrieve information for an update with the E-EHR.

In accordance with an embodiment of the present invention, the E-EHR/E-EMR facility 118 may include an automated data discovery mechanism for tracking and collecting data from various facilities including those depicted in FIG. 1 and within a medical facility. The data discovery mechanism may collect prescription data, caregiver data, facility data, care plan data, patient identification details, outcome data and the like. In an example, the E-EHR data discovery mechanism may form an interface with the prescription management facility 106 to detect any updates, changes, details, and the like that are provided by the prescription management facility 106 and the like. The discovered data may be used by the E-EHR/E-EMR facility 118 to update an E-EHR or E-EMR which may be accessed on demand or automatically by other facilities.

The E-EHR/E-EMR facility 118 may also organize and manage the medical-related data and information in a systematic format (e.g. sequentially). The organization and management of data by the E-EHR/E-EMR facility 118 may be based determined needs for the information by the various facilities as depicted in FIG. 1. For example, separate databases may be maintained for information related to distinct facilities, such as care planning, diagnosis, labs and imaging, and the like. In another scenario, a data management process may organize E-EHR data based on demography, patients' index, and the like. In an embodiment, data organization and management may be performed through computer implemented methods. In accordance with this scenario, data may be gathered from various packages and processed by a processing machine to map the data content into a single or multiple headers or categories. The categories may be decided by an administrator. Accordingly, based on the segregation of data content into categories, an identifier may be associated with each data item and stored in databases. The data content may further be manipulated through this identifier. Auto manipulation of data may also be performed by implementing and running a set of rules.

The E-EHR data may be analyzed and used to develop statistical models for health assessment of a group of people based on parameters such as age, geography, lifestyle and the like. The analysis and computations may be performed on overall data content. The E-EHR analysis and computation may be performed to address specific facility needs, such as care planning, labs and imaging, prescription management, insurance and payments and the like. Prescription management may benefit from E-EHR analysis by receiving an analytical result that includes at least one pharmacy-related data element in context of one or more individuals' E-EHR data.

The E-EHR analysis and computations may be performed in real-time to facilitate real-time solution exchange among the various facilities within the medical profession, such as those depicted in FIG. 1. In an example, data may be received by the E-EHR/E-EMR facility 118 for entry into an individual's E-EHR. As that E-EHR record is being updated, the data may also be analyzed to provide real-time feedback to a prescription management facility that is handling prescriptions for the individual. This real time analysis and communication may be similarly applied to the other facilities depicted in FIG. 1 and elsewhere.

In accordance with various embodiments, data security may be ensured for the E-EHR through authentication requirements. For example, a proper authentication of a user along with his personal as well as log in details may be required during access and operation of the E-EHR. In another embodiment of a fully automated tracking and record keeping facility, unique log in credentials may be provided to users who are registered with the medical facility and corresponding details of users may be gathered and stored in a separate database. Any subsequent correspondence with regard to the E-EHR from a registered user may be accompanied with certain security checks to confirm already stored details of the registered users. Further, various levels of access associated with the E-EHR may be encrypted for secured access by an authorized and intended person only. Encryption may implement an authorization protocol that may be decrypted by a specific secured key only. In an embodiment, a token may be issued to a user on any type of association with the E-EHR that may enable further processing and assist in keeping track of user operations on the E-EHR. In an embodiment, the token may be generated using an automated system in the form of an auto-email.

In accordance with various embodiments of the present invention, system data may be registered at a central location. System data may include various software algorithms, operational and support data, content of the E-EHR, respective metadata, and definitions of metadata, attributes and characteristics associated with the data content, and the like. The data content may include semantics as well as representations. Further, the registered system data may be linked with various other data sources and interfaces through pointers. The central location associating registry of the system data may be protected with data security and encryption methods where only authenticated persons may find access.

In accordance with an embodiment, various business rules may be associated with the E-EHR. These business rules may include details governing the flow of information from one facility to another. For example, delivery of drugs and medicines from the dispensing and marking facility 104 may be terminated in case billing facility reports inadequate advance payments. Business rules may be defined regarding information transfer from the E-EHR to the prescription management facility 106 or to a physician's prescribing device in case prescribed medicines are found to differ from the prescribed guidelines on a patient's E-EHR.

The E-EHR may include and maintain a patient index that may include a list that refers to all patients registered with a medical facility. The patient index may be maintained on the basis of names, geography or location of patients, type of association such as temporary or permanent or with a specific facility such as cardiac or orthopedic, and the like. It may be appreciated by a person ordinarily skilled in the art that E-EHR may be referred to by other names such as E-EMR and the like without limiting the spirit and scope of the present invention.

As explained earlier, data may be sourced from a variety of facilities, events, outcomes, actions, and the like to populate an E-EHR or E-EMR. Some sources of E-EHR data in a healthcare management facility may be related to medication and staff administration, care and emergency planning, testing and validation, regulation, delivery, and the like. Data that may be sourced from events pertaining to the administration of prescriptions may include date, time, location, dosage, prescriber, patient, medication, generic medication, type or mode of administration, undertakings, approvals, patient's mood and responsiveness (before and after administration of medication), patient's reactions after taking medication (comfort/discomfort), patient's pain perception, patient's symptom perception, response to side effects, other medications administered during same time interval, patient's vital signs, presence/absence of other entities during administration, change in patient's symptoms (e.g. improvement and/or worsening of the symptoms), and the like. In an example, in a hospital ward at least five out of ten patients are given a dose of Drug X for treating a traumatic brain injury. The reaction of patients to the drug in the form of mood swings, behavior patterns, and responsiveness may be recorded in real time and sent to the outcomes analytics or databases. This information may be further integrated with the E-EHRs of the individuals. These reactions and patterns may be observed and recorded by the healthcare professionals such as staff, nurses, attendants, and the like and may influence future course of action. These reactions and response patterns may be automatically recorded, such as with sensors for measuring changes in the blood pressure or nervous reactions of the patients may be tracked. Emotions, moods, and patient response may be detected by galvanic response sensors attached to the skin (sense arousal, fear, anxiety); heart rate sensors to sense agitation, stress, feeling of calm; Electromyogram (EMG) sensors implanted in muscle tissues to measure nervousness and relaxation; Electroencephalograph (EEG) scalp sensors for measuring brain activity; Magnetic Resonance Imagery (MRI), and the like.

Various data collection facilities may be provided for gathering prescription administration data including mobile devices such as PDAs, smart phones, tablet PCs, notebooks, and the like. Other examples are described above and elsewhere herein. These mobile devices may run on any operating system such as Windows Mobile, Windows XP, Palm, RIM and Symbian-based operating systems. These devices may be provided with data encryption, medication verification software, scanning and tracking abilities, and user interface such as a graphical user interface. In addition, these mobile devices may be equipped with various applications to aid in the data collection, entry, and analysis process related to a medical condition of the patient. Of course, the mobile devices may be provided with wired or wireless connectivity and may include scanners for scanning barcodes on medications. Alternatively, the mobile devices with an in-built barcode scanner may be provided. The barcode scanning recognition technology may capture medication data in real time and allow the staff or healthcare professionals to chart and maintain all critical patient information as they administer the medications. Examples of barcode scanners may include handheld, pen-type, laser, CCD, camera-based, omni-directional, and some other type of scanners. Alternatively the scanner may be an RFID reader for reading RFID tags on medications. The RFID data may be captured in real time and sent to the E-EMR facility for recording.

In another embodiment, data collection facilities and devices may be provided with a web interface. The web interface may be accessed via an Internet, LAN, WAN, MAN, or some other type of network. The web interface may be in the form of a dashboard. The web interface may accept an input (command, request, information, and the like) by generating web pages accessible via a web browser. The web interface may be provided with security protocols for preventing unauthorized access. Alternately, data collection may be performed using a web application that may run on a SaaS-based architecture. The access credentials such as login information may be shared with the users (nurses, staff, administrators, and the like.) for downloading and accessing the application over the Internet. Upon accessing the application, a user interface/dashboard/panel with a variety of select options in the form of tabs, menus, dropdown lists, and the like may be provided to the user. Following this, the user may enter the medication administration event data for one or more patients.

In accordance with an embodiment of the present invention, data collection may be facilitated via automatically generated signals from tangible products such as medication supplies (medicines, bandages, packets, and the like), nutritional food packages, and the like. In embodiments, the medication supplies and packages may be equipped with sensors, RFID sensors, tracking equipments, and the like for detecting signals. For example, opening a glucose bottle may send this information to a data collection facility for further processing. The information may include packaging date, manufacturing or batch number, manufacturer's name and code, retail price, and other similar details to the data collection facility. Similarly, opening a packet of syringes or band-aids may signal the event information to the data collection facility. In embodiments, this information in combination with the location or spatial information such as GPRS information may be used for tracking complete real time event information.

Data may also be collected based on the observation recorded via a web or vigilance camera. The camera may be a mobile camera.

Data pertaining to events may be recorded, such as a conversation between a healthcare professional and a patient. With proper technology enabled devices, voice records may also be converted into digital/EHRs.

Further, data may be collected from existing patient records. In an embodiment, data from manual, hard copy records may be transcribed. In certain cases, event dating may be provided to the transcribed data for the purpose of records.

In accordance with another embodiment, data from E-EHR/E-EMR facility 118 may be accessed by other facilities such as care planning, rehabilitation, long term care facility, and the like, through an E-EHR SaaS service.

Data in an E-EHR may also be managed manually, such as through a user interface. E-EHR patient management user interfaces may be provided with various functional fields to add a patient, discharge a patient, and edit patient's (demographics, room number, allergy, diagnosis, and the like) information. In an example, a change in the room number information for a patient may be sent in real time and updated in the patient's E-EHR.

Various facilities may interact with each other such that the real time data flows among them. For example, data from the administrative touch points (such as from a hospital ward) may be collected and shared with the other facilities such as care planning, billing, E-EMRs and the like.

The flow of data may be bi-directional between the facilities, i.e., the data flow may be backward compatible. For example, data sent from the patient's care department to the orthopedic department may reflect multiple incidences of fractures; this information may indicate osteoporosis and a bone density test may be advised by the orthopedic department along with a blood test to the care department with instructions indicating fragility of patient's bones and advocating due care.

E-EHR may include data that may be related to financial transactions such as billing, payment, insurance, and the like. For example, a patient may be undergoing a test in a laboratory. Real time information about the nature of test may be broadcasted to the billing facility where an automatic receipt may be generated indicating the amount to be paid by the patient based on the insurance coverage availed by him (the insurance information may be obtained in real time from the insurance facility).

Similarly, real time data from patient touch points such as patient attributes/events facility may be utilized for various insurance processing activities such as determining submittal process and norms, eligibility benefits, coverage response, and the like. Specifically for coverage response, real time data from patient touch points may be used to ascertain events such as if a given treatment/medicine is covered under an exceptional case, or if it requires certain prerequisite events or conditions.

Likewise for payment options, real time patient E-EHR data may be used for establishing conditions or procedures for co-payment and reimbursement for unused medications.

E-EHR data collection may be related to new prescription events. In an embodiment, data tracked in an E-EHR for a new prescription by a doctor may include various aspects of the medications such as brands, allowability for substituting generics, dosage frequency/quantity, administration schedule and/or requirements, durable goods, rehabilitation requirements (treatment/therapy), and the like.

Data that may be stored with an E-EHR/E-EMR facility 118 (e.g. in an E-EHR) may also be collected from electronic orange book (maintained by United States Food and Drug Administration) regarding new information on approved drug products, generics, proprietary name info, applicants/owners, legal protection, and therapeutic equivalents. This information when made available in a patient E-EHR may be updated in real time and the updated information may be reflected in the markings on packaging of medications; for example, information regarding the mode of consumption, sun exposure, and the like may be printed on the label of a medication bottle.

Data pertaining to new events may be shared with the pharmacies and treatment and care centers such as long term care and rehabilitation centers. In addition, the collected data may be used to manage dispensing/supply chain operations at the pharmacy. For example, a real time data collected for increased number of cases for stomach flu may help the pharmacy schedule its delivery side operations proactively. Similarly, data pertaining to transactions for purchasing medications at the pharmacy windows may also be tracked.

Pharmacy-related data tracking may include home delivery orders for a mail order pharmacy may be tracked and recorded in the E-EHR in real time (e.g. shipment from the pharmacy, in-route tracking, delivery, and the like)

The E-EHR may also receive data pertaining to patient-specific clinical outcomes from various sources such as laboratories, imaging facility, regulatory facilities, third parties, and the like. Outcome data may be provided electronically from computerized systems associated with the facilities or with an individual patient (e.g. web-based data entry by a patient). Clinical outcome data may include real time data collected from laboratory and imaging services such as tests requested, intake notes, medical samples, electronic measurements, clinician readings of results and notes, primary or specialists care reading and notes, and the like.

Patient touch points may include the facilities and facility in the healthcare management platform where real time event tracking concerning various aspects of medical care may be conducted. Personal records and documentation from these touch points may include information such as capacity planning (number and details regarding people working in the facility), time-in and time-out management for employees and staff, and some other types of information Clinical outcomes may be a form of patient touch point, but other data from other patient touch points may also be captured by the E-EHR/E-EMR facility 118. Patient interviews, a common healthcare practice, may include data that can be captured (e.g. in real time) and delivered to the E-EHR (or to other facilities as described herein). For example, conversations between a patient and a rehabilitation specialist may be captured in the E-EHR (in the form of handwritten notes, short-hand writings, graphical symbols, voice recordings, and the like). Likewise, statistical information (e.g. vital signs) such as body temperature, pulse rate, blood pressure, respiratory rate, and the like may also be collected in real time from patient touch points. Collection of vital signs information may be a pre or post prescription administration activity.

Real time data collection from patient touch points may be used for improved pharmacy management in other ways including patient-specific medication review when a prescription is received in the prescription management facility 106. As an example, a patient's E-EHR may indicate that the patient is being administered a daily dose of ranitidine for treatment of a peptic ulcer. The pharmacy management facility may receive a new prescription for the patient for 'nizatidine'. The new prescription information may trigger the pharmacy management facility to retrieve the pertinent portion of the patient's E-EHR to perform validation, generic selection, and the like based on this information along with the patient's condition(s), aptness, and potential side effects of these medicines. The result may determine the course of prescription for the patient. Further, real time patient response for different treatments and/or medications may be stored as an E-EMR record and may be used to provide feedback for pharmacy development. For example, a response from a number of patients regarding taste of a medicine may be provided as a feedback to the concerned drug manufacturer.

E-EHRs may be maintained for easy, authentic and reliable access. In an embodiment, the movement, adequate storage requirements, and storage location of health records (e.g. in an E-EHR or E-EMR) may be controlled to ensure that records may be accessed in real time and at any given time. E-EHR maintenance may include a records recovery solution. Other E-EHR maintenance activities may support audit trail periodic evaluation. Further, various control measures such as access monitoring, user verification, authorized destruction and security controls may be introduced to prevent unauthorized access, destruction, alteration or removal or records, and the like.

Because individual facilities may choose to maintain portions of patient records locally (or at least maintain certain information separately from a comprehensive E-EHR) the E-EHR/E-EMR facility 118 may facilitate ensuring data integrity across all the records at all the locations. For example, if a person changes his/her contact address in the records of the care planning facility, it may be validated through the E-EHR/E-EMR facility 118 to ensure that the information is accurate. The representative at the care planning facility receiving the new contact address information may confirm with the patient that this information should be applied to all of the patient's medical records before signaling to the E-EHR to apply the change to the E-EHR database.

Data from E-EMR/EHR may also be combined with other non-E-EHR data such as clinical studies, drug interactions and company data, and the like to facilitate a well informed decision process making by the concerned healthcare professionals and/or entities. For example, allergy information for a patient profile may be combined with the real time pharmacy information on substitutes to validate the prescribed medications for the patient.

When combined with other data, E-EHR data may be used in a variety of ways including creating prescription guidelines for physicians and the attendants, determining the potential outcomes of a prescribed medication/treatment administration. The potential outcomes may be useful for avoiding adverse medication's reactions or interactions, customizing dose in accordance with patient perceptions, identifying ineffective medications for particular patients, identifying patient profiles for high effectiveness of medications, treating co-morbidity, identifying unexpected benefits from unrelated conditions, linking perceived/actual benefits of medications to other factors, and the like. For example, a pain perception with medication administration may be dependent on other factors such as alertness, physical activity, entertainment, mood, and the like.

Further, the E-EHR may include information about a patient's daily life (e.g. information on the nutrition, activity, exercise, sleep patterns, and the like) which may be used during any subsequent patient touch point. The E-EHR with this diversity of information, including real time information as described herein may be useful for a more comprehensive assessment of the patient, such as during an emergency by EMTs, the emergency room nurses, and other medical care professionals.

As discussed earlier, E-EHR/E-EMR data may also be useful for insurance planning Real time information regarding the purchase/modification/renewal of health policies for a patient may be updated in the records. Based on the records of an individual regarding his own and family's needs, an insurance plan may be offered to him. Alternatively, consolidation of E-EHR data from a plurality of patients while maintaining confidentially of the patients may benefit an insurance planning activity that may relate to plans, coverage, rates, costs, payment processing, and the like.

Real time health care data from electronic records (e.g. EHR) may be advantageous for management and operation of a long term care facility. Individual E-EHRs may be accessed to determine eligibility for treatment in the facility, specialists and/or equipment that would be needed at the facility to support the individual, and the like. Consolidated E-EHR data may help with planning of facility expansion, professional recruiting, and the like.

In embodiments, real time data from enhanced E-EHRs may be utilitarian for a physician or specialist with regard to prescribing treatment and care. The dynamic, real time nature of the E-EHR/E-EMR facility 118 and communications depicted in FIG. 1 and described herein may benefit the use of remote specialist evaluation in real time of a patient that heretofore was unknown to the specialist by making the information in the E-EHR current, relevant, and continuously updated through the real time updating capabilities described herein. In another example, a doctor may be sensitized about the allergy conditions of a patient before prescribing medications to him/her.

The E-EHR/E-EMR facility 118 may facilitate integrating data received from various facilities including dispensing & marking facility, Rx delivery, patient events, outcome events and the like. The data may be received by the E-EHR/E-EMR facility 118 through streaming data from these and other sources. This integration may result in further improved enhanced electronic records for patients. In addition, such an enhanced record may create additional knowledge about the patient such as tendencies for certain diseases that may be inherited.

In one embodiment, the enhancement may be in the form of integration of the patient's insurance history with the medical data. In another embodiment, the integration may be of data associated with clinical trials. In yet another embodiment, the data integration may be with a pharma covigilance database, drug database, health database or some other type of health database. In yet another embodiment, E-EHR/E-EMR facility 118 facilitated data integration may enhance E-EHR and E-EMR databases by integrating them with electronic patient check-ins, access to patient records either at day or at night, instant messaging, transcription facility, payment information, scheduling of health care, electronic medical billing, claim management facility, reimbursement facility, alert facility, order tracking, archiving, reporting, and interfacing with tablet PC, PDA, Fax, scanner and the like.

The E-EHR may be in a digital format that may include data in comprehensive or summary form, such as medical history, laboratory test results, billing information, and the like.

As described herein and elsewhere the E-EHR/E-EMR facility 118 may be an application that may be implemented in distributed data storage systems that may be located at different locations so that an enhanced E-EHR for a particular patient may be fragmented at various locations based on a particular attribute of the patient data. The attributes may be associated with patient history, patient diagnosis, patient treatment and the like. In an embodiment, distributed nodes of such a database may be interconnected through a communication channel.

In accordance with various embodiments of the present invention, the enhanced E-EHR may include a data integration facility with features described herein above as well as providing users with a unified view of the data. For example, the data integration facility may feed data in real time from a variety of sources to a clinical repository that may be viewed by customers. Further, the data integration facility may enable hospitals, clinics, and the like, to share and analyze the data with other hospitals, regional health organizations, and the like. In one scenario, the data integration facility may replicate the data while loading the data into the health records and other applications. The data integration facility may also store a backup of the data in a second repository that may be used to feed the data back to the enhanced E-EHRs in real time, in case the original data is lost due to some reasons.

In another scenario, the E-EHR may include an Extraction Transformation Load (ETL) facility. The ETL facility may be used in association with the data integration facility that may enable extraction of data, such as patient data from an outside source such as lab reports, consultation reports from different clinics, and the like. Extraction from the outside source may involve converting the data into a format capable of undergoing transformation processing. Thereafter, the data may be transformed to meet technical and business requirements of a target database. For instance, word-processing data might be translated into numbers and letters, which are easier to track in a spreadsheet or database program. Finally, data may be loaded into the target database. Some databases may overwrite existing data with cumulative effect, with frequent updating of extract data being done on daily, weekly or monthly basis. Further, some databases may update the data in real time.

In an embodiment, the E-EHR may also be provided with a Statistical Analysis System (SAS). The SAS may facilitate data entry, retrieval, management and mining of the data by the users. For example, a user may enter information such as patient ID, name of a patient, and the like, for retrieving details such as billing information, medical history, and the like, about the patient from an E-EHR. The retrieved data may be manipulated by the user and may thereafter be extracted from the SAS. The SAS may also enable the user to analyze data on the basis of medical history of the patient, such as for the purpose of evaluating progress in medical conditions of the patient, and the like. In another example, the user may be able to obtain a statistical analysis of previous reports of the patient that may be stored in an E-EHR. For example, if a patient with blood group O positive needs to be administered drug Y, the SAS may enable a user such as a doctor, a nurse, and the like, to run a statistical analysis for finding the effect of the drug Y on patient records with the same blood group. Such an analysis may enable the user to find out whether the patient with blood group O positive is allergic to drug Y or not. In case an allergy is discovered, the SAS may trigger an alarm to caution a physician regarding the allergy. The physician may then replace the drug Y with another medicine that may not cause allergy in the patient. In an embodiment, the statistical analysis may be run on the basis of age of the patient, medical history of the patient, and the like.

In accordance with various embodiments of the present invention, the enhanced E-EHR may include Service Oriented Architecture (SOA) that may help healthcare-related IT organizations to improve patient treatment methods and billing techniques. The SOA may enable IT organizations to focus on improving the health information systems by removing system-to-system communication problems and by making healthcare organizations more adaptable to change. In another embodiment, the SOA may also establish architecture standards for data formats and system interfaces that may promote sharing of information. For example, instead of mapping patient demographics from an E-EHR system and each clinical system in a point-to-point fashion, the SOA may enable the E-EHR application to abstract the differences in the data and interfaces. Specifically, instead of having hundreds of point-to-point interfaces in the E-EHR, there may be only one service interface for each function that may greatly reduce complexity and maintenance costs.

In an embodiment, the E-EHR application may enable the patient-related data such as medical history, medical bills, and the like, to be transmitted or received using data streams. In embodiments, the data streams may be a communication medium that exchange data to and from the healthcare platform. E-EHR may be capable of producing a data stream that may be read by other health systems and other data management systems. Representing the patient data as a data stream may provide interoperability between systems that may support continuous care of patients who move between health care systems and facilitate merging of the patient data from multiple sites of care for regional, national, and international monitoring. Hence, the E-EHR application may include functionalities for importing and exporting data between two health care systems that may be accepted and transmitted in a standard format.

Various security measures may be taken into consideration while accessing an E-EHR. The security measures may be software based or hardware based. The patient data saved in the E-EHR may be secured by providing access control, such as password protection and network-based admission control that limits access to authorized users and devices only. Further, the security devices associated with the network may provide protection for a wide range of mobile devices that include servers, laptops, tablet PCs, and personal digital assistants (PDAs) from intrusions and outbreaks, such as worms, virus attacks, and the like.

Further, various technologies may be used by the E-EHR application for collecting the patient data for maintaining records. The records may include details such as medical history of the patient, and the like. The records may be maintained by healthcare organizations as well as by the patient. The E-EHR application may enable automatic collection of external data such as billing information, details of medical history of a patient, and the like. For example, scanned images, records, and the like, may be directly fed into a computer system of a clinic, health care organization, and the like. Examples of the technologies may include, without limitations, bar codes, radio frequency identification (RFID) technology and voice recognition. For example, bar codes may be used for capturing the external data; for instance, information of drugs being administered to a patient may be captured by a bar code reader device in real time. The captured data may be related to medicines being administered to patients. Similarly, the RFID technology may be used for the external data related to medical assets. Further, RFID technology may eliminate wastage of time that may be spent by doctors and nurses on searching for supplies and equipment, thereby leaving more time for them to attend to patients. The RFID technology may allow improvement in quality, safety, efficiency and care coordination within a hospital, a healthcare organization, and the like. Additionally, the RFID technology may also be used in real-time location tracking systems.

In an embodiment, an E-EHR application may provide voice recognition technology for collecting data related to a patient. The voice recognition technology may convert spoken words into text in real time. The data collection process using voice recognition technology may be more effective and may be performed more easily when deployed in conjunction with a voice recognition facility. For example, searches, queries, and form filling may be performed faster by voice recognition than by using a keyboard. Likewise, voice recognition technology may enable physicians to produce records and reports for patients in real time.

In accordance with various embodiments of the present invention, remote collaboration tools such as web cams, chat/internet messenger (IM), and the like, may associated with the E-EHR. For example, a web cam may enable a user to take a snap shot of a patient's physical findings, especially for dermatological conditions. The captured image may then be tagged to a medical record for monitoring progress and treatment outcomes of the patient.

In another embodiment, the E-EHR application may support access of the data related to medical history of a patient, medical insurance, and the like from a remote location by means of hand held devices such as mobile phones, PDAs, and the like. For example, physicians, clinicians, and the like, may access patient data from any entity that is capable of connecting to the network, regardless of where the records were originally stored or input. In such a scenario, the E-EHR application may store copies of the records on a server that may be accessed via a web browser. Accordingly, a user may easily access, modify or transfer the records of the patients to other hand held devices. In another example, physicians may simply log into a remote system and may retrieve the record of a patient to initiate treatment.

In yet another embodiment, the E-EHR application may be capable of providing data in real time about patient care. For example, if a patient is undergoing treatment in a hospital, the E-EHR application may enable the medical records of the patient to be updated in real time by a user such as a doctor, a nurse, and the like, based on diagnosis of the patient, medicines being administered currently to the patient, dosage of the medicines, and the like. In another example, real time connectivity between a pharmacy and a workstation of a doctor may provide information to the doctor about availability in the pharmacy of various medicines to be administered to the patient. In a similar manner, the E-EHR application may provide real time data about various treatments being conducted for a patient.

In accordance with various embodiments of the present invention, machine learning (ML) techniques may allow the E-EHR application to facilitate and enhance work of medical experts, thereby improving the efficiency and quality of medical care provided by medical experts. The ML methods may facilitate the E-EHR application to automatically recognize complex patterns and make intelligent decisions such as analysis of patient treatment data, and the like, based on data that may be already available in the E-EHR Examples. Further, the ML methods may be used to analyze clinical parameters and their combinations for prognosis, e.g. prediction of disease progression, for extraction of medical data, and the like. The ML methods may also be used for data analysis, such as interpretation of continuous data used in the Intensive Care Unit; intelligent alarming during situations that may require immediate action thereby resulting in efficient monitoring, and the like.

In a scenario, the E-EHR application may also provide assistance, such as vocal assistance, for enabling the user to operate the E-EHR application efficiently. For example, if the user encounters some problem in accessing the record of a patient, the user may take the help of the voice assistance service offered by the E-EHR application. In a scenario, the user wearing a headset device may be able to listen to the voice-based assistance and act accordingly.

Furthermore, a user may scan images of an injury, and the like, captured through handheld devices such as mobile phone camera, and the like. The E-EHR application may enable the user to scan the images and save the scanned images, along with the records of a patient. In an embodiment, the user may scan old medical documents of the patient and may save them along with new electronic data of the patient. In addition, the user may also index the scanned documents in the E-EHR based on date of birth, patient ID number, and the like.

In accordance with various embodiments of the present invention, artificial intelligence based delivery networks may help in automating the production of medical documentation. In an example, the delivery network may optimize the storage of the medical record. In another example, the delivery network may enhance the retrieval of the record. Such delivery networks may perform diagnosis and also make recommendations for therapy. For example, a representative model may depict the symptoms of stomach flu, along with typical clinical manifestations of stomach flu, such as diarrhea, high temperature, nausea and loss of appetite. Based on this symbolic model, an artificial intelligence delivery network may automatically diagnose the disease based on input of symptoms and provide advice on a course of treatment to be followed.

In another embodiment, various identification technologies such as a facial recognition system, biometrics, and the like, may be utilized by the E-EHR application for automatically identifying or verifying a user. For example, the E-EHR application may compare selected features of the person with a facial database to allow access to the record of a patient. The identification technologies may be implemented owing to the patient's right of privacy and to the need for security measures mandatory in healthcare.

The E-EHR application may set up a virtual private network (VPN) that may be used by healthcare information systems of a hospital, a healthcare organization, and the like. Healthcare organizations may face hurdles in making secure patient records and other sensitive health information due to widespread internet usage. The VPN may allow patients, doctors, medical organizations, insurance companies and government agencies, alike to communicate effectively and economically. Further, the VPN may use passwords, biometrics, two-factor authentication or other cryptographic methods for securing records of the patients. Additionally, the E-EHR application may provide secure tunnels from workstations to order entry facility. For example, a user may enter an order for medications from a workstation such as a care planning facility. The order entered by the user may be viewed in real time by a pharma planning facility. The pharma planning facility may send the order to a prescription validation facility that may facilitate in dispensing the ordered medications to a patient upon validation of the order. The information transfer between two or more workstations as described above may be done using the VPN.

Further in accordance with embodiments of the invention, the system may include a voice activated care tracker facility. This facility may allow the caregiver to track various activities through voice commands. In an exemplary embodiment, the system may store all the information relating to the patient. The caregiver may interact with the system to provide various facilities to the patient.

In an exemplary case, the tracker facility may track the charting tool. The charting tool may include an enhanced Medication Administration Record (MAR) chart. The caregiver may activate the MAR chart with the help of voice commands.

The tracker facility may also monitor the Activities of Daily Living (ADL). The ADL may include the daily life activities like feeding, bathing, dressing, grooming and the like. The caregiver may interact with the system to demand support staff for helping the patient with daily activities. In an embodiment of the invention, data related to the facilities provided for the daily activities may be utilized to populate the MDS.

The voice activated care tracker facility may further be utilized to track the medication to be dispensed to the patient. The system may have the details of medication to be given to the patient. The caregiver may confirm these details with the system before providing the medication to the patient.

The voice activated care tracker facility may further allow the caregiver to connect to the administrative or billing facility for providing billing information. There may be scenarios when a change in the medication may be required and it may be reflected in the billing details of the patient. In such a case, the caregiver with the help of voice activated care tracker facility may connect to billing facility to update this information.

The voice activated care tracker facility may further allow the caregiver to page other staff members or doctors for support in caring for the patient. There may be cases when an elderly patient may require a wheel chair for some kind of movement. The caregiver may send a paging message to the desired staff member. The desired staff member may receive this message through the system and make the wheel chair available.

In an embodiment of the invention, the caregiver may interact with the various facilities using a pair of head-phones. Further in another exemplary case, a voice activated care tracker facility of the present invention may be used with third party products such as ACCU-NURSE or CARE TRACKER.

Further in accordance with an embodiment of the invention, the medication administration data stored on the data server may be adapted to populate a Minimum Data Set (MDS). The MDS may be a part of the U.S. federally mandated process for clinical assessment of all residents in Medicare or Medicaid certified nursing homes. This process provides a comprehensive assessment of each resident's functional capabilities and helps nursing home staff identify health problems. The MDS may be populated in different ways. In an exemplary case, the MDS may be populated with data provided as per the standards of National Council for Prescription Drug Programs (NCPDP). NCPDP is any entity whose primary activities are developing, coordinating, promulgating, revising, amending, reissuing, interpreting, or otherwise maintaining standards that address the interests of a wide base of users outside the standards development organization. The membership of NCPDP provides leadership and healthcare business solutions through education and standards created using the consensus building process. NCPDP has been named in the US federal legislation, along with the Health Insurance Portability and Accountability Act and the Medicare Prescription Drug, Improvement and Modernization Act.

In another exemplary scenario, the MDS may be populated by providing data as per the standards of the Health Level Seven International (HL7) feed. The HL7 provides standards for interoperability that improve care delivery, optimize workflow, reduce ambiguity and enhance knowledge transfer among all stakeholders, including healthcare providers, government agencies, the vendor community, fellow SDOs and patients.

In yet another exemplary case, an Extensible Markup Language (XML) feed available as a web service may be captured by the MDS. The XML feed is syndication feed parser for both RSS and Atom feeds. It also implements feed auto-discovery for finding feeds, given a Uniform Resource Identifier (URI). The XML feed supports the following syndication feed formats: RSS 0.91, RSS 1.0, RSS 2.0 and Atom. The XML feed may provide a unified Application Programming Interface (API) for parsing and using the various syndication formats.

In yet another exemplary case, the MDS may be populated in the manner of Software as a service (SaaS). SaaS is a model of software deployment over the internet. With SaaS, a provider licenses an application to customers for use as a service on demand, either through a time subscription or a "pay-as-you-go" model. In yet another exemplary case, the MDS may be populated through Cloud computing. Cloud computing is Internet-based computing, whereby shared resources, software and information are provided to computers and other devices on-demand, like a public utility.

In yet another exemplary case, the MDS may be populated through a Service-Oriented Architecture (SOA). SOA is a flexible set of design principles used during the phases of systems development and integration. A deployed SOA-based architecture will provide a loosely-integrated suite of services that can be used within multiple business domains.

In yet another exemplary case, the MDS may be populated by storing data in a database using the Structured Query Language (SQL). The data may further be populated using .NET framework.

In yet another exemplary case, the MDS may be populated using Java Server Pages (JSP), Active Server Pages (ASP) or asynchronous JavaScript and XML (Ajax) front end.

The healthcare and pharmacy data management and administration platform may further be implemented in different environments. The different environments may include a Long Term Care (LTC) facility, a Skilled Nursing Facility (SNF), and the like. A LTC provides residential daily living and medical services to a patient requiring extended medical attention. Such a facility may provide rehabilitative, restorative, and/or ongoing skilled nursing care to patients or residents in need of assistance with activities of daily living. Long-term care facilities include nursing homes, rehabilitation facilities, inpatient behavioral health facilities, long-term chronic care hospitals, and the like. The SNF is a place of residence for people who require constant nursing care and have significant deficiencies with activities of daily living. The SNF may include rehabilitation and various medical and nursing procedures. In SNF, every patient is under the direct supervision and care of a physician, such that the physician may be available on an emergency basis. Further, the records of the condition and care of every patient may be maintained, nursing service may be available with at least one full-time registered nurse on duty 24 hours a day. Also, the SNF may have appropriate facilities for storing and dispensing drugs and biologics.

The healthcare and pharmacy data management and administration platform may also be implemented through an environment such as the Assisted Living Facility (ALF). An ALF may provide supervision or assistance to those living in a Residential Care Home, Assisted Care Living Facility, or a Personal Care Home; they do not need constant nursing care but need help with activities of daily living. Coordination of services by outside health care providers and monitoring of patient activities to ensure their health, safety, and well-being may also be provided. Assistance may further include the administration or supervision of medication, or personal care services provided by a trained staff person.

Further, the healthcare and pharmacy data management and administration platform may also provide assistance to patients who choose an independent living environment. In times of illness or disability due to advanced age, when managing activities of daily living becomes difficult, help may be provided in the form of limited time care by a healthcare provider who visits at specific times to perform specific jobs such as administering medication, bathing, grooming, cooking, feeding, and the like.

The healthcare and pharmacy data management and administration platform may further be applied to different environments of medication delivery. The healthcare platform may provide different tools to reduce the delivery costs of the medication. In an exemplary case, the delivery costs may be reduced by hedging the fuel or gas prices. Hedging will reduce or eliminate financial risk involved with variation in prices of gas. The healthcare platform will take two positions in the equity or commodity market that will offset each other if prices of gas change.

The healthcare and pharmacy data management and administration platform may also reduce the delivery costs by cutting down some routes. This may be achieved by identifying the routes at which less medication are delivered and are also longer. Such routes may be cut down or the frequency of delivering the medication may be reduced on these routes to save the resources.

Further, the healthcare and pharmacy data management and administration platform may apply some algorithms to identify the proximity of the delivery destinations. By identifying the proximal destinations, the healthcare platform may be able to control the frequency of delivery of medication to these destinations or may group the medication for the destinations that are close to each other.

The healthcare and pharmacy data management and administration platform may also apply Artificial Intelligence (AI) based routing tools to identify the most efficient routes. In an example, the healthcare platform may use Dijkstra's algorithm to find the shortest route.

The healthcare and pharmacy data management and administration platform may also reduce the cost of delivery in real time routing. Deliveries may be regular deliveries or may be sweep run that cover a range of delivery locations in a geographic region or locale.

The healthcare and pharmacy data management and administration platform may assist in grouping the delivery orders. The grouping may be done on the basis of the facilities provided to the patients. Patients availing the same physical facility may be grouped together and medication for the entire group may be delivered together. Orders may also be grouped on the basis of the wing occupied by the patients. Orders for patients in the same wing may be grouped together. Order may also be grouped on the basis of the time of administration of a group of patients. In an example, if the administration time for a group of patients is overlapping then the order for all those patients may be grouped together. Various other groupings are described herein and include grouping by floor, wing, section, demographic, type of medication taken, facility, group of facilities, geographic region, by attending physician, by nursing staff, and the like. For medications that have to be administered at various times throughout the day, all of a patient's daily medication may be grouped by administration time and delivered for a specific patient to a location from which a healthcare provider can pull the medication at the required time. For a group of patients receiving medications throughout the day, the medication may be grouped by time of administration for the group of patients and delivered to the caregiver location for that group of patients (e.g. a wing of a patient floor in a long term care facility).

The healthcare platform may further facilitate populating of E-EHR with the clinical outcome data. Outcome data may include patient response to medication, resolution or worsening of symptoms, onset of new symptoms, and the like. The outcome data may include pain, fatigue, physical functioning, emotional distress, and social role participation that may have a major impact on quality-of-life across a variety of chronic diseases.

The clinical outcome data may be obtained from various sources. In an exemplary case, the clinical outcome data may be obtained by providing a questionnaire over the web portal. Patients may access the web portal and fill the questionnaire. The questionnaire may be accessed through user name and password which may be provided by the healthcare platform to the patient. Further, the questionnaire may include interview based subjective questions. The patient may also be asked to write his answers in free form as to what he feels. The questions in the questionnaire may also be provided in the form of multiple choices. Further, the healthcare platform may provide incentives to the patients to fill the questionnaire and provide the clinical outcomes. The incentives may include providing discounts on filling the medical prescriptions. Further, the discounts may be provided over self health testing equipments. The self health testing equipments may include equipments for measuring blood glucose level. The self health testing equipment may also include blood pressure measuring equipment. The healthcare platform may further provide incentives for interaction over patient portals that are healthcare related online web applications allowing patients to interact with their doctors, physicians.

The clinical outcome data may also be collected from diagnosis based news groups. These news groups may be online web applications where the patients or participants may seek advice about the treatment or medication from other patients or participants who may have already experienced a similar kind problem. The clinical outcome data from such news groups may be collected by the healthcare platform by automatic scanning of keywords. In an example, the keywords may include terms of a particular medication, a particular diagnosis or treatment or any type of clinical outcome. Further, these keywords may be weighted differently by the healthcare platform.

The clinical outcome data may further be collected by conducting regular visits of patient or participant at the doctor's office. In other cases, the clinical outcome data may be collected from the patient's house. The medical administration data associated with the patient may be collected from the patient's house. Further, the nurses may visit the patient's residence to collect vitals associated with the patient and later obtain the clinical outcomes with the help of these vitals. The vitals associated with the patient may include body temperature, pulse rate (or heart rate), blood pressure, and respiratory rate. The clinical outcome data may further be obtained by visiting offices of medical specialists. The medical specialists may include Ophthalmologist, Endocrinologist Gastroenterologist, Gynecologist, Hematologist, Laryngologist, Cardiologist, Neurologist, Orthopedic surgeon, Oncologist, Pathologist, Pediatrician, Dermatologist, Radiologist, Rheumatologist and other medical specialists.

The clinical outcome data may further be collected by visiting emergency rooms of hospitals. The condition or the state of the patient in the emergency room may be analyzed to obtain the clinical outcome data.

Further, the clinical outcome data may be obtained by diagnosing the patients in the hospital. The diagnosis may be conducted by providing a questionnaire to the patients and asking them to answer questions related to their health.

Further, the clinical outcome data may be obtained from hospitals and clinics where the outpatients regularly visit. Such outpatients may be provided a questionnaire related to the treatment they are undergoing at the hospitals and clinics.

Further, the clinical outcome data may be obtained from patients that are in long term care. The vitals of these patients may be regularly obtained to analyze the outcome of the drugs. The activity levels of these patients may also be monitored regularly to obtain clinical outcomes. The outcomes may also be obtained by analyzing the mood of the patient, the movement of the patients, the type of activity they perform and the performance of their tasks.

Another valuable source of clinical outcome data is that collected bedside at contemporaneous with the administration of medication. Upon administration of medications at the bedside, the caregiver may be prompted to collect other relevant data. In a preferred embodiment of the invention, the data related to outcomes may be collected by the person administering the medication at the time of administration, and thus may be entered into the HPDMA 100 along with the medication administration data. Therefore, the HPDMA 100 may include means for prompting the care giver to enter this information at the time of administration.

Because HPDMA 100 provides for the real time tracking of medication administration data plus the contemporaneous collection of outcomes related to the medication, the outcome engine has the ability to determine the efficacy of a drug—in effect, potentially providing the ability to conduct ad hoc studies. For example, 6000 patients with condition A may exist. All 6000 of them are on drug X. 3000 of them are on drug X for condition A and drug Y for another condition. The 3000 on both drugs may fare better with respect to condition A. The methods and systems described herein allow one to extract such information and see connections that might have not otherwise been seen. In another example, some patients taking drug D may stop taking a medication before the full prescribed amount is consumed because symptoms rapidly improve, whereas others do not find improvement until the full course is administered. Using the method and systems of the HPDMA 100 as described herein to analyze the full enhanced electronic health records of these two classes of patients, statistically relevant factors among the classes of patients that may support the symptom improvement findings may be detected.

In embodiments of the invention, the event outcome analytics facility 124 may track the event outcomes that may be triggered from the various facilities depicted in FIG. 1. These tracked event outcomes may be collected in real time to be utilized by different computer applications to provide various types of outputs. In embodiments of the invention, the different types of outputs may include, without any limitations, (1) predictions of treatment or clinical outcomes, (2) predictions about costs of patient recovery or recuperation, (3) grading or ratings for healthcare facilities, healthcare professionals, medication effectiveness, and patient acceptance, (4) reimbursements provided by the insurance companies for different types of medications, and (5) customized clinical trials databases.

The outcome analytics facility 124 may collect data in real time from various sources and facilities. In an embodiment of the system, the outcome analytics facility 124 may collect the events outcome from a middleware facility. The middleware facility may be a part of the three-tier architecture which may be provided by the healthcare and pharmacy data management and administration 100. In the three-tier architecture the presentation, the application processing, and the data management may be logically separated to each other. The middleware facility may allow the various facilities, depicted in FIG. 1, to service data requests between a user and a database. In embodiments of the invention, the database may be associated with the E-EHR/E-EMR facility 118 or may be a third party database. Further, the database may be accessed by the dashboard facility 150 to present different types of reports to the user. The access of the database may also be required by the outcome analytics facility 124 to provide predictions related to the outcomes.

Further in embodiments of the invention, the healthcare and pharmacy data management and administration 100 may allow the ordering of the collected data and the structuring of the collected data into various medical databases. In an embodiment of the invention, the structuring of the collected data may be based on the different types of events. The different types of events may be related to the prescribing facilities, the care planning facilities, the laboratories & imaging centers, the insurance & payments, the rehabilitation and long term care facilities, the electronic medical record repositories, the dashboards and databases, the third party sites, the healthcare facilities, and the like. In another embodiment of the invention, the structuring of the collected data may be based on the diagnosis details of the one or more patients. In an example, the event outcome data collected for a group of patients diagnosed with the same disease may be structured together in a database. In yet another embodiment of the invention, the structuring of the collected data may be based on the treatment provided to the one or more patients. In yet another embodiment of the invention, the structuring of the collected data may be based on the nature of the outcomes. In yet another embodiment of the invention, the structuring of the collected data may be based on the demographics of the patients. In examples the demographics of the patients may include their date of birth, gender, birth year, country, postal code, ethnicity, blood type, family doctor, insurance provider and the like.

Further in embodiments of the invention, the outcome analytics facility 124 may perform a real time tracking of the outcomes associated with the prescribing events and the pharmacy fill events.

In embodiments, once the event outcome data associated with the various facilities is collected, the collected data may be utilized by different computer application facilities to provide various types of outputs. Alternatively, the computer application facilities may utilize the data from the E-EHR/E-EMR facility 118 to provide various types of outputs. In an embodiment of the invention, the computer application facilities may utilize the collected event outcome data to provide predicted outcome data.

In another embodiment of the invention, the computer application facilities may utilize the collected event outcome data to predict costs of a patient recovery or recuperation. The costs of the patient recovery or recuperation may directly relate to various parameters like, but not limited to, the cost of administering a particular medication to the patient, the reimbursements provided by the insurance companies for that medication, the cost of long term care provided by the health care facility, the cost of rehabilitation centers provided by the health care facility, the cost involved in various types of laboratory tests, the cost of admission in the healthcare facility and the like. Further, the collected event outcome data, from different facilities (depicted in FIG. 1) and other sources, may relate to all these discussed parameters. The computer application facilities may thus apply, known in the art, prediction and financial algorithms on the collected event outcome data to predict the cost of patient recovery.

In other embodiments of the invention, the computer application facilities may utilize the collected event outcome data to grade or provide ratings to facilities provided by the healthcare facility, healthcare professionals, medication effectiveness, and patient acceptance.

The effectiveness of a medication may be measured in terms of its clinical outcomes. For example, equal number of dosages of different medications, administered to a patient for a disease, may yield different clinical outcomes. Thus, the medication that may yield better and desirable clinical outcomes with less number of dosages may be considered effective. A medication may also be considered effective if the medication is able to cure more than one disease. The effectiveness of a medication may also be measured in monetary terms by analyzing the economical perspective of the medication. For example, there may be more than one effective medication that may be used to treat a set of diagnosed symptoms; one of these may be more expensive than the other but equally effective with regard to alleviating symptoms of the patient. In this scenario, the financial value may determine the selection of the medicine and the medication with less cost may be considered more effective. Further, the collected event outcome data may correspond to effectiveness of different types of medications. The computer application facilities may apply, known in the art, correlation algorithms to rate or grade the effectiveness of the medications.

The collected event outcome data may also provide information about the patient's acceptances to various types of medications, treatments and facilities. The acceptances to different types of medications and treatments may be measured by the clinical or treatment outcomes. The acceptances to different facilities (e.g. LTC and rehabilitation) of a healthcare facility may be measured by the checking the number of patients opting for those facilities. Further, the computer application facilities may apply, known in the art, algorithms to rate or grade the acceptances patients to various types of medications, treatments and facilities. In an embodiment of the invention, the information about the ratings of the facilities provided by the healthcare facility, the ratings of the healthcare professionals, the ratings of medication effectiveness, and the ratings of patient acceptances may be sold to a publication company for publishing the information in the articles of journals related to medical science.

In other embodiments of the invention, the computer application facilities may utilize the collected event outcome data to provide customized clinical trials database.

In an embodiment of the invention, the database storing the collected event outcome data may be linked to a website of the healthcare facility to provide non confidential information including, but not limited to, ratings of healthcare professionals associated with the healthcare facility, medication effectiveness administered by the healthcare facility, patient acceptance to administered medications and facilities provided by the healthcare facility. The website of the healthcare facility may provide information about the amount of reimbursements provided by insurance companies to the administered medications, facilities used and the like. In an example, a user or a potential patient of the healthcare facility may visit the website provide by the healthcare facility to check the reimbursements provided by insurance companies for certain medications that are administered by the health care facility. As the website is linked to the database of collected event outcome data, the website upon applying some known in the art algorithms may provide the reimbursement details to the user. Further, the website may provide an updated information to the user as the data is event outcome data is tracked, collected and updated in real time.

The HPDMA 100 may include connecting in real-time a diversity of data collection, storage, entry, display, management, and maintenance systems. Each of these systems may have unique data rules, formats, needs, and the like that may make sharing healthcare related data among them challenging. One option for dealing with these challenges is to implement software or software-based computing systems that can operate between the diverse facilities and databases forming a middleware that facilitates consistently sharing data. Middleware may support data format transformation, form filling, data field compliance checking, business rules normalization, and the like that may allow data from diverse systems to be shared and combined with high quality results. Middleware may be embodied as software that executes on computers, such as servers, clients, hosts, network appliances, medical devices, and the like to allow data that may be natively captured, entered, or stored by a computer associated with a particular facility (e.g. medication administration) to be shared with other facilities (e.g. as shown in FIG. 1) without requiring the two facilities to have identical data formats, business rules, and the like. Middleware may be a combination of software and hardware that may be integrated with any facility depicted in FIG. 1 or that may be a self-standing system that is connected to the backbone 103, or various combinations thereof A couple of exemplary cases may be helpful in understanding how middleware may facilitate data sharing among the facilities depicted in FIG. 1. In a first example, data from a laboratory facility (e.g. mammography imaging lab) may include device specific or industry standard image data, patient data, automated analysis data, technician observations, radiologist interpretation data, and the like. This data may be combined with mediation administration data that may be captured partially from a device reader, from a caregiver administering the medication, and from a prescription management facility based on the device reader captured data to be stored in an enhanced electronic health record. Ensuring that data from these many sources can be effectively combined into one enhanced electronic health record that can be used by other facilities (e.g. dashboards, outcome analytics, various planning facilities, and the like) may be accomplished with middleware. In a second example, raw barcode data that may be captured by a hand held scanner during a medication administration event may be transferred in real-time to a pharmacy management dashboard for display to a pharmacist. The raw barcode may be transformed by middleware so that it can be properly displayed in the dashboard. Because the raw barcode data may require further context to be properly displayed in the dashboard, middleware may use the raw barcode data to lookup patient information in an enhanced electronic health record database, combine the patient information with transformed medication data (e.g. from the raw barcode data) and facilitate presenting the combined data to the pharmacy dashboard.

The middleware methods and systems of the HPDMA 100 may be used to transform data received from the diversity of facilities to a common format based on pre-defined criteria for use in a common datastore (e.g. an enhanced electronic health record). Middleware may alternatively transform manually entered data into machine-readable format. Middleware may also support structural association of data, filtering of data, and the like.

The middleware facility may include processes that may facilitate storage of data in the common datastore. In this aspect, the data may be normalized before being stored in the datastore. The normalization may facilitate reducing redundancy of data, ensuring data consistency, optimizing data retrieval from a common data store, and the like. In an example, the patient data may be normalized by allocating a unique patient identification number for all of a patient's data stored in the common data store. The normalization may require that the unique patient identifiers associated with each of the diversity of medical facilities be transformed by the middleware to the unique patient identifier Middleware may ensure that data is cleaned before storing it into a common database. Cleaning of data may be accomplished by filtering the data, breaking up complex data into uniform data fields, and the like. In an example, a delimiter character may be present in data being received from a patient attribute facility and the delimiter may be removed by the middleware before the data is recorded in the database. Alternatively, data received from a prescribing facility may include brand name data for a prescription. Middleware may support filing in a generic medication field of an enhanced electronic health record based on the brand name found in the prescription.

Middleware may be embodied in technologies such as SOAP, web services, service-oriented architecture or other similar technologies.

Middleware may facilitate distributing a common datastore, such as an enhanced electronic health record across various medical-related facilities (e.g. those depicted in FIG. 1) by handling the data format transformation, correlation, lookups, and the like needed to ensure that any view of the distributed data exhibits consistency across the data sources. Likewise, middleware may facilitate communication among the facilities through secure means, such as virtual private networks and other network tunneling techniques that work cooperatively with firewalls and the like.

Healthcare planning, also called Care Planning, is a key to improving the health of the population of a region, a country, and the like. In most countries, healthcare planning and management takes place at national, regional or local level reflecting various tiers of government for healthcare systems. Healthcare planning may include offering various health facilities to citizens of a country. Healthcare planning may be provided and/or maintained by many entities such as governmental, non-profit, and private entities. For example, healthcare organizations such as hospitals can provide comprehensive medical facility planning services to people. Healthcare planning may include various plans in accordance with the requirement of people. For example, a family health plan will be aimed at the full family while a group employee benefit plan will be an employee welfare oriented plan established or maintained by an employer or by an employee's organization. In addition, a health plan may be a subscription-based medical care arrangement offered by commercial insurance companies.

Efficient healthcare planning may require defining appropriate goals and objectives that may further facilitate the creation of appropriate strategies for implementing the same.

The data requirements to achieve the objectives and goals for a care plan may be driven by a number of factors and/or macro forces such as demography, role of government, environmental shift, social set up, healthcare innovation and competition, regulations, and the like. This may be apparent by way of a few examples that are described below.

Healthcare planning may be aimed at improving the physical and functional status of the public health based on the health status and disease profiles for a given demography or region. Therefore, access to timely, accurate, comprehensive, and diverse medically-related event data may be important for healthcare planning. For example, reduction of communicable disease profiles in a Sub-Saharan region may be an objective for a healthcare entity that may be more readily achieved with real-time data for patients and others in the region. Similarly, the objective of healthcare planning may be to meet the high levels of healthcare reforms promised by the government. In such a scenario, measuring health care quality, actions, results (outcomes), and the like is essential to ensure that reform goals are met. The methods and systems described herein may provide data for such healthcare planning activities.

It is also known that diseases are linked to climate changes. In light of this, the healthcare planning goal may be to decrease medical plan utilization for environmentally borne diseases such as malaria. By collecting bed-side data and associating it with medical plan data, movement toward such a goal may be measurable. With respect to healthcare innovations and regulations, the objectives of care planning may be to make the most effective branded drugs readily available and affordable for those who demonstrate a need for such drugs. By collecting and analyzing medication prescription, administration, and outcome data, the methods and systems herein may facilitate determining an efficacy of medications. In sum, the data needs of care planning may encompass data related to prevention and control of health problems, judicious planning, optimization, and utilization of healthcare resources, and the like.

Care planning may require health data from various sources that may be useful in planning patient treatment. This data may relate to physiological, emotional, and environmental wellbeing of an individual. For this purpose, medical history of a patient may be utilized. Examples of physiological health data may include weight, age, blood pressure, glucose levels, blood cells count, hemoglobin levels, hypertension, cholesterol, stroke, pre-clampsia, diabetes, allergy, seizures, asthma, and the like. Similarly, emotional well being data may include information on stress levels, lifestyle patterns, relationship issues, EQ quotients, any special needs, and the like. Further, examples of environmental well being may include information on exposure to pollution, neighborhood conditions, food supply, and the like. These types of data may be readily available to care planning activities by accessing an enhanced electronic health record as described herein.

The healthcare plans may be offered to individuals or customers based on their needs that may be ascertained from profile information or medical history. This also forms the basis of developing goal-oriented healthcare plans. For example, an over-weight patient may be offered a weight reduction health plan for achieving a desired weight. Similarly, a person with high systolic blood pressure may be offered a health program that may include exercise regime for controlling the blood pressure, and the like. Not only can an enhanced electronic health record capture patient conditions and changes, it can also include plan data (e.g. weight goals, and the like) that makes the further assessment of a patient's progress and predicting the outcome for treatments toward the goal possible.

Care planning may be designed for specific needs of various individuals. The healthcare needs for women, children, elderly, professionals, defense personnel, and the like may differ significantly from each other. For example, for women a health plan focused on maintaining adequate bone density or maintaining hormonal balance may be required and specifically for pregnant women the health plan may be focused on overall nourishment. Likewise, healthcare needs of children aged 2-8 may be different from those of teenagers. For professionals with hectic working hours, a plan that leverages the exercise and diet routine may be preferred. Similarly, for the elderly or defense personnel a specific weight or glucose level goal may be the focus of a health plan. Ensuring that healthcare planning can encompass these very diverse goals and needs may require access to a diversity of data from a diversity of medical facilities, such as those described in FIG. 1 of the present invention. The HPDMA 100 as described herein may provide the means and capabilities to support achieving diverse care planning goals.

Care planning may be designed based on patient touch points such as office visits, emergency room visits (ERs), inpatient and outpatient quarters, rehabilitation centers, and the like. For example, data for a care plan for an emergency room may be intensive and focused and may require real-time data collection, access, and dashboarding. Multidisciplinary teams of experts may be deployed in the ER areas to meet the variety of patient needs. In addition, with real-time access to administration and outcome data for a plurality of patients, detailed, individualized care plans may be developed for an emergency department.

Similarly, a care plan for a rehabilitation center may focus on a number of parameters such as background needs of the patient, medical equipment needs, home healthcare environment needs, nutrition, supply, commodities, education & training, and the like, all of which may be determined from outcome and treatment data of a wide diversity of rehabilitation center patients across the country. Such data may be accessible in a nationally maintained enhanced electronic health record system as described in FIG. 1.

Also, the needs of inpatients and outpatients may be different, emphasizing the need for different care plans for both of them. Inpatients may require nutritional and daily care (temporary) support such as bathing or dressing while outpatients may prefer a short queuing time for medications and check-up.

Maternity wards may also require a well designed care planning. For example, requirement for a hygienic and separate ward for newborns and those with special needs.

Insurance processing is a method of collectively pooling the risks of insurance payouts across a diverse population. Specifically for healthcare, risk for incurring medical and health expenses may be pooled among the various entities (patients, insurance companies, health professionals, etc.) Healthcare insurance processing may include various data-related steps such as data collection, data validation, insurance claims processing, insurance clearance, payments, expense justification, recovery analysis, and the like. The methods and systems described herein may provide such data in real-time and over a long period of time from a diversity of patients.

Data collection may be a highly significant step in the insurance process. This may include collection of information pertaining to a variety of data such as medical history of a patient, current diagnosis, treatment prescribed, therapist/surgeon/medical specialist information, follow-up treatment, frequency and duration of treatment, amount/mode/process of payment, and the like.

The medical history of a patient may include information from physical examination of a patient for various elements such as general survey, skin, head, eyes, ears, nose & sinus, mouth, throat, neck, chest, tumor growth, lungs, heart, abdomen, extremities, lymphatic blood vessels, neurological, and the like. The medical history may also include information on previous diagnoses, consultations, and examination by physicians or medical practitioners. The medical history may also reveal if the patient has utilized any diagnostic, therapeutic (surgical or non surgical), and rehabilitation services in the past. An enhanced electronic health record may combine current and past medical treatment and outcome data for an individual across geographic locations, insurance plans, life changes, and the like.

Current diagnosis information may include various possibilities regarding the state of the current disease and symptoms. For example, if a patient is admitted to a hospital with complaints of severe pain in the pelvic region, a likely diagnosis in this case may be 'possible endometriosis.' Based on this indicative information, the insurance processing may be conducted. By providing access to data representing symptoms, treatment, and outcomes of such a diagnosis across a large number of patients, the HPDMA 100 may be found to be useful in determining the monetary range for insurance claims that may be required for relevant treatment options.

Information on medical practitioner, specialist, surgeon, and physician may also be significant for insurance processing. Because the charges and or expenses related to a medical treatment may depend on the medical practitioner, knowing something about the efficacy of a practitioner in treating a specific condition may influence how much an insurance company may be willing to pay for the practitioner's services. By allowing access to certain information across a wide range of patients, the HDPMA 100 may facilitate such efficacy determination.

Similarly, information regarding mode of payment such as cash or credit, onetime or periodic may be useful for insurance processing. In case the payment mode is credit-based, the issuing bank information (name, location, policies) may be of importance for insurance parties. While it may be preferable to limit access to financial information that is associated with a patient, the enhanced electronic health record as described herein may facilitate making this information securely accessible and readily linkable to other information in the record that may be pertinent to insurance processing.

Further, insurance processing may also include information regarding the payment/co-payment, and reimbursement options. By ensuring that medication administration data is automatically and accurately collected, it may be possible to collect data to support reimbursement of out of pocket costs for unused medications.

A well planned and well designed facility may provide long term benefit to a healthcare organization. This may also be significant with respect to the organization's objectives such as financial productivity, meeting demand for services and changes in technology for healthcare, optimal utilization of already existing healthcare resources, and the like. Healthcare providers and planners may utilize healthcare data for devising solutions for facility planning and space programming for healthcare services.

Healthcare data for facility planning may be related to the mix ratio of inpatient and outpatient services, older and critically sick patient population, treatment patterns, advancement in technology, health data related to diseases and conditions (asthma, cholesterol, diabetes, heart disease, hypertension, obesity, etc.), type of healthcare (ambulatory services, ER visits, etc.), data related to injuries (accidents, suicides, homicides, etc.), life stages and population (births, deaths, women's health, children's health, state and territorial distribution, etc.), lifestyle (drug use, smoking, exercise, etc.), and the like. Each of these data fields and their role in healthcare facility planning will be discussed in detail in the following description.

In accordance with various embodiments of the present invention, healthcare data may be an aggregated or composite healthcare data. The healthcare data may be obtained from public sources such as statistics published by government agencies, research groups, and web engines or from secondary sources such as medical history or profile information of patients visiting a healthcare facility.

The mix ratio of inpatient and outpatient services may be a factor for facility planning. For example, a higher number of outpatient services may be an indicator of an additional outpatient ward. Similarly, an increasingly high number of older patient populations may call for design of facilities that reduce waiting time during admission and discharge, provision of wheelchairs, canes, elevators, provision of chemist shops within the facility, long term care units, and the like.

The advancement in technology for example, digital imaging technology may affect facility design and planning for a healthcare unit such as a diagnostic and interventional radiology facility or laboratory. Conventionally, film-based imaging departments constituted dark rooms, large file rooms, large central technical work area, and a minimal preparation and recovery area. Current advancements in technology require highly specialized and advanced telecommunications infrastructure capable of rapid transmission of large data files to workstations throughout the hospital, physicians' offices in the community and even consulting radiologists halfway around the world. Facility design may require consideration of all such factors.

Data (public or secondary) regarding the diseases and conditions may also be pertinent for facility planning and management. Increased number of cases reported for asthma and obesity may lead to designing of facilities that are dust free and equipped with exercise apparatus, respectively.

A high number of emergency room visits may indicate a need for designing the ERs and trauma centers such that the amount of time taken to carry the injured to these facilities may be minimized. These facilities may be designed near a small helipad within the healthcare unit (if possible) for catering to emergency situations such as disaster (fire, accident, earthquake, etc.)

Similarly, information pertaining to injuries may be useful in integrating the main healthcare facilities with some additional facilities. For example, if the statistics indicate high number of suicide cases in a given region, centers for preventive treatment (yoga, alternate medicine, meditation, community centers, etc.) may be provided with a hospital.

Various life stages and population statistics (birth and mortality rates, gender statistics, etc.) may be useful for facility design. For example, an increase in the number of children's health records in a community may indicate a need for planning a child friendly healthcare center in that community. Likewise, a disproportionate male-female child ratio in a developing country may indicate need for a community center that may act as an awareness camp for the masses.

A long term care center or a facility may provide rehabilitative, restorative, and/or ongoing skilled nursing care to patients or residents in need of assistance with activities of daily living. This facility planning may require specific consideration and design than the facility planning for a general healthcare center since it may cater to the needs of a specific group (e.g., elderly or homeless) that are otherwise not able to get focused healthcare and attention. Examples of long-term care facilities may include nursing homes, rehabilitation facilities, inpatient behavioral health facilities, long-term chronic care hospitals, and the like. Long term care facilities may be designed to make them safe, functional, durable and relatively easy to maintain. Some parameters to be considered while designing the long term care facilities may include design, layout, ambience, color management, dining and food management, online and kiosk-based layouts, and the like. For example, the facilities may be designed to include automatic ID scanners for residents using the dining facility.

Facility operations may be planned by collecting aggregated content from Enhanced Electronic Health Records (E-EHR as described herein) of the patients in a healthcare center or hospital. The E-EHR data may correspond to information regarding inpatients, outpatient, staff, administrators, and the like. Based on these records facility layout may be planned. For example, a yoga center or gymnasium may be provided in close vicinity of the hospital for the benefit of the healthcare professionals working in shifts or emergency areas and who are not able to attend the same due to unpredictable job demands.

Facility planning may also be related to medication supply management. A separate section or layout may be designed for provision of medicines and other health related equipments and aids such as belts, bandages, syringes, etc.

In accordance with an embodiment of the present invention, these medicine counters may also be self-help desk counters or online kiosks. Provision of such medication centers may facilitate smooth work flow for patients, administrators, guardians, etc., may be effective due to reduction in time between diagnosis and administration of medicines, and may be cost effective. In addition, it may also reduce the problems associated with non-availability of certain medications outside the hospital premises. Determining how and when to effect a medication supply facility (e.g. prescription management, medication inventory management, packaging, dispensing and the like) may require accurate and timely data collection about the prescriptions, a prescriber, patients, medications prescribed, outcomes, and the like being served by the facility and by other facilities. The methods and systems described herein in association with the HPDMA 100 may provide such capabilities.

Further, these counters furnished with cost effective drugs may minimize illegal sale of drugs. For example, Tamiflu for swine flu may be sold at the hospital counters at lower price, thus encouraging people not to buy the same illegally from outside stores. In addition, this may help the government and health agencies in maintaining proper supply and demand for emergency medications by discouraging stocking of these medications outside.

Facility planning may also involve scheduling of various tasks and resources in a healthcare unit. Scheduling may include scheduling patients for appointments, diagnosis, surgery, tests, consultation; rooms for admission, clean-up, administration, operations; healthcare professionals and specialists for meetings, visits; and the like. By providing access to prescription management data, that may include administration information such as administration schedules, requirements, and the like, a facility planning function operating in conjunction with the HPDMA 100 may substantially improve the value and efficiency of such facility planning Scheduling may be performed manually or automatically with the aid of software and tools. This activity may be pertinent since some of the tasks may be period specific. For example, radiation treatments may be provided only on weekdays and not on weekends, thereby, necessitating the need for scheduling the appointment of the patients with the therapists from Monday to Friday.

In addition, scheduling may be significant to accommodate any alterations or revisions in the pre-decided schedule; for example, accommodating absence of one specialist by another on any given day.

Furthermore, scheduling may be important for some activities that may be sequential in nature. For example, scheduling a steam bath after a therapeutic massage session. This type of scheduling may facilitate optimization of given resources for an organization. In sum, facility planning may require consideration of availability of given resources and to address requirements for handicaps like inability to climb staircase, visual impairment, special washroom facilities, etc.

The HPDMA 100 may also be associated with insurance planning facilities as depicted in FIG. 1. Insurance may be provided by government-sponsored social insurance programs or from private insurance companies and it may be applicable to an individual or to a group. An objective of the insurance planning is to ensure adequate medical coverage is provided to protect the covered groups or individuals from unexpected healthcare expenses by payment of premiums or taxes.

Insurance planning may use information provided by the various facilities of the HPDMA 100 and in particular E-EHRs 118, outcome databases 124, and the like to make adjustments in available plans based on the suitability of such insurance plans based for an individual. Plan parameters that may be impacted by insurance planning may include customary fees, exclusions, maximum out-of-pocket expenses, non-cancellation cases, premium, and the like.

The accessibility of a large number of enhanced electronic health records in an E-EHR database may facilitate establishing a generic profile of patients and their caretakers for insurance planning. For example, insurance planning using the generic profile may result in a new insurance plan being offered to individuals with a high risk job profile.

Pharmaceutical or pharmacy planning is another area that may benefit from access to various data from the facilities and data sources of the HPDMA 100, such as for devising pharmaceutical related decisions. These data source may include medical history data from the care planning or validation diagnosis aspect of the HPDMA 1000, laboratories and imaging facilities, rehabilitation facilities, databases of past medical records (e.g. E-EHR), third party data sources, and the like.

In certain cases, market driven research may be required for making a pharmacy related decision. The data from market research may relate to marketplace environment, treatment choices available, providers and patients profile, behavioral patterns, and the like. At least a portion of such data may be derived from pertinent information accessible in an E-EHR.

A data source such as outcome data (e.g. outcome database 124) may reveal that patients suffer from a side effect e.g., stomach infection after taking a particular medication. In light of this observation, planning may be done regarding changing the prescription instructions. In extension to this, pharmacy-related planning may also include devising methods and processes to make this possible side-effect and administration information public, such as by means of improving product packaging broadcasting through print and electronic media, and the like. Alternately, pharmacy planning may include development of a medication that is easier to digest or development of a medication that may suppress the side effects of the previous drug.

Drug delivery mechanism may also be significant with regard to pharmacy planning By analyzing outcome data, it may be determined that a particular oral drug formulation may not be preferred by consumers because of its bitter taste so planning may be done to prepare the drug in inhalable form.

Regulatory and compliance needs may be a cause of concern for healthcare professionals since these regulations may directly affect an organization's profitability and business success. Accurate, comprehensive data collection may be essential to properly complying with regulatory requirements. By providing robust, detailed, timely, and comprehensive data collection, medication tracking, administration record keeping, and the like, the HPDMA 100 may provide individuals responsible for meeting regulatory requirements with beneficial tools that ease such compliance. Planning and decision making based on this information may be improved with respect to improving and meeting compliance, addressing existing deficiencies in the processes, reducing business risks, and the like.

Collection of regulatory data may be necessary and significant for the continuous monitoring and reassessment of a drug's safety, quality, and efficacy/effectiveness. The HPDMA 100 may provide a platform for ensuring compliant data collection and management.

The methods and systems described in connection with facilities described herein, and the operational control of the dispensing machine or any component of a facility described herein (the "Subject Methods and Systems") may be deployed in part or in whole through a machine that executes computer software, program codes, and/or instructions on a processor. The Subject Methods and Systems invention may be implemented as a method on the machine, as a system or apparatus as part of or in relation to the machine, or as a computer program product embodied in a computer readable medium executing on one or more of the machines. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor, or any machine utilizing one, may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. The process may be a dual core processor, quad core processors, other chip-level multiprocessor and the like that combine two or more independent cores (called a die).

The Subject Methods and Systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

If the Subject Methods and Systems are embodied in a software program, the software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The Subject Methods and Systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions pertaining to the Subject Methods and Systems described herein and elsewhere may be implemented on a cellular network having multiple cells. The cellular network may either be frequency division multiple access (FOMA) network or code division multiple access (COMA) network. The cellular network may include mobile devices, cell sites, base stations, repeaters, antennas, towers, and the like. The cell network may be a GSM, GPRS, 3G, EVOO, mesh, or other networks types.

The methods, program codes, and instructions pertaining to the Subject Methods and Systems described herein and elsewhere may be implemented on or through mobile devices. The mobile devices may include navigation devices, cell phones, mobile phones, mobile personal digital assistants, laptops, palmtops, notebooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions pertaining to the Subject Methods and Systems may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, stand-alone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The Subject Methods and Systems described herein may transform physical and/or or intangible items from one state to another. The methods and systems described herein may also transform data representing physical and/or intangible items from one state to another.

The elements described and depicted herein, including in flow charts and block diagrams throughout the figures, imply logical boundaries between the elements. However, according to software or hardware engineering practices, the depicted elements and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The Subject Methods and Systems, and steps associated therewith, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above in connection with the Subject Systems and Methods and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable bylaw.

All documents referenced herein are hereby incorporated by reference.

The invention claimed is:

1. A system to manage the prescribing and administration of medication, comprising:
    a medication management facility comprising an electronic order entry facility configured to receive electronic medication orders, the medication management facility configured to perform at least one of:
        a) a verification of formulary compliance;
        b) a determination of drug allergy information associated with the electronic medication orders; and
        c) a determination of drug interaction information associated with the electronic medication orders;
    a medication validation and billing facility in electronic communication with the medication management facility, the medication validation and billing facility configured to receive the electronic medication orders, provide information regarding formulary compliance, the drug allergy information, and the drug interaction information, and further comprising an interface for receiving input from a pharmacist to approve the electronic medication orders;
    a medication dispensing machine in electronic communication with the medication validation and billing facility, and configured to receive the approved electronic medication orders and dispense a plurality of dosages of medications based on the approved electronic medication orders, wherein dosages of the plurality of dosages of medications are packaged by the medication dispensing machine in packaging comprising electronically readable information regarding the corresponding dosage of medication and including information regarding the expected location of the recipient of the corresponding dosage of medication in a healthcare facility;
    a medication cart configured to store and distribute the packaged dosages of medications for administration to a plurality of patients in the healthcare facility;
    a workstation having an output facility, the workstation in electronic communication with the medication management facility; and
    a reader device with a GPS facility in electronic communication with the workstation and capable of reading the electronically readable information regarding at least one packaged dosage of medication of the plurality of dosages of medications loaded on the medication cart during an administration attempt of the at least one dosage of medication to a respective recipient of the plurality of patients in the healthcare facility and also providing location data of the medication at the time of the administration attempt, wherein the workstation transmits the electronically readable information regarding the at least one packaged dosage of medication and the location data from the reader device to the medication management facility, and wherein the medication management facility generates a warning if the electronically readable information or the location data transmitted from the reader device differs from a current electronic medication order corresponding to the at least one dosage of medication.

2. The system of claim 1, wherein the workstation is mobile.

3. The system of claim 1, wherein the medication validation and billing facility associates data with corresponding approved medication orders, wherein the data is at least one of patient insurance information, facility personnel associated/responsible for the patient, and administration frequency.

4. The system of claim 1, wherein medication management facility further comprises a medication administration facility.

5. The system of claim 1, wherein the medication administration facility prompts a caregiver administering the at least one dosage of medication to enter information associated with administration of the at least one dosage of medication at the time of administration.

6. The system of claim 5, wherein the information associated with administration of the at least one dosage of medication is read by the reader device.

7. The system of claim 5, wherein the information associated with administration of the at least one dosage of medication comprises at least one of time of administration, mode of administration, and identity of the caregiver that administered the medication.

8. The system of claim 1, wherein the medication administration facility prompts a user to verify that a dosage has been administered to a patient.

9. The system of claim 1, wherein the dosages are individually packaged.

10. The system of claim 1, wherein the reader device is a bar code scanner.

11. The system of claim 1, wherein the medication management facility further comprises a therapeutic equivalent facility.

12. The system of claim 11, wherein the therapeutic equivalent facility determines a therapeutic equivalent for an electronically ordered medication.

13. The system of claim 12, wherein the therapeutic equivalent facility gathers and stores information regarding therapeutic equivalents to respective medications.

14. The system of claim 1, wherein at least one of the medication management facility and the medication validation and billing facility groups the electronic medication orders by at least one of institutional facility, patient, and facility dispensing time.

15. The system of claim 1, wherein the medication management facility further comprises a utility configured to suggest medications based on at least one of a prescriber's pattern of ordering and a diagnosis.

16. The system of claim 1, wherein the medication management facility is further configured to:
determine whether at least one of an ordered medication for a patient and a medication administered to a patient is covered by the patient's insurance;
aggregate covered and not covered medications into sets; and
generate reports, in real time, regarding the sets.

17. The system of claim 1, wherein the packaged dosages of the plurality of dosages of medications are loaded on the medication cart based on reading the electronically readable information regarding the expected location of the recipient of the corresponding dosage of medication in the healthcare facility.

* * * * *